US011191849B2

(12) United States Patent
Abrams et al.

(10) Patent No.: US 11,191,849 B2
(45) Date of Patent: Dec. 7, 2021

(54) COMPOSITIONS AND METHODS FOR DELIVERING MESSENGER RNA

(71) Applicant: ARBUTUS BIOPHARMA CORPORATION, Burnaby (CA)

(72) Inventors: Michael J. Abrams, Custer, WA (US); James Heyes, Vancouver (CA); Adam Judge, Bainbridge Island, WA (US); Kieu Mong Lam, Richmond (CA); Lorne Ralph Palmer, Vancouver (CA); Stephen P. Reid, Vancouver (CA); Edward D. Yaworski, Maple Ridge (CA)

(73) Assignee: ARBUTUS BIOPHARMA CORPORATION, Burnaby (CA)

( * ) Notice: Subject to any disclaimer, the term of this patent is extended or adjusted under 35 U.S.C. 154(b) by 0 days.

(21) Appl. No.: 16/312,162

(22) PCT Filed: Jun. 30, 2017

(86) PCT No.: PCT/US2017/040446
§ 371 (c)(1),
(2) Date: Dec. 20, 2018

(87) PCT Pub. No.: WO2018/006052
PCT Pub. Date: Jan. 4, 2018

(65) Prior Publication Data
US 2019/0240354 A1     Aug. 8, 2019

Related U.S. Application Data

(60) Provisional application No. 62/357,189, filed on Jun. 30, 2016, provisional application No. 62/375,292, filed on Aug. 15, 2016.

(51) Int. Cl.
*C07H 21/04* (2006.01)
*A61K 48/00* (2006.01)
*C12N 15/11* (2006.01)
*A61K 9/00* (2006.01)
*A61K 45/06* (2006.01)
*A61K 9/51* (2006.01)
*A61K 31/573* (2006.01)
*A61K 31/58* (2006.01)
*A61K 31/7105* (2006.01)
*A61K 31/713* (2006.01)
*A61K 47/69* (2017.01)
*A61K 47/54* (2017.01)
*A61K 47/60* (2017.01)
*B82Y 5/00* (2011.01)

(52) U.S. Cl.
CPC ........ *A61K 48/0083* (2013.01); *A61K 9/0019* (2013.01); *A61K 9/5123* (2013.01); *A61K 31/573* (2013.01); *A61K 31/58* (2013.01); *A61K 31/713* (2013.01); *A61K 31/7105* (2013.01); *A61K 45/06* (2013.01); *A61K 47/544* (2017.08); *A61K 47/60* (2017.08); *A61K 47/6909* (2017.08); *A61K 47/6911* (2017.08); *B82Y 5/00* (2013.01); *C12N 15/111* (2013.01); *C12N 2320/32* (2013.01)

(58) Field of Classification Search
CPC .............................. C12N 15/113; A61K 47/60
See application file for complete search history.

(56) References Cited

U.S. PATENT DOCUMENTS

| | | | |
|---|---|---|---|
| 7,803,397 B2 | 9/2010 | Heyes et al. | |
| 7,982,027 B2 | 7/2011 | MacLachlan et al. | |
| 8,058,069 B2 | 11/2011 | Yaworski et al. | |
| 8,466,122 B2 | 6/2013 | Heyes et al. | |
| 8,492,359 B2 | 7/2013 | Yaworski et al. | |
| 8,822,668 B2 | 9/2014 | Yaworski et al. | |
| 9,006,417 B2 | 4/2015 | Yaworski et al. | |
| 9,352,042 B2 | 5/2016 | Heyes et al. | |
| 9,364,435 B2 | 6/2016 | Yaworski et al. | |
| 9,404,127 B2 | 8/2016 | Yaworski et al. | |
| 9,504,651 B2 | 11/2016 | MacLachlan et al. | |
| 9,518,272 B2 | 12/2016 | Yaworski et al. | |
| 2006/0286161 A1 | 12/2006 | Panzner et al. | |
| 2007/0054873 A1 | 3/2007 | MacLachlan et al. | |
| 2012/0156251 A1 | 6/2012 | Brito et al. | |
| 2012/0172411 A1 | 7/2012 | Heyes et al. | |
| 2012/0183581 A1 | 7/2012 | Yarworski et al. | |

(Continued)

FOREIGN PATENT DOCUMENTS

| | | |
|---|---|---|
| CA | 2859387 A1 | 6/2013 |
| WO | 2009082817 A1 | 7/2009 |

(Continued)

OTHER PUBLICATIONS

Judge, A., et al., "Overcoming the Innate Immune Response to Small Interfering RNA", Human Gene Therapy 19, 14 pages (Feb. 2008).

Kariko, K., et al., "Generating the optimal mRNA for therapy: HPLC purification eliminates immune activation and improves translation of nucleoside-modified, protein-encoding mRNA", Nucleic Acids Research, vol. 39 (21), e142 (2011).

Ou, L, et al., "Treatment of Experimental Crescentic Glomerulonephritis (CreGN) with Glucocorticoid Encapsulated in Newly Developed Cationic Liposomes", Journal of the American Society of Nephrology 11, p. 497A, 33rd Annual Meeting of the American Society of Nephrology and the 2000 Renal Week, Toronto, Ontario, Canada, Oct. 10-16, 2000.

(Continued)

*Primary Examiner* — Amy H Bowman
(74) *Attorney, Agent, or Firm* — Viksnins Harris Padys Malen LLP

(57) ABSTRACT

The present invention provides compositions comprising nucleic acid molecules, such as mRNA molecules, encapsulated within lipid particles. The compositions are useful, for example, to introduce the mRNA molecules into a human subject where they are translated to produce a polypeptide that functions to ameliorate one or more symptoms of a disease.

10 Claims, No Drawings

(56) References Cited

U.S. PATENT DOCUMENTS

| | | |
|---|---|---|
| 2013/0115274 A1 | 5/2013 | Knopov et al. |
| 2013/0259923 A1 | 10/2013 | Bangel et al. |
| 2013/0259924 A1 | 10/2013 | Bangel et al. |
| 2013/0345286 A1 | 12/2013 | Gollob et al. |
| 2014/0010861 A1 | 1/2014 | Bancel et al. |
| 2014/0294937 A1 | 10/2014 | MacLachlan et al. |
| 2015/0232883 A1 | 8/2015 | Dahlman et al. |
| 2016/0151284 A1 | 6/2016 | Heyes et al. |
| 2016/0256567 A1 | 9/2016 | Heyes et al. |
| 2016/0256568 A1 | 9/2016 | Heyes et al. |
| 2017/0007702 A1 | 1/2017 | Heyes et al. |
| 2017/0258719 A1 | 9/2017 | MacLachlan et al. |
| 2017/0260523 A1 | 9/2017 | Yaworski et al. |
| 2019/0032051 A1 | 1/2019 | Yaworski et al. |

FOREIGN PATENT DOCUMENTS

| | | | |
|---|---|---|---|
| WO | 2011084518 A2 | 7/2011 | |
| WO | 2012044638 A1 | 4/2012 | |
| WO | 2012170930 A1 | 12/2012 | |
| WO | 2013064911 A2 | 5/2013 | |
| WO | 2013126803 A1 | 8/2013 | |
| WO | 2013149140 A1 | 10/2013 | |
| WO | WO 2013/158579 A1 * | 10/2013 | ........... C12N 15/113 |
| WO | 2013185069 A1 | 12/2013 | |
| WO | 2014089486 A1 | 6/2014 | |
| WO | 2015011633 A1 | 1/2015 | |
| WO | 2016090262 A1 | 6/2016 | |

OTHER PUBLICATIONS

Pardi, N., et al., "Expression kinetics of nucleoside-modified mRNA delivered in lipid nanoparticles to mice by various routes", Journal of Controlled Release 217, 345-351 (2015).

Patent Cooperation Treaty, International Searching Authority, Search Report and Written Opinion for PCT/2017/040446, 13 pages, dated Sep. 7, 2017.

Reichmuth, A, et al., "mRNA vaccine delivery using lipid nanoparticles", Therapeutic Delivery 7(5), 319-334 (2016).

Yamada, Y, et al., "Post-nuclear gene delivery events for transgene expression by biocleavable polyrotaxanes", Biomaterials 33(15), 3952-3958 (2012).

Kar, S, et al., "Oxidized phospholipid content destabilizes the structure of reconstituted high density lipoprotein particles and changes their function", Biochimica et Biophysica Acta 1821, 1200-1210 (2012).

Li, J, et al., "Recent Advances in Delivery of Drug-Nucleic Acid Combinations for Cancer Treatment", J Control Release 172(2); DOI:10.1016/J.JCONNEL.2013.04.010 (2013).

* cited by examiner

COMPOSITIONS AND METHODS FOR DELIVERING MESSENGER RNA

CROSS-REFERENCE TO RELATED APPLICATIONS

This patent application claims the benefit of priority of U.S. application Ser. No. 62/357,189, filed Jun. 30, 2016, and of U.S. application Ser. No. 62/375,292, filed Aug. 15, 2016, which applications are herein incorporated by reference.

BACKGROUND

Some diseases in humans are caused by the absence, or impairment, of a functional protein in a cell type where the protein is normally present and active. The functional protein can be completely or partially absent due, for example, to transcriptional inactivity of the encoding gene, or due to the presence of a mutation in the encoding gene that renders the protein completely or partially non-functional.

Examples of human diseases that are caused by complete or partial inactivation of a protein include X-linked severe combined immunodeficiency (X-SCID), and adrenoleukodystrophy (X-ALD). X-SCID is caused by one or more mutations in the gene encoding the common gamma chain protein that is a component of the receptors for several interleukins that are involved in the development and maturation of B and T cells within the immune system. X-ALD is caused by one or more mutations in a peroxisomal membrane transporter protein gene called ABCD1. Individuals afflicted with X-ALD have very high levels of long chain fatty acids in tissues throughout the body, which causes a variety of symptoms that may lead to mental impairment or death.

Attempts have been made to use gene therapy to treat some diseases caused by the absence, or impairment, of a functional protein in a cell type where the protein is normally present and active. Gene therapy typically involves introduction of a vector that includes a gene encoding a functional form of the affected protein, into a diseased person, and expression of the functional protein to treat the disease. Thus far, gene therapy has met with limited success.

As such, there is a continuing need for compositions and methods for expressing a functional form of a protein within a human who suffers from a disease caused by the complete or partial absence of the functional protein, and there is a need for delivery of nucleic acids (e.g., mRNA) via a methods and compositions that trigger less of an immune response to the therapy.

BRIEF SUMMARY

In accordance with the foregoing, the present invention provides in certain embodiments compositions and methods that can be used to deliver nucleic acids, e.g., so as to express one or more mRNA molecules in a living cell (e.g., cells within a human body). The mRNA molecules can encode one or more polypeptides that is/are expressed within the living cells. In some embodiments, the polypeptides are expressed within a diseased organism (e.g., mammal, such as a human being), and expression of the polypeptide ameliorates one or more symptoms of the disease. The compositions and methods of certain embodiments of the invention are particularly useful for treating human diseases caused by the absence, or reduced levels, of a functional polypeptide within the human body.

In one aspect, the present invention provides a lipid nanoparticle (LNP) comprising: (a) a cationic lipid; (b) a non-cationic lipid; (c) a corticosteroid and; (d) a nucleic acid, wherein the nucleic acid and the corticosteroid are encapsulated within the lipid nanoparticle. Certain embodiments of the invention provide a population of lipid nanoparticles comprising the lipid nanoparticles. Certain embodiments of the invention provide a population of lipid particles comprising a multiplicity of lipid nanoparticles. In certain embodiments, the nucleic acid is HPLC-purified mRNA. In certain embodiments, the LNP comprises a PEG-lipid conjugate present in an amount of at least 3 mole percent. In certain embodiments, the LNP comprises less than 0.5 mole percent phospholipid.

Certain embodiments of the invention provide a population of lipid nanoparticles, comprising at least one population of lipid nanoparticle selected from: (a) a first population of lipid nanoparticles that each comprise a cationic lipid, a non-cationic lipid, and a corticosteroid; and (b) a second population of lipid nanoparticles that each comprise a cationic lipid, a non-cationic lipid, and a nucleic acid, wherein the first population of lipid nanoparticles does not comprise a nucleic acid, and wherein the second population of lipid nanoparticles does not comprise a corticosteroid. Certain embodiments of the invention provide a population of lipid nanoparticles comprising the first and second populations of lipid nanoparticles. In certain embodiments, the nucleic acid is HPLC-purified mRNA.

Certain embodiments of the invention provide a lipid nanoparticle comprising: (a) a cationic lipid; (b) a PEG-lipid conjugate present in an amount of at least 3 mole percent; and (c) mRNA encapsulated within the lipid particle; provided that the lipid particle comprises less than 0.5 mole percent phospholipid. In certain embodiments, the LNP comprises a corticosteroid. In certain embodiments, the mRNA is HPLC-purified mRNA.

Certain embodiments provide a population of lipid nanoparticles wherein each lipid nanoparticle in the population comprises: (a) a cationic lipid; (b) a PEG-lipid conjugate present in an amount of at least 3 mole percent; and (c) mRNA encapsulated within the lipid nanoparticle; provided that the lipid nanoparticle comprises less than 0.5 mole percent phospholipid. In certain embodiments, the population of LNPs comprises LNPs that comprise a corticosteroid. In certain embodiments, the mRNA is HPLC-purified mRNA.

Certain embodiments of the invention provide a lipid nanoparticle formulation comprising a multiplicity of lipid nanoparticles, wherein each lipid nanoparticle comprises: (a) a cationic lipid; (b) a non-cationic lipid; and (c) mRNA encapsulated within the lipid particle, wherein the lipid nanoparticle formulation has an IFIT response that is no more than 30 fold greater than a reference IFIT response of phosphate buffered saline. In certain embodiments, the mRNA is HPLC-purified mRNA. In certain embodiments, the LNP comprises a PEG-lipid conjugate present in an amount of at least 3 mole percent. In certain embodiments, the LNP comprises less than 0.5 mole percent phospholipid. In certain embodiments, the LNP comprises a corticosteroid.

Certain embodiments of the invention provide a method of making a lipid nanoparticle, comprising combining: (a) a cationic lipid; (b) a non-cationic lipid; and (c) purified mRNA so as to form a lipid nanoparticle, wherein the mRNA is encapsulated within the lipid nanoparticle, and wherein the lipid nanoparticle has an IFIT response that is no more than 30 fold greater than a reference IFIT response of phosphate buffered saline. In certain embodiments, the mRNA is HPLC-purified mRNA. In certain embodiments, the LNP comprises a PEG-lipid conjugate present in an amount of at least 3 mole percent. In certain embodiments, the LNP comprises less than 0.5 mole percent phospholipid. In certain embodiments, the LNP comprises a corticosteroid.

Certain embodiments of the invention provide a method of making a lipid nanoparticle formulation comprising a multiplicity of lipid nanoparticles, the method comprising the step of combining: (a) a cationic lipid; (b) a non-cationic lipid; and (c) purified mRNA so as to form a lipid nanoparticle formulation comprising a multiplicity of lipid nanoparticles, wherein the mRNA is encapsulated within the lipid particles in the lipid nanoparticle formulation, and wherein the lipid nanoparticle formulation has an IFIT response that is no more than 30 fold greater than a reference IFIT response of phosphate buffered saline. In certain embodiments, the LNP comprises a PEG-lipid conjugate present in an amount of at least 3 mole percent. In certain embodiments, the LNP comprises less than 0.5 mole percent phospholipid. In certain embodiments, the LNP comprises a corticosteroid.

Certain embodiments of the invention provide a lipid nanoparticle formulation comprising a multiplicity of lipid nanoparticles made by a process comprising the steps of combining: (a) a cationic lipid; (b) a non-cationic lipid; and (c) purified mRNA so as to form a lipid nanoparticle formulation comprising a multiplicity of lipid nanoparticles, wherein the mRNA is encapsulated within the lipid particles in the lipid nanoparticle formulation, and wherein the lipid nanoparticle formulation has an IFIT response that is no more than 30 fold greater than a reference IFIT response of phosphate buffered saline. In certain embodiments, the LNP comprises a PEG-lipid conjugate present in an amount of at least 3 mole percent. In certain embodiments, the LNP comprises less than 0.5 mole percent phospholipid. In certain embodiments, the LNP comprises a corticosteroid.

Thus, in one aspect, the present invention provides a lipid particle comprising a cationic lipid, a non-cationic lipid, and an mRNA molecule that is encapsulated within the lipid particle.

The present invention also provides nucleic acid-lipid particles that each include (a) a lipid particle comprising a cationic lipid, a PEG-lipid, and a phospholipid; and (b) an mRNA molecule, wherein the mRNA molecule is encapsulated within the lipid particle. The lipid particles can optionally include cholesterol. The mRNA can be completely or partially encapsulated within the lipid particle. In some embodiments, the nucleic acid-lipid particle has a lipid:mRNA mass ratio of from about 9:1 to about 20:1. In a specific embodiment, the nucleic acid-lipid particle has a lipid:mRNA mass ratio of about 12:1. The mRNA can be chemically modified, such as by the incorporation of pseudouridine instead of uridine, and/or the incorporation of 5-methylcytidine instead of cytidine. The present invention also provides pharmaceutical compositions that include nucleic acid-lipid particles of the present invention. Typically, the pharmaceutical compositions include an excipient.

In another aspect, the present invention provides methods for introducing an mRNA that encodes a protein into a cell. The methods each include the step of contacting the cell with a nucleic acid-lipid particle of the present invention (typically, a multiplicity of nucleic acid-lipid particles of the present invention) under conditions whereby the mRNA is introduced into the cell and expressed therein to produce the protein. The methods can be practiced in vivo or in vitro. For example, the cell is within a living body (e.g., a mammalian body, such as a human body), and the nucleic acid-lipid particle can be introduced into the living body by injection.

In a further aspect, the present invention provides methods for treating and/or ameliorating one or more symptoms associated with a disease, in a human, caused by impaired expression of a protein in the human. The methods of this aspect of the invention include the step of administering to the human a therapeutically effective amount of a nucleic acid-lipid particle of the present invention (typically, a multiplicity of nucleic acid-lipid particles of the present invention), wherein the mRNA encapsulated within the nucleic acid-lipid particle encodes the protein. The encoded protein is expressed within the human being, thereby ameliorating at least one symptom of the disease.

In one embodiment, the ratio of lipid to nucleic acid (e.g., mRNA) in the lipid particles used in the practice of the present invention is about 13:1.

The methods and compositions of the invention can be used, for example, to treat any disease that is caused, at least in part, by the absence of a polypeptide, or the reduced level of a polypeptide, or the expression of a non-functional (or partially functional, or aberrantly functional) form of a polypeptide, in a cell, tissue, and/or organ of a human body.

Other objects, features, and advantages of the present invention will be apparent to one of skill in the art from the following detailed description and figures.

DETAILED DESCRIPTION

The nucleic acid-lipid particles, methods, and pharmaceutical formulations, described herein advantageously provide significant new compositions and methods for expressing proteins in a mammalian organism, such as a human being. Embodiments of the present invention can be administered, for example, once per day, once per week, or once every several weeks (e.g., once every two, three, four, five or six weeks), or once per month, or once per year. Encapsulation of mRNA within lipid particles confers one or more advantages, such as protecting the mRNA from nuclease degradation in the bloodstream, allowing preferential accumulation of the mRNA in target tissue and providing a means of mRNA entry into the cellular cytoplasm where the mRNA can express the encoded protein.

In one aspect, the present invention provides a lipid nanoparticle comprising: (a) a cationic lipid; (b) a non-cationic lipid; (c) a corticosteroid and; (d) a nucleic acid, wherein the nucleic acid and the corticosteroid are encapsulated within the lipid nanoparticle. Certain embodiments of the invention provide a population of lipid nanoparticles comprising the lipid nanoparticles. Certain embodiments of the invention provide a population of lipid particles comprising a multiplicity of lipid nanoparticles. In certain embodiments, the nucleic acid is HPLC-purified mRNA. In certain embodiments, the LNP comprises a PEG-lipid conjugate present in an amount of at least 3 mole percent. In certain embodiments, the LNP comprises less than 0.5 mole percent phospholipid.

Certain embodiments of the invention provide a population of lipid nanoparticles, comprising at least one population of lipid nanoparticles selected from: (a) a first population of lipid nanoparticles that each comprise a cationic lipid, a non-cationic lipid, and a corticosteroid; and (b) a second population of lipid nanoparticles that each comprise a cationic lipid, a non-cationic lipid, and a nucleic acid, wherein the first population of lipid nanoparticles does not comprise a nucleic acid, and wherein the second population of lipid nanoparticles does not comprise a corticosteroid.

Certain embodiments of the invention provide a population of lipid nanoparticles comprising the first and second populations of lipid nanoparticles. In certain embodiments, the nucleic acid is HPLC-purified mRNA.

Certain embodiments of the invention provide a lipid nanoparticle comprising: (a) a cationic lipid; (b) a PEG-lipid conjugate present in an amount of at least 3 mole percent; and (c) mRNA encapsulated within the lipid particle; provided that the lipid particle comprises less than 0.5 mole percent phospholipid. In certain embodiments, the LNP comprises a corticosteroid. In certain embodiments, the mRNA is HPLC-purified mRNA.

Certain embodiments provide a population of lipid nanoparticles wherein each lipid nanoparticle in the population comprises: (a) a cationic lipid; (b) a PEG-lipid conjugate present in an amount of at least 3 mole percent; and (c) mRNA encapsulated within the lipid nanoparticle; provided that the lipid nanoparticle comprises less than 0.5 mole percent phospholipid. In certain embodiments, the population of LNPs comprises LNPs that comprise a corticosteroid. In certain embodiments, the mRNA is HPLC-purified mRNA.

Certain embodiments of the invention provide a lipid nanoparticle formulation comprising a multiplicity of lipid nanoparticles, wherein each lipid nanoparticle comprises: (a) a cationic lipid; (b) a non-cationic lipid; and (c) mRNA encapsulated within the lipid particle, wherein the lipid nanoparticle formulation has an IFIT response that is no more than 30 fold greater than a reference IFIT response of phosphate buffered saline. In certain embodiments, the mRNA is purified mRNA. In certain embodiments, the mRNA is HPLC-purified mRNA. In certain embodiments, the LNP comprises a PEG-lipid conjugate present in an amount of at least 3 mole percent. In certain embodiments, the LNP comprises a PEG-lipid conjugate present in an amount of at least 3.5 mole percent. In certain embodiments, the LNP comprises less than 0.5 mole percent phospholipid. In certain embodiments, the LNP comprises less than 0.05 mole percent phospholipid. In certain embodiments, the LNP comprises a corticosteroid. In certain embodiments, substantially all of the lipid nanoparticles in the formulation comprise a corticosteroid encapsulated within the lipid nanoparticle. For example, in certain embodiments, at least about 80% of the lipid nanoparticles in the formulation further comprise a corticosteroid encapsulated within the lipid nanoparticle. In certain embodiments, at least about 81%, 82%, 83%, 84%, 85%, 86%, 87%, 88%, 89%, 90%, 91%, 92%, 93%, 94%, 95%, 96%, 97%, 98%, 99% or 100% of the lipid nanoparticles in the formulation further comprise a corticosteroid encapsulated within the lipid nanoparticle.

Certain embodiments of the invention provide a lipid nanoparticle formulation comprising a multiplicity of lipid nanoparticles, wherein each lipid nanoparticle comprises: (a) a cationic lipid; (b) a non-cationic lipid; and (c) mRNA encapsulated within the lipid particle, wherein the lipid nanoparticle formulation has an IFIT response that is no more than 30 fold greater than a reference IFIT response of phosphate buffered saline, wherein the non-cationic lipid is a PEG-lipid conjugate present in an amount of at least 3 mole percent, provided that the lipid nanoparticle comprises less than 0.5 mole percent phospholipid, and wherein at least 90% of the lipid nanoparticles in the formulation further comprise a corticosteroid encapsulated within the lipid nanoparticle.

Certain embodiments of the invention provide a lipid nanoparticle formulation comprising:
(a) a first population of lipid nanoparticles that each comprise a cationic lipid, a non-cationic lipid, and a corticosteroid encapsulated with the lipid nanoparticle; and
(b) a second population of lipid nanoparticles that each comprise a cationic lipid, a non-cationic lipid, and a mRNA encapsulated within the lipid nanoparticle,
wherein the first population of lipid nanoparticles does not comprise a mRNA, wherein the second population of lipid nanoparticles does not comprise a corticosteroid, and wherein the lipid nanoparticle formulation has an IFIT response that is no more than 30 fold greater than a reference IFIT response of phosphate buffered saline.

Certain embodiments of the invention provide a method of making a lipid nanoparticle, comprising combining: (a) a cationic lipid; (b) a non-cationic lipid; and (c) purified mRNA so as to form a lipid nanoparticle, wherein the mRNA is encapsulated within the lipid nanoparticle, and wherein the lipid nanoparticle has an IFIT response that is no more than 30 fold greater than a reference IFIT response of phosphate buffered saline. In certain embodiments, the mRNA is HPLC-purified mRNA. In certain embodiments, the LNP comprises a PEG-lipid conjugate present in an amount of at least 3 mole percent. In certain embodiments, the LNP comprises less than 0.5 mole percent phospholipid. In certain embodiments, the LNP comprises a corticosteroid. In certain embodiments, the method further comprises purifying mRNA to provide the purified mRNA.

Certain embodiments of the invention provide a method of making a lipid nanoparticle formulation comprising a multiplicity of lipid nanoparticles, the method comprising the step of combining: (a) a cationic lipid; (b) a non-cationic lipid; and (c) purified mRNA so as to form a lipid nanoparticle formulation comprising a multiplicity of lipid nanoparticles, wherein the mRNA is encapsulated within the lipid particles in the lipid nanoparticle formulation, and wherein the lipid nanoparticle formulation has an IFIT response that is no more than 30 fold greater than a reference IFIT response of phosphate buffered saline. In certain embodiments, the LNP comprises a PEG-lipid conjugate present in an amount of at least 3 mole percent. In certain embodiments, the LNP comprises less than 0.5 mole percent phospholipid. In certain embodiments, the LNP comprises a corticosteroid. In certain embodiments, the method further comprises purifying mRNA (e.g., via HPLC) to provide the purified mRNA.

Certain embodiments of the invention provide a lipid nanoparticle formulation comprising a multiplicity of lipid nanoparticles made by a process comprising the steps of combining: (a) a cationic lipid; (b) a non-cationic lipid; and (c) purified mRNA so as to form a lipid nanoparticle formulation comprising a multiplicity of lipid nanoparticles, wherein the mRNA is encapsulated within the lipid particles in the lipid nanoparticle formulation, and wherein the lipid nanoparticle formulation has an IFIT response that is no more than 30 fold greater than a reference IFIT response of phosphate buffered saline. In certain embodiments, the LNP comprises a PEG-lipid conjugate present in an amount of at least 3 mole percent. In certain embodiments, the LNP comprises less than 0.5 mole percent phospholipid. In certain embodiments, the LNP comprises a corticosteroid. In certain embodiments, the method further comprises purifying mRNA (e.g., via HPLC) to provide the purified mRNA.

In certain embodiments, the nucleic acid is mRNA.

In certain embodiments, the nucleic acid is purified mRNA.

In certain embodiments, the mRNA is HPLC-purified mRNA.

In certain embodiments, the corticosteroid has a log P greater than 3.0.

In certain embodiments, substantially all lipid nanoparticles in a formulation/population comprise a corticosteroid encapsulated within the lipid nanoparticle. For example, in certain embodiments, at least about 80% of the lipid nanoparticles in a formulation/population further comprise a corticosteroid encapsulated within the lipid nanoparticle. In certain embodiments, at least about 81%, 82%, 83%, 84%, 85%, 86%, 87%, 88%, 89%, 90%, 91%, 92%, 93%, 94%, 95%, 96%, 97%, 98%, 99% or 100% of the lipid nanoparticles in the formulation/population further comprise a corticosteroid encapsulated within the lipid nanoparticle.

In certain embodiments, the corticosteroid is a glucocorticoid.

In certain embodiments, the corticosteroid is a mineralocorticoid.

In certain embodiments, the corticosteroid is clobetasol.

In certain embodiments, the glucocorticoid is selected from hydrocortisone, cortisone, corticosterone, deoxycorticosterone, prednisone, prednisolone, methylprednisolone, dexamethasone, betamethasone, mometasone, triamcinolone, beclomethasone, fludrocortisone, aldosterone, fluticasone, clobetasone, clobetasol, and loteprednol, and pharmaceutically acceptable salts thereof, and mixtures thereof.

In certain embodiments, the non-cationic lipid is selected from a PEG-lipid conjugate and a phospholipid.

In certain embodiments, the non-cationic lipid is selected from a PEG-lipid conjugate, a phospholipid, or a mixture of a PEG-lipid conjugate and a phospholipid.

In certain embodiments, the non-cationic lipid comprises a phospholipid.

In certain embodiments, the non-cationic lipid comprises a PEG-lipid conjugate.

In certain embodiments, the non-cationic lipid comprises a mixture of a PEG-lipid conjugate and a phospholipid.

In certain embodiments, the non-cationic lipid is a phospholipid.

In certain embodiments, the non-cationic lipid is a PEG-lipid conjugate.

In certain embodiments, the non-cationic lipid is a mixture of a PEG-lipid conjugate and a phospholipid.

In certain embodiments, the lipid nanoparticle further comprises cholesterol.

In certain embodiments, the phospholipid comprises dipalmitoylphosphatidylcholine (DPPC), distearoylphosphatidylcholine (DSPC), or a mixture thereof.

In certain embodiments, the PEG-lipid conjugate is selected from the group consisting of a PEG-diacylglycerol (PEG-DAG) conjugate, a PEG-dialkyloxypropyl (PEG-DAA) conjugate, a PEG-phospholipid conjugate, a PEG-ceramide (PEG-Cer) conjugate, and a mixture thereof.

In certain embodiments, the PEG-lipid conjugate is selected from the group consisting of a PEG-2000-C-DMA, PEG-diacylglycerol (PEG-DAG) conjugate, a PEG-dialkyloxypropyl (PEG-DAA) conjugate, a PEG-phospholipid conjugate, a PEG-ceramide (PEG-Cer) conjugate, and a mixture thereof.

In certain embodiments, the PEG-lipid conjugate is a PEG-DAA conjugate.

In certain embodiments, the PEG-DAA conjugate is selected from the group consisting of a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, and a mixture thereof.

In certain embodiments, the lipid nanoparticle has a lipid:nucleic mass ratio of from about 9:1 to about 20:1.

In certain embodiments, the multiplicity of lipid nanoparticles in the lipid nanoparticle formulation has a lipid:nucleic mass ratio of from about 9:1 to about 20:1.

In certain embodiments, the mRNA is chemically modified.

In certain embodiments, the lipid nanoparticle comprises an electron dense core.

In certain embodiments, the lipid nanoparticle comprises an electron dense core and wherein the mRNA is located within the electron dense core.

Certain embodiments provide a pharmaceutical composition comprising a lipid nanoparticle or population thereof as described herein, and a pharmaceutically acceptable carrier.

Certain embodiments provide a method for introducing an mRNA that encodes a protein into a cell, the method comprising contacting the cell with a lipid nanoparticle or population thereof as described herein, under conditions whereby the mRNA is introduced into the cell and expressed therein to produce the protein.

Certain embodiments provide a method for treating and/or ameliorating one or more symptoms associated with a disease in a human, caused by impaired expression of a protein in the human, the method comprising administering to the human a therapeutically effective amount of a lipid nanoparticle or population thereof as described herein, wherein the mRNA encapsulated within the lipid nanoparticle encodes the protein.

In certain embodiments, the phospholipid is distearoylphosphatidylcholine (DSPC).

In certain embodiments, the PEG-lipid conjugate is PEG-2000-C-DMA.

In certain embodiments, the LNP comprises at least 3.5 mole percent of the PEG-lipid conjugate (e.g., at least about 3.5, 4, 4.5, 5, 5.5, or 6 mole percent).

In certain embodiments, the amount of PEG-lipid conjugate is at least 3 mole percent (e.g., at least 3.1 mole percent, at least 3.2 mole percent, at least 3.3 mole percent, at least 3.4 mole percent, at least 3.5 mole percent, at least 3.6 mole percent, at least 3.7 mole percent, at least 3.8 mole percent, at least 3.9 mole percent, at least 4 mole percent). With respect to phospholipid, in certain embodiments, no phospholipid is used in the practice of the invention. In certain embodiments, the lipid particle comprises less than 2 mole percent phospholipid, e.g., 1.9 mol % phospholipid, 1.8 mol % phospholipid, 1.7 mol % phospholipid, 1.6 mol % phospholipid, 1.5 mol % phospholipid, 1.4 mol % phospholipid, 1.3 mol % phospholipid, 1.2 mol % phospholipid, 1.1 mol % phospholipid, 1.0 mol % phospholipid, 0.9 mol % phospholipid, 0.8 mol % phospholipid, 0.7 mol % phospholipid, 0.6 mol % phospholipid, 0.5 mol % phospholipid, 0.4 mol % phospholipid, 0.3 mol % phospholipid, 0.2 mol % phospholipid, 0.1 mol % phospholipid, or 0.0% phospholipid, e.g., less than 1.9 mol % phospholipid, less than 1.8 mol % phospholipid, less than 1.7 mol % phospholipid, less than 1.6 mol % phospholipid, less than 1.5 mol % phospholipid, less than 1.4 mol % phospholipid, less than 1.3 mol % phospholipid, less than 1.2 mol % phospholipid, less than 1.1 mol % phospholipid, less than 1.0 mol % phospholipid, less than 0.9 mol % phospholipid, less than 0.8 mol % phospholipid, less than 0.7 mol % phospholipid, less than 0.6 mol % phospholipid, less than 0.5 mol % phospholipid, less than 0.4 mol % phospholipid, less than 0.3 mol % phospholipid, less than 0.2 mol % phospholipid, less than 0.1 mol % phospholipid.

In certain embodiments, the LNP comprises a PEG-lipid conjugate present in an amount of at least 3 mole percent, provided that the LNP comprises less than 0.5 mole percent phospholipid. In certain embodiments, the PEG-lipid conjugate is present in an amount of at least 3.5 mole percent (e.g., at least about 3.5, 4, 4.5, 5, 5.5, or 6 mole percent). In certain embodiments, the LNP comprises less than 0.05 mole percent phospholipid.

In certain embodiments, the lipid nanoparticle has a lipid:mRNA mass ratio of from about 9:1 to about 20:1.

Certain embodiments provide a lipid nanoparticle prepared according to the methods described herein.

Certain embodiments provide a lipid nanoparticle formulation comprising a multiplicity of lipid nanoparticles as described herein.

Certain embodiments provide a lipid nanoparticle formulation comprising a multiplicity of lipid nanoparticles as described herein, wherein the lipid nanoparticle formulation has an IFIT response that is no more than 30 fold greater than a phosphate buffered saline control response. In certain embodiments, the lipid nanoparticle formulation has an IFIT response that is no more than about 29, 28, 2, 26, 25, 24, 23, 22, 21, 20, 19, 18, 17, 16, 15, 14, 13, 12, 11, 10, 9, 8, 7, 6, 5, 4, 3, 2 or 1 fold greater than a phosphate buffered saline control response.

As used herein, the following terms have the meanings ascribed to them unless specified otherwise.

An "effective amount" or "therapeutically effective amount" of a therapeutic nucleic acid such as an mRNA is an amount sufficient to produce the desired effect, e.g., mRNA-directed expression of an amount of a protein that causes a desirable biological effect in the organism within which the protein is expressed. For example, in some embodiments, the expressed protein is an active form of a protein that is normally expressed in a cell type within the body, and the therapeutically effective amount of the mRNA is an amount that produces an amount of the encoded protein that is at least 50% (e.g., at least 60%, or at least 70%, or at least 80%, or at least 90%) of the amount of the protein that is normally expressed in the cell type of a healthy individual. Suitable assays for measuring the expression of an mRNA or protein include, but are not limited to dot blots, Northern blots, in situ hybridization, ELISA, immunoprecipitation, enzyme function, as well as phenotypic assays known to those of skill in the art.

By "decrease," "decreasing," "reduce," or "reducing" of an immune response by an mRNA is intended to mean a detectable decrease of an immune response to a given mRNA (e.g., a modified mRNA). The amount of decrease of an immune response by a modified mRNA may be determined relative to the level of an immune response in the presence of an unmodified mRNA. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified mRNA. A decrease in the immune response to mRNA is typically measured by a decrease in cytokine production (e.g., IFNγ, IFNα, TNFα, IL-6, or IL-12) by a responder cell in vitro or a decrease in cytokine production in the sera of a mammalian subject after administration of the mRNA.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec. to 2 min., an annealing phase lasting 30 sec. to 2 min., and an extension phase of about 72° C. for 1 to 2 min. Protocols and guidelines for low and high stringency amplification reactions are provided, e.g., in Innis et al., *PCR Protocols, A Guide to Methods and Applications*, Academic Press, Inc. N.Y. (1990).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, Ausubel et al., eds.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 55, or 60 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of a number of contiguous positions selected from the group consisting of from about 5 to about 60, usually about 10 to about 45, more usually about 15 to about 30, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Natl. Acad. Sci. USA*, 85:2444 (1988), by computerized implementations of these algorithms (GAP, BESALDHIT, FASTA, and ALDHASTA in the Wisconsin Genetics Software Package, Genetics Computer Group, 575 Science Dr., Madison, Wis.), or by manual alignment and visual inspection (see, e.g., *Current Protocols in Molecular Biology*, Ausubel et al., eds. (1995 supplement)).

Non-limiting examples of algorithms that are suitable for determining percent sequence identity and sequence similarity are the BLAST and BLAST 2.0 algorithms, which are described in Altschul et al., *Nuc. Acids Res.*, 25:3389-3402 (1977) and Altschul et al., *J. Mol. Biol.*, 215:403-410 (1990), respectively. BLAST and BLAST 2.0 are used, with the parameters described herein, to determine percent sequence identity for the nucleic acids of the invention. Software for performing BLAST analyses is publicly available through the National Center for Biotechnology Information (http://www.ncbi.nlm.nih.gov/). Another example is a global alignment algorithm for determining percent sequence identity such as the Needleman-Wunsch algorithm for aligning protein or nucleotide (e.g., RNA) sequences.

The BLAST algorithm also performs a statistical analysis of the similarity between two sequences (see, e.g., Karlin and Altschul, *Proc. Natl. Acad. Sci. USA*, 90:5873-5787 (1993)). One measure of similarity provided by the BLAST algorithm is the smallest sum probability (P(N)), which provides an indication of the probability by which a match between two nucleotide sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "nucleic acid" as used herein refers to a polymer containing at least two deoxyribonucleotides or ribonucleotides in either single- or double-stranded form and includes DNA and RNA. DNA may be in the form of, e.g., antisense molecules, plasmid DNA, pre-condensed DNA, a PCR product, vectors (e.g., P1, PAC, BAC, YAC, artificial chromosomes), expression cassettes, chimeric sequences, chromosomal DNA, or derivatives and combinations of these groups. RNA may be in the form of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Nucleic acid sequence may in certain embodiments include an "unlocked nucleobase analogue" (abbreviated as "UNA").

The term "unlocked nucleobase analogue" (abbreviated as "UNA") refers to an acyclic nucleobase in which the C2' and C3' atoms of the ribose ring are not covalently linked. The term "unlocked nucleobase analogue" includes nucleobase analogues having the following structure identified as Structure A:

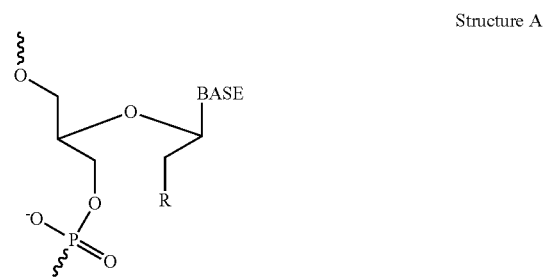

Structure A wherein R is hydroxyl, and Base is any natural or unnatural base such as, for example, adenine (A), cytosine (C), guanine (G) and thymine (T). UNA useful in the practice of the present invention include the molecules identified as acyclic 2'-3'-seco-nucleotide monomers in U.S. Pat. No. 8,314,227 which is incorporated by reference herein in its entirety.

Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260: 2605-2608 (1985); Rossolini et al., *Mol. Cell. Probes*, 8:91-98 (1994)).

The term "small-interfering RNA" or "siRNA" as used herein refers to double stranded RNA (i.e., duplex RNA) that is capable of reducing or inhibiting the expression of a target gene or sequence (e.g., by mediating the degradation or inhibiting the translation of mRNAs which are complementary to the siRNA sequence) when the siRNA is in the same cell as the target gene or sequence. The siRNA may have substantial or complete identity to the target gene or sequence, or may comprise a region of mismatch (i.e., a mismatch motif). In certain embodiments, the siRNAs may be about 19-25 (duplex) nucleotides in length, and is preferably about 20-24, 21-22, or 21-23 (duplex) nucleotides in length. siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand.

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *Proc. Natl. Acad. Sci. USA*, 99:9942-9947 (2002); Calegari et al., *Proc. Natl. Acad. Sci. USA*, 99:14236 (2002); Byrom et al., *Ambion TechNotes*, 10(1):4-6 (2003); Kawasaki et al., *Nucleic Acids Res.*, 31:981-987 (2003); Knight et al., *Science*, 293:2269-2271 (2001); and Robertson et al., *J. Biol. Chem.*, 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

"Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "lipid particle" includes a lipid formulation that can be used to deliver a therapeutic nucleic acid (e.g., mRNA or siRNA) to a target site of interest (e.g., cell, tissue, organ, and the like). In preferred embodiments, the lipid particle of the invention is a nucleic acid-lipid particle, which is typically formed from a cationic lipid, a non-cationic lipid (e.g., a phospholipid), a conjugated lipid that prevents aggregation of the particle (e.g., a PEG-lipid), and optionally cholesterol. Typically, the therapeutic nucleic acid (e.g., mRNA) may be encapsulated in the lipid portion of the particle, thereby protecting it from enzymatic degradation.

The term "electron dense core", when used to describe a lipid particle of the present invention, refers to the dark appearance of the interior portion of a lipid particle when visualized using cryo transmission electron microscopy ("cryoTEM"). Some lipid particles of the present invention have an electron dense core and lack a lipid bilayer structure. Some lipid particles of the present invention have an electron dense core, lack a lipid bilayer structure, and have an inverse Hexagonal or Cubic phase structure. While not wishing to be bound by theory, it is thought that the non-bilayer lipid packing provides a 3-dimensional network of lipid cylinders with water and nucleic on the inside, i.e., essentially, a lipid droplet interpenetrated with aqueous channels containing the nucleic acid.

As used herein, the term "SNALP" refers to a stable nucleic acid-lipid particle. A SNALP is a particle made from lipids (e.g., a cationic lipid, a non-cationic lipid, and a conjugated lipid that prevents aggregation of the particle), wherein the nucleic acid (e.g., mRNA) is fully encapsulated within the lipid. In certain instances, SNALP are extremely useful for systemic applications, as they can exhibit extended circulation lifetimes following intravenous (i.v.) injection, they can accumulate at distal sites (e.g., sites physically separated from the administration site), and they can mediate mRNA expression at these distal sites. The nucleic acid may be complexed with a condensing agent and encapsulated within a SNALP as set forth in PCT Publication No. WO 00/03683, the disclosure of which is herein incorporated by reference in its entirety for all purposes.

The lipid particles of the invention (e.g., SNALP) typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides a therapeutic nucleic acid such as an mRNA with full encapsulation, partial encapsulation, or both. In a preferred embodiment, the nucleic acid (e.g., mRNA) is fully encapsulated in the lipid particle (e.g., to form a SNALP or other nucleic acid-lipid particle).

The term "lipid conjugate" refers to a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates, polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used. The disclosures of each of the above patent documents are herein incorporated by reference in their entirety for all purposes.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the invention may also be termed titratable cationic lipids. In some embodiments, the cationic lipids comprise: a protonatable tertiary amine (e.g., pH-titratable) head group; $C_{18}$ alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DLinDMA, DLenDMA, γ-DLenDMA, DLin-K-DMA, DLin-K-C2-DMA (also known as DLin-C2K-DMA, XTC2, and C2K), DLin-K-C3-DMA, DLin-K-C4-DMA, DLen-C2K-DMA, γ-DLen-C2K-DMA, DLin-M-C2-DMA (also known as MC2), DLin-M-C3-DMA (also known as MC3) and (DLin-MP-DMA) (also known as 1-B11).

The term "alkylamino" includes a group of formula —N(H)R, wherein R is an alkyl as defined herein.

The term "dialkylamino" includes a group of formula —$NR_2$, wherein each R is independently an alkyl as defined herein.

The term "salts" includes any anionic and cationic complex, such as the complex formed between a cationic lipid and one or more anions. Non-limiting examples of anions include inorganic and organic anions, e.g., hydride, fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfate, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof. In particular embodiments, the salts of the cationic lipids disclosed herein are crystalline salts.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like.

The term "alkenyl" includes an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The term "acyl" includes any alkyl, alkenyl, or alkynyl wherein the carbon at the point of attachment is substituted with an oxo group, as defined below. The following are non-limiting examples of acyl groups: —C(=O)alkyl, —C(=O)alkenyl, and —C(=O)alkynyl.

The term "heterocycle" includes a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include, but are not limited to, heteroaryls as defined below, as well as morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" mean that, when substituted, at least one hydrogen atom is replaced with a substituent. In the case of an oxo substituent (=O), two hydrogen atoms are replaced. In this regard, substituents include, but are not limited to, oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$, wherein n is 0, 1, or 2, R$^x$ and R$^y$ are the same or different and are independently hydrogen, alkyl, or heterocycle, and each of the alkyl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, and —SO$_n$NR$^x$R$^y$. The term "optionally substituted," when used before a list of substituents, means that each of the substituents in the list may be optionally substituted as described herein.

The term "halogen" includes fluoro, chloro, bromo, and iodo.

The term "fusogenic" refers to the ability of a lipid particle, such as a SNALP, to fuse with the membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles such as SNALP means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent such as an mRNA within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent such as an mRNA directly to a target site within an organism. For example, an agent can be locally delivered by direct injection into a disease site, other target site, or a target organ such as the liver, heart, pancreas, kidney, and the like.

The term "mammal" refers to any mammalian species such as a human, mouse, rat, dog, cat, hamster, guinea pig, rabbit, livestock, and the like.

When used herein to describe the ratio of lipid:mRNA, the term "lipid" refers to the total lipid in the particle.

Unless stated otherwise herein, the term "about", when used in connection with a value or range of values, means plus or minus 5% of the stated value or range of values.

DESCRIPTION OF CERTAIN EMBODIMENTS

In one aspect, the present invention provides nucleic acid-lipid particles that each include (a) a lipid particle comprising a cationic lipid; and (b) an mRNA molecule encapsulated within the lipid particle. Typically, a population of mRNA molecules is encapsulated within the lipid particle. The lipid particles typically include an outer layer defining an interior portion, wherein the mRNA molecule(s) is located within the interior portion. The mRNA molecule(s) is typically completely encapsulated within the lipid particle. The lipid particles can be spherical or non-spherical. The lipid particles can have an electron dense core when visualized using cryo TEM. Typically, the electron dense core is mainly composed of lipid, although aqueous material may be present in an amount that is less than the amount of the lipid.

In one aspect, the present invention provides a lipid particle comprising a PEG lipid, a non-cationic lipid, a cationic lipid selected from a trialkyl cationic lipid and a tetra alkyl cationic lipid, and an mRNA; wherein the lipid particle has an electron dense core and the mRNA is encapsulated within the electron dense core.

In some embodiments of the invention the lipid particles include (a) a lipid particle comprising a cationic lipid, a PEG-lipid, and a phospholipid; and (b) an mRNA molecule, wherein the mRNA molecule is encapsulated within the lipid particle. The lipid particles can optionally include cholesterol. The mRNA can be completely or partially encapsulated within the lipid particle.

The formation of the particle 100 includes, in one or more embodiments, disposing a lipid into a first fluid, such as ethanol, disposing mRNA into a second fluid, such as an aqueous buffer, and mixing the first and second fluids under controlled conditions to form particle 100. The resulting particle 100 includes an electron dense core within the lipid particle when viewed by Cryo Transmission Electron Microscopy.

mRNA mRNA useful in the practice of the present invention may comprise at least one, two, three, four, five, six, seven, eight, nine, ten, or more modified nucleotides such as 2'OMe nucleotides. Preferably, uridine and/or guanosine nucleotides in the mRNA are modified with 2'OMe nucleotides. In some embodiments, the mRNA may further comprise modified (e.g., 2'OMe-modified) adenosine and/or modified (e.g., 2'OMe-modified) cytosine nucleotides.

In one aspect, the present invention provides a nucleic acid-lipid particle (e.g., SNALP) that includes an mRNA. The nucleic acid-lipid particles (e.g., SNALP) typically comprise one or more (e.g., a cocktail) mRNA(s), a cationic lipid, and a non-cationic lipid. In certain instances, the nucleic acid-lipid particles (e.g., SNALP) further comprise a conjugated lipid that inhibits aggregation of particles. Preferably, the nucleic acid-lipid particles (e.g., SNALP) comprise one or more (e.g., a cocktail) mRNAs, a cationic lipid, a non-cationic lipid, and a conjugated lipid that inhibits aggregation of particles.

In some embodiments, the mRNA(s) are fully encapsulated in the nucleic acid-lipid particle (e.g., SNALP). With respect to formulations comprising an mRNA cocktail, the different types of mRNA species present in the cocktail (e.g., mRNA having different sequences) may be co-encapsulated in the same particle, or each type of mRNA species present in the cocktail may be encapsulated in a separate particle. The mRNA cocktail may be formulated in the particles described herein using a mixture of two or more individual mRNAs (each having a unique sequence) at identical, similar, or different concentrations or molar ratios. In one embodiment, a cocktail of mRNAs (corresponding to a plurality of mRNAs with different sequences) is formulated using identical, similar, or different concentrations or molar ratios of each mRNA species, and the different types of mRNAs are co-encapsulated in the same particle. In another embodiment, each type of mRNA species present in the cocktail is encapsulated in different particles at identical, similar, or different mRNA concentrations or molar ratios, and the particles thus formed (each containing a different mRNA payload) are administered separately (e.g., at different times in accordance with a therapeutic regimen), or are combined and administered together as a single unit dose (e.g., with a pharmaceutically acceptable carrier). The particles described herein are serum-stable, are resistant to nuclease degradation, and are substantially non-toxic to mammals such as humans.

The cationic lipid in the nucleic acid-lipid particles of the invention (e.g., SNALP) may comprise, e.g., one or more cationic lipids of Formula I-III described herein or any other cationic lipid species. In one particular embodiment, the cationic lipid is selected from the group consisting of 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), dilinoleylmethyl-3-dimethylaminopropionate (DLin-M-C2-DMA), (6Z,9Z,28Z,31Z)-heptatriaconta-6,9,28,31-tetraen-19-yl 4-(dimethylamino)butanoate (DLin-M-C3-DMA), salts thereof, and mixtures thereof.

The non-cationic lipid in the nucleic acid-lipid particles of the present invention (e.g., SNALP) may comprise, e.g., one or more anionic lipids and/or neutral lipids. In some embodiments, the non-cationic lipid comprises one of the following neutral lipid components: (1) a mixture of a phospholipid and cholesterol or a derivative thereof; (2) cholesterol or a derivative thereof; or (3) a phospholipid. In certain preferred embodiments, the phospholipid comprises dipalmitoylphosphatidylcholine (DPPC), distearoylphosphatidylcholine (DSPC), or a mixture thereof. In a particularly preferred embodiment, the non-cationic lipid is a mixture of DPPC and cholesterol.

The lipid conjugate in the nucleic acid-lipid particles of the invention (e.g., SNALP) inhibits aggregation of particles and may comprise, e.g., one or more of the lipid conjugates described herein. In one particular embodiment, the lipid conjugate comprises a PEG-lipid conjugate. Examples of PEG-lipid conjugates include, but are not limited to, PEG-DAG conjugates, PEG-DAA conjugates, and mixtures thereof. In certain embodiments, the PEG-DAA conjugate in the lipid particle may comprise a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, or mixtures thereof. In another embodiment, the lipid conjugate comprises a POZ-lipid conjugate such as a POZ-DAA conjugate.

In some embodiments, the present invention provides nucleic acid-lipid particles (e.g., SNALP) comprising: (a) one or more (e.g., a cocktail) mRNA molecule(s) that each encode a protein; (b) one or more cationic lipids or salts thereof comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

In one aspect of this embodiment, the nucleic acid-lipid particle comprises: (a) one or more (e.g., a cocktail) mRNA molecule(s) that each encode a protein; (b) a cationic lipid or a salt thereof comprising from about 52 mol % to about 62 mol % of the total lipid present in the particle; (c) a mixture of a phospholipid and cholesterol or a derivative thereof comprising from about 36 mol % to about 47 mol % of the total lipid present in the particle; and (d) a PEG-lipid conjugate comprising from about 1 mol % to about 2 mol % of the total lipid present in the particle. This embodiment of nucleic acid-lipid particle is generally referred to herein as the "1:57" formulation. In one particular embodiment, the 1:57 formulation is a four-component system comprising about 1.4 mol % PEG-lipid conjugate (e.g., PEG2000-C-DMA), about 57.1 mol % cationic lipid (e.g., DLin-K-C2-DMA) or a salt thereof, about 7.1 mol % DPPC (or DSPC), and about 34.3 mol % cholesterol (or derivative thereof).

In another aspect of this embodiment, the nucleic acid-lipid particle comprises: (a) one or more (e.g., a cocktail) mRNA molecule(s) that each encode a protein; (b) a cationic lipid or a salt thereof comprising from about 56.5 mol % to about 66.5 mol % of the total lipid present in the particle; (c) cholesterol or a derivative thereof comprising from about 31.5 mol % to about 42.5 mol % of the total lipid present in the particle; and (d) a PEG-lipid conjugate comprising from about 1 mol % to about 2 mol % of the total lipid present in the particle. This embodiment of nucleic acid-lipid particle is generally referred to herein as the "1:62" formulation. In one particular embodiment, the 1:62 formulation is a three-component system which is phospholipid-free and comprises about 1.5 mol % PEG-lipid conjugate (e.g., PEG2000-

C-DMA), about 61.5 mol % cationic lipid (e.g., DLin-K-C2-DMA) or a salt thereof, and about 36.9 mol % cholesterol (or derivative thereof).

Additional embodiments related to the 1:57 and 1:62 formulations are described in PCT Publication No. WO 09/127060 and published US patent application publication number US 2011/0071208 A1, the disclosures of which are herein incorporated by reference in their entirety for all purposes.

In other embodiments, the present invention provides nucleic acid-lipid particles (e.g., SNALP) comprising: (a) one or more (e.g., a cocktail) mRNA molecule(s) that each encode a protein; (b) one or more cationic lipids or salts thereof comprising from about 2 mol % to about 50 mol % of the total lipid present in the particle; (c) one or more non-cationic lipids comprising from about 5 mol % to about 90 mol % of the total lipid present in the particle; and (d) one or more conjugated lipids that inhibit aggregation of particles comprising from about 0.5 mol % to about 20 mol % of the total lipid present in the particle.

In one aspect of this embodiment, the nucleic acid-lipid particle comprises: (a) one or more (e.g., a cocktail) mRNA molecule(s) that each encode a protein; (b) a cationic lipid or a salt thereof comprising from about 30 mol % to about 50 mol % of the total lipid present in the particle; (c) a mixture of a phospholipid and cholesterol or a derivative thereof comprising from about 47 mol % to about 69 mol % of the total lipid present in the particle; and (d) a PEG-lipid conjugate comprising from about 1 mol % to about 3 mol % of the total lipid present in the particle. This embodiment of nucleic acid-lipid particle is generally referred to herein as the "2:40" formulation. In one particular embodiment, the 2:40 formulation is a four-component system which comprises about 2 mol % PEG-lipid conjugate (e.g., PEG2000-C-DMA), about 40 mol % cationic lipid (e.g., DLin-K-C2-DMA) or a salt thereof, about 10 mol % DPPC (or DSPC), and about 48 mol % cholesterol (or derivative thereof).

In further embodiments, the present invention provides nucleic acid-lipid particles (e.g., SNALP) comprising: (a) one or more (e.g., a cocktail) mRNA molecule(s) that each encode a protein; (b) one or more cationic lipids or salts thereof comprising from about 50 mol % to about 65 mol % of the total lipid present in the particle; (c) one or more non-cationic lipids comprising from about 25 mol % to about 45 mol % of the total lipid present in the particle; and (d) one or more conjugated lipids that inhibit aggregation of particles comprising from about 5 mol % to about 10 mol % of the total lipid present in the particle.

In one aspect of this embodiment, the nucleic acid-lipid particle comprises: (a) one or more (e.g., a cocktail) mRNA molecule(s) that each encode a protein; (b) a cationic lipid or a salt thereof comprising from about 50 mol % to about 60 mol % of the total lipid present in the particle; (c) a mixture of a phospholipid and cholesterol or a derivative thereof comprising from about 35 mol % to about 45 mol % of the total lipid present in the particle; and (d) a PEG-lipid conjugate comprising from about 5 mol % to about 10 mol % of the total lipid present in the particle. This embodiment of nucleic acid-lipid particle is generally referred to herein as the "7:54" formulation. In certain instances, the non-cationic lipid mixture in the 7:54 formulation comprises: (i) a phospholipid of from about 5 mol % to about 10 mol % of the total lipid present in the particle; and (ii) cholesterol or a derivative thereof of from about 25 mol % to about 35 mol % of the total lipid present in the particle. In one particular embodiment, the 7:54 formulation is a four-component system which comprises about 7 mol % PEG-lipid conjugate (e.g., PEG750-C-DMA), about 54 mol % cationic lipid (e.g., DLin-K-C2-DMA) or a salt thereof, about 7 mol % DPPC (or DSPC), and about 32 mol % cholesterol (or derivative thereof).

In another aspect of this embodiment, the nucleic acid-lipid particle comprises: (a) one or more (e.g., a cocktail) mRNA molecule(s) that each encode a protein; (b) a cationic lipid or a salt thereof comprising from about 55 mol % to about 65 mol % of the total lipid present in the particle; (c) cholesterol or a derivative thereof comprising from about 30 mol % to about 40 mol % of the total lipid present in the particle; and (d) a PEG-lipid conjugate comprising from about 5 mol % to about 10 mol % of the total lipid present in the particle. This embodiment of nucleic acid-lipid particle is generally referred to herein as the "7:58" formulation. In one particular embodiment, the 7:58 formulation is a three-component system which is phospholipid-free and comprises about 7 mol % PEG-lipid conjugate (e.g., PEG750-C-DMA), about 58 mol % cationic lipid (e.g., DLin-K-C2-DMA) or a salt thereof, and about 35 mol % cholesterol (or derivative thereof).

Additional embodiments related to the 7:54 and 7:58 formulations are described in published US patent application publication number US 2011/0076335 A1, the disclosure of which is herein incorporated by reference in its entirety for all purposes.

The present invention also provides pharmaceutical compositions comprising a nucleic acid-lipid particle such as a SNALP and a pharmaceutically acceptable carrier.

The nucleic acid-lipid particles of the present invention (e.g., SNALP) are useful for the therapeutic delivery of mRNAs that express one or more proteins (such as full length proteins, or biologically active fragments of full length proteins). In some embodiments, a cocktail of mRNAs that express different proteins is formulated into the same or different nucleic acid-lipid particles, and the particles are administered to a mammal (e.g., a human) requiring such treatment. In certain instances, a therapeutically effective amount of the nucleic acid-lipid particles can be administered to the mammal.

In certain embodiments, the present invention provides a method for introducing one or more mRNA molecules into a cell by contacting the cell with a nucleic acid-lipid particle described herein (e.g., a SNALP formulation). In one particular embodiment, the cell is a reticuloendothelial cell (e.g., monocyte or macrophage), fibroblast cell, endothelial cell, or platelet cell.

In some embodiments, the nucleic acid-lipid particles described herein (e.g., SNALP) are administered by one of the following routes of administration: oral, intranasal, intravenous, intraperitoneal, intramuscular, intra-articular, intralesional, intratracheal, subcutaneous, and intradermal. In particular embodiments, the nucleic acid-lipid particles are administered systemically, e.g., via enteral or parenteral routes of administration.

In particular embodiments, the nucleic acid-lipid particles of the invention (e.g., SNALP) can preferentially deliver a payload such as an mRNA to the liver as compared to other tissues.

In certain aspects, the present invention provides methods for expressing a protein in a mammal (e.g., human) in need thereof, the method comprising administering to the mammal a therapeutically effective amount of a nucleic acid-lipid particle (e.g., a SNALP formulation) comprising one or more mRNAs that encode one or more proteins under conditions that enable expression of the protein(s) in the mammal. For example, in embodiments in which the mRNA encodes a protein that is normally expressed in a healthy mammalian subject, the level of expression of the protein encoded by the mRNA encapsulated within the SNALP is at least 10%, or at least 20%, or at least 30%, or at least 40%, or at least 50%, or at least 60%, or at least 70%, or at least 80%, or at least 90%, or at least 100%, or greater than 100%, of the level of the protein that is normally expressed in a healthy mammalian subject.

In other aspects, the present invention provides methods for treating, preventing, reducing the risk or likelihood of developing (e.g., reducing the susceptibility to), delaying the onset of, and/or ameliorating one or more symptoms associated with a disease in a mammal (e.g., human) in need thereof, wherein the disease is caused (at least in part) by reduced or aberrant expression of a protein. The methods each include the step of administering to the mammal a therapeutically effective amount of a nucleic acid-lipid particle (e.g., a SNALP formulation) comprising one or more mRNA molecules that encode a protein that is absent, or present at reduced levels, within the treated subject.

mRNA molecules useful in the present invention may be chemically modified or unmodified. Typically mRNA molecules are chemically modified in order to reduce their ability to induce the innate immune response of a cell into which the mRNA is introduced.

Modifications to mRNA mRNA used in the practice of the present invention can include one, two, or more than two nucleoside modifications. In some embodiments, the modified mRNA exhibits reduced degradation in a cell into which the mRNA is introduced, relative to a corresponding unmodified mRNA.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyl adenosine, N6-methyladenosine, N6-isopentenyladenosine, N6-(cis-hydroxyisopentenyl) adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In specific embodiments, a modified nucleoside is 5'-O-(1-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O-(1-Thiophosphate)-Pseudouridine. The α-thio substituted phosphate moiety is provided to confer stability to RNA polymers through the unnatural phosphorothioate backbone linkages. Phosphorothioate RNA have increased nuclease resistance and subsequently a longer half-life in a cellular environment. Phosphorothioate linked nucleic acids are expected to also reduce the innate immune response through weaker binding/activation of cellular innate immune molecules.

In certain embodiments it is desirable to intracellularly degrade a modified nucleic acid introduced into the cell, for example if precise timing of protein production is desired. Thus, the invention provides a modified nucleic acid containing a degradation domain, which is capable of being acted on in a directed manner within a cell.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

Optional Components of the Modified Nucleic Acids

In further embodiments, the modified nucleic acids may include other optional components, which can be beneficial in some embodiments. These optional components include, but are not limited to, untranslated regions, kozak sequences, intronic nucleotide sequences, internal ribosome entry site (IRES), caps and polyA tails. For example, a 5' untranslated region (UTR) and/or a 3' UTR may be provided, wherein either or both may independently contain one or more different nucleoside modifications. In such embodiments, nucleoside modifications may also be present in the translatable region. Also provided are nucleic acids containing a Kozak sequence.

Additionally, provided are nucleic acids containing one or more intronic nucleotide sequences capable of being excised from the nucleic acid.

Untranslated Regions (UTRs)

Untranslated regions (UTRs) of a gene are transcribed but not translated. The 5'UTR starts at the transcription start site and continues to the start codon but does not include the start codon; whereas, the 3'UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the mRNA used in the present invention to increase the stability of the molecule. The specific features can also be incorporated to ensure controlled down-regulation of the transcript in case they are misdirected to undesired organs sites.

5' Capping

The 5' cap structure of an mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns removal during mRNA splicing.

Endogenous mRNA molecules may be 5'-end capped generating a 5'-ppp-5'-triphosphate linkage between a terminal guanosine cap residue and the 5'-terminal transcribed sense nucleotide of the mRNA molecule. This 5'-guanylate cap may then be methylated to generate an N7-methylguanylate residue. The ribose sugars of the terminal and/or anteterminal transcribed nucleotides of the 5' end of the mRNA may optionally also be 2'-0-methylated. 5'-decapping through hydrolysis and cleavage of the guanylate cap structure may target a nucleic acid molecule, such as an mRNA molecule, for degradation.

IRES Sequences mRNA containing an internal ribosome entry site (IRES) are also useful in the practice of the present invention. An IRES may act as the sole ribosome binding site, or may serve as one of multiple ribosome binding sites of an mRNA. An mRNA containing more than one functional ribosome binding site may encode several peptides or polypeptides that are translated independently by the ribosomes ("multicistronic mRNA"). When mRNA are provided with an IRES, further optionally provided is a second translatable region. Examples of IRES sequences that can be used according to the invention include without limitation, those from picornaviruses (e.g. FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (S1V) or cricket paralysis viruses (CrPV).

Poly-A Tails

During RNA processing, a long chain of adenine nucleotides (poly-A tail) may be added to a polynucleotide such as an mRNA molecules in order to increase stability. Immediately after transcription, the 3' end of the transcript may be cleaved to free a 3' hydroxyl. Then poly-A polymerase adds a chain of adenine nucleotides to the RNA. The process, called polyadenylation, adds a poly-A tail that can be between 100 and 250 residues long.

Generally, the length of a poly-A tail is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1000, 1100, 1200, 1300, 1400, 1500, 1600, 1700, 1800, 1900, 2,000, 2,500, and 3,000 nucleotides).

In this context the poly-A tail may be 10, 20, 30, 40, 50, 60, 70, 80, 90, or 100% greater in length than the modified mRNA. The poly-A tail may also be designed as a fraction of modified nucleic acids to which it belongs. In this context, the poly-A tail may be 10, 20, 30, 40, 50, 60, 70, 80, or 90% or more of the total length of the modified mRNA or the total length of the modified mRNA minus the poly-A tail.

Generating mRNA Molecules

Methods for isolating RNA, synthesizing RNA, hybridizing nucleic acids, making and screening cDNA libraries, and performing PCR are well known in the art (see, e.g., Gubler and Hoffman, *Gene,* 25:263-269 (1983); Sambrook et al., *Molecular Cloning, A Laboratory Manual* (2nd ed. 1989)); as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Kriegler, *Gene Transfer and Expression: A Laboratory Manual* (1990); and *Current Protocols in Molecular Biology* (Ausubel et al., eds., 1994). The disclosures of these references are herein incorporated by reference in their entirety for all purposes.

Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. In some embodiments, siRNA may be produced enzymatically or by partial/total organic synthesis, and modified ribonucleotides can be introduced by in vitro enzymatic or organic synthesis. In certain instances, each strand is prepared chemically. Methods of synthesizing RNA molecules are known in the art, e.g., the chemical synthesis methods as described in Verma and Eckstein (1998) or as described herein.

Methods for isolating RNA, synthesizing RNA, hybridizing nucleic acids, making and screening cDNA libraries, and performing PCR are well known in the art (see, e.g., Gubler and Hoffman, *Gene,* 25:263-269 (1983); Sambrook et al., supra; Ausubel et al., supra), as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). The disclosures of these references are herein incorporated by reference in their entirety for all purposes.

Preferably, siRNA are chemically synthesized. The oligonucleotides that comprise the siRNA molecules of the invention can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Methods Mol. Bio.,* 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 µmol scale protocol. Alternatively, syntheses at the 0.2 µmol scale can be performed on a 96-well plate synthesizer from Protogene (Palo Alto, Calif.). However, a larger or smaller scale of synthesis is also within the scope of this invention. Suitable reagents for oligonucleotide synthesis, methods for RNA deprotection, and methods for RNA purification are known to those of skill in the art.

siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection.

Lipid Particles

In certain aspects, the present invention provides lipid particles comprising one or more therapeutic mRNA molecules encapsulated within the lipid particles.

In some embodiments, the mRNA is fully encapsulated within the lipid portion of the lipid particle such that the mRNA in the lipid particle is resistant in aqueous solution to nuclease degradation. In other embodiments, the lipid particles described herein are substantially non-toxic to mammals such as humans. The lipid particles of the invention typically have a mean diameter of from about 30 nm to about 150 nm, from about 40 nm to about 150 nm, from about 50 nm to about 150 nm, from about 60 nm to about 130 nm, from about 70 nm to about 110 nm, or from about 70 to about 90 nm. The lipid particles of the invention also typically have a lipid:mRNA ratio (mass/mass ratio) of from about 1:1 to about 100:1, from about 1:1 to about 50:1, from about 2:1 to about 25:1, from about 3:1 to about 20:1, from about 5:1 to about 15:1, or from about 5:1 to about 10:1, or from about 10:1 to about 14:1, or from about 9:1 to about 20:1. In one embodiment, the lipid particles of the invention have a lipid:mRNA ratio (mass/mass ratio) of about 12:1, such as 12:1. In another embodiment, the lipid particles of the invention have a lipid:mRNA ratio (mass/mass ratio) of about 13:1, such as 13:1.

In preferred embodiments, the lipid particles of the invention are serum-stable nucleic acid-lipid particles (SNALP) which comprise an mRNA, a cationic lipid (e.g., one or more cationic lipids of Formula I-III or salts thereof as set forth herein), a phospholipid, and a conjugated lipid that inhibits aggregation of the particles (e.g., one or more PEG-lipid conjugates). The lipid particles can also include cholesterol. The SNALP may comprise at least 1, 2, 3, 4, 5, 6, 7, 8, 9, 10, or more unmodified and/or modified mRNA that express one or more polypeptides. Nucleic acid-lipid particles and their method of preparation are described in, e.g., U.S. Pat. Nos. 5,753,613; 5,785,992; 5,705,385; 5,976,567; 5,981, 501; 6,110,745; and 6,320,017; and PCT Publication No. WO 96/40964, the disclosures of which are each herein incorporated by reference in their entirety for all purposes.

In the nucleic acid-lipid particles of the invention, the mRNA may be fully encapsulated within the lipid portion of the particle, thereby protecting the nucleic acid from nuclease degradation. In preferred embodiments, a SNALP comprising an mRNA is fully encapsulated within the lipid portion of the particle, thereby protecting the nucleic acid from nuclease degradation. In certain instances, the mRNA in the SNALP is not substantially degraded after exposure of the particle to a nuclease at 37° C. for at least about 20, 30, 45, or 60 minutes. In certain other instances, the mRNA in the SNALP is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the mRNA is complexed with the lipid portion of the particle. One of the benefits of the formulations of the present invention is that the nucleic acid-lipid particle compositions are substantially non-toxic to mammals such as humans.

The term "fully encapsulated" indicates that the nucleic acid (mRNA) in the nucleic acid-lipid particle is not significantly degraded after exposure to serum or a nuclease assay that would significantly degrade free RNA. In a fully encapsulated system, preferably less than about 25% of the nucleic acid in the particle is degraded in a treatment that would normally degrade 100% of free nucleic acid, more preferably less than about 10%, and most preferably less than about 5% of the nucleic acid in the particle is degraded. "Fully encapsulated" also indicates that the nucleic acid-lipid particles are serum-stable, that is, that they do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Specific dyes such as OliGreen® and RiboGreen® (Invitrogen Corp.; Carlsbad, Calif.) are available for the quantitative determination of plasmid DNA, single-stranded deoxyribonucleotides, and/or single- or double-stranded ribonucleotides. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_o-I)/I_o$, where I and $I_o$ refer to the fluorescence intensities before and after the addition of detergent (see, Wheeler et al., *Gene Ther.*, 6:271-281 (1999)).

In other embodiments, the present invention provides a nucleic acid-lipid particle (e.g., SNALP) composition comprising a plurality of nucleic acid-lipid particles.

In some instances, the SNALP composition comprises mRNA that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the mRNA encapsulated therein.

Depending on the intended use of the lipid particles of the invention, the proportions of the components can be varied and the delivery efficiency of a particular formulation can be measured using, e.g., an endosomal release parameter (ERP) assay.

Cationic Lipids

Any of a variety of cationic lipids or salts thereof may be used in the lipid particles of the present invention (e.g., SNALP), either alone or in combination with one or more other cationic lipid species or non-cationic lipid species. The cationic lipids include the (R) and/or (S) enantiomers thereof. Typically, the cationic lipids contain a portion (i.e. a hydrophobic moiety) that comprises unsaturated and/or saturated hydrocarbon chains.

In one aspect, cationic lipids of Formula I having the following structure are useful in the present invention:

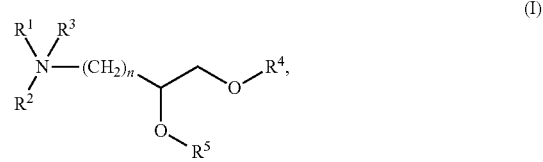
(I)

or salts thereof, wherein:

$R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof;

$R^3$ is either absent or is hydrogen (H) or a $C_1$-$C_6$ alkyl to provide a quaternary amine; $R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least two sites of unsaturation; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In one preferred embodiment, $R^1$ and $R^2$ are both methyl groups. In other preferred embodiments, n is 1 or 2. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, wherein at least one of $R^4$ and $R^5$ comprises at least two sites of unsaturation.

In certain embodiments, $R^4$ and $R^5$ are independently selected from the group consisting of a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, an arachidonyl moiety, and a docosahexaenoyl moiety, as well as acyl derivatives thereof (e.g., linoleoyl, linolenoyl, γ-linolenoyl, etc.). In some instances, one of $R^4$ and $R^5$ comprises a branched alkyl group (e.g., a phytanyl moiety) or an acyl derivative thereof (e.g., a phytanoyl moiety). In certain instances, the octadecadienyl moiety is a linoleyl moiety. In certain other instances, the octadecatrienyl moiety is a linolenyl moiety or a γ-linolenyl moiety. In certain embodiments, $R^4$ and $R^5$ are both linoleyl moieties, linolenyl moieties, or γ-linolenyl moieties. In particular embodiments, the cationic lipid of Formula I is 1,2-dilinoleyloxy-N,N-dimethylaminopropane (DLinDMA), 1,2-dilinolenyloxy-N,N-dimethylaminopropane (DLenDMA), 1,2-dilinoleyloxy-(N,N-dimethyl)-butyl-4-amine (C2-DLinDMA), 1,2-dilinoleoyloxy-(N,N-dimethyl)-butyl-4-amine (C2-DLinDAP), or mixtures thereof.

In some embodiments, the cationic lipid of Formula I forms a salt (preferably a crystalline salt) with one or more anions. In one particular embodiment, the cationic lipid of Formula I is the oxalate (e.g., hemioxalate) salt thereof, which is preferably a crystalline salt.

The synthesis of cationic lipids such as DLinDMA and DLenDMA, as well as additional cationic lipids, is described in U.S. Patent Publication No. 20060083780, the disclosure of which is herein incorporated by reference in its entirety for all purposes. The synthesis of cationic lipids such as C2-DLinDMA and C2-DLinDAP, as well as additional cationic lipids, is described in international patent application number WO2011/000106 the disclosure of which is herein incorporated by reference in its entirety for all purposes.

In another aspect, cationic lipids of Formula II having the following structure (or salts thereof) are useful in the present invention:

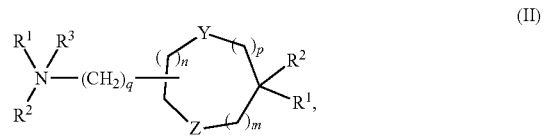

(II)

wherein $R^1$ and $R^2$ are either the same or different and are independently an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl; $R^3$ and $R^4$ are either the same or different and are independently an optionally substituted $C_1$-$C_6$ alkyl, $C_2$-$C_6$ alkenyl, or $C_2$-$C_6$ alkynyl, or $R^3$ and $R^4$ may join to form an optionally substituted heterocyclic ring of 4 to 6 carbon atoms and 1 or 2 heteroatoms chosen from nitrogen and oxygen; $R^5$ is either absent or is hydrogen (H) or a $C_1$-$C_6$ alkyl to provide a quaternary amine; m, n, and p are either the same or different and are independently either 0, 1, or 2, with the proviso that m, n, and p are not simultaneously 0; q is 0, 1, 2, 3, or 4; and Y and Z are either the same or different and are independently O, S, or NH. In a preferred embodiment, q is 2.

In some embodiments, the cationic lipid of Formula II is 2,2-dilinoleyl-4-(2-dimethylaminoethyl)-[1,3]-dioxolane, 2,2-dilinoleyl-4-(3-dimethylaminopropyl)-[1,3]-dioxolane, 2,2-dilinoleyl-4-(4-dimethylaminobutyl)-[1,3]-dioxolane, 2,2-dilinoleyl-5-dimethylaminomethyl-[1,3]-dioxane, 2,2-dilinoleyl-4-N-methylpepiazino-[1,3]-dioxolane, 2,2-dilinoleyl-4-dimethylaminomethyl-[1,3]-dioxolane, 2,2-dioleoyl-4-dimethylaminomethyl-[1,3]-dioxolane, 2,2-distearoyl-4-dimethylaminomethyl-[1,3]-dioxolane, 2,2-dilinoleyl-4-N-morpholino-[1,3]-dioxolane, 2,2-Dilinoleyl-4-trimethylamino-[1,3]-dioxolane chloride, 2,2-dilinoleyl-4,5-bis(dimethylaminomethyl)-[1,3]-dioxolane, 2,2-dilinoleyl-4-methylpiperzine-[1,3]-dioxolane, or mixtures thereof. In preferred embodiments, the cationic lipid of Formula II is 2,2-dilinoleyl-4-(2-dimethylaminoethyl)-[1,3]-dioxolane.

In some embodiments, the cationic lipid of Formula II forms a salt (preferably a crystalline salt) with one or more anions. In one particular embodiment, the cationic lipid of Formula II is the oxalate (e.g., hemioxalate) salt thereof, which is preferably a crystalline salt.

The synthesis of cationic lipids such as 2,2-dilinoleyl-4-dimethylaminomethyl-[1,3]-dioxolane, as well as additional cationic lipids, is described in PCT Publication No. WO 09/086558, the disclosure of which is herein incorporated by reference in its entirety for all purposes, and in PCT Application No. PCT/US2009/060251, entitled "Improved Amino Lipids and Methods for the Delivery of Nucleic Acids," the disclosure of which is incorporated herein by reference in its entirety for all purposes.

In a further aspect, cationic lipids of Formula III having the following structure are useful in the present invention:

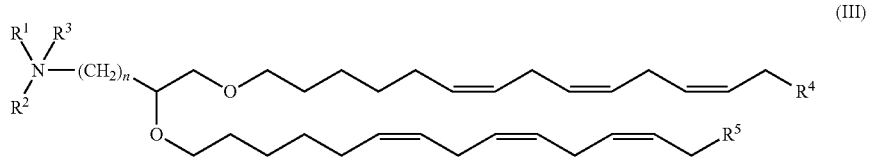

or salts thereof, wherein: $R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring of 4 to 6 carbon atoms and 1 or 2 heteroatoms selected from the group consisting of nitrogen (N), oxygen (O), and mixtures thereof; $R^3$ is either absent or is hydrogen (H) or a $C_1$-$C_6$ alkyl to provide a quaternary amine; $R^4$ and $R^5$ are either absent or present and when present are either the same or different and are independently an optionally substituted $C_1$-$C_{10}$ alkyl or $C_2$-$C_{10}$ alkenyl; and n is 0, 1, 2, 3, or 4.

In some embodiments, $R^1$ and $R^2$ are independently an optionally substituted $C_1$-$C_4$ alkyl, $C_2$-$C_4$ alkenyl, or $C_2$-$C_4$ alkynyl. In a preferred embodiment, $R^1$ and $R^2$ are both methyl groups. In another preferred embodiment, $R^4$ and $R^5$ are both butyl groups. In yet another preferred embodiment, n is 1. In other embodiments, $R^3$ is absent when the pH is above the $pK_a$ of the cationic lipid and $R^3$ is hydrogen when the pH is below the $pK_a$ of the cationic lipid such that the amino head group is protonated. In an alternative embodiment, $R^3$ is an optionally substituted $C_1$-$C_4$ alkyl to provide a quaternary amine. In further embodiments, $R^4$ and $R^5$ are independently an optionally substituted $C_2$-$C_6$ or $C_2$-$C_4$ alkyl or $C_2$-$C_6$ or $C_2$-$C_4$ alkenyl.

In an alternative embodiment, the cationic lipid of Formula III comprises ester linkages between the amino head group and one or both of the alkyl chains. In some embodiments, the cationic lipid of Formula III forms a salt (preferably a crystalline salt) with one or more anions. In one particular embodiment, the cationic lipid of Formula III is the oxalate (e.g., hemioxalate) salt thereof, which is preferably a crystalline salt.

Although each of the alkyl chains in Formula III contains cis double bonds at positions 6, 9, and 12 (i.e., cis,cis,cis-$\Delta^6,\Delta^9,\Delta^{12}$), in an alternative embodiment, one, two, or three of these double bonds in one or both alkyl chains may be in the trans configuration.

In one embodiment, the cationic lipid of Formula III has the structure:

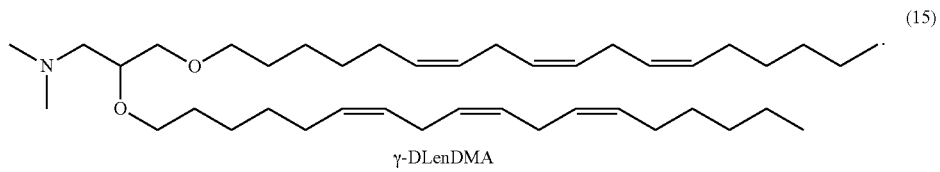 [SMILES: CCCCC/C=C\C/C=C\C/C=C\CCCCCOCC(CN(C)C)OCCCCC/C=C\C/C=C\C/C=C\CCCCC]

γ-DLenDMA

The synthesis of cationic lipids such as γ-DLenDMA, as well as additional cationic lipids, is described in International Patent Application WO2011/000106, the disclosure of which is herein incorporated by reference in its entirety for all purposes.

In particular embodiments, a cationic lipid having the following structure is useful in the present invention:

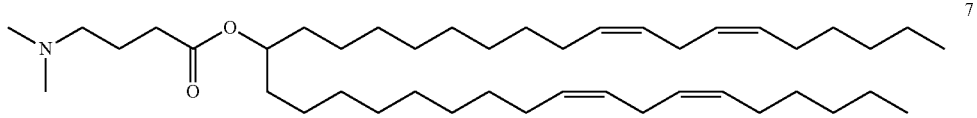 [SMILES: CCCCC/C=C\C/C=C\CCCCCCCCC(CCCCCCCC/C=C\C/C=C\CCCCC)OC(=O)CCCN(C)C]

The synthesis of cationic lipids such as compound 7, as well as additional cationic lipids, are described in U.S. Pat. No. 8,158,601, and in International Patent Application serial number PCT/GB2011/000723, the disclosures of which are herein incorporated by reference in their entirety for all purposes.

Examples of other cationic lipids or salts thereof which may be included in the lipid particles of the present invention include, but are not limited to, cationic lipids such as those described in WO2011/000106, the disclosure of which is herein incorporated by reference in its entirety for all purposes, as well as cationic lipids such as N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), 1,2-dioeylcarbamoyloxy-3-dimethylaminopropane (DO-C-DAP), 1,2-dimyristoleoyl-3-dimethylaminopropane (DM-DAP), 1,2-dioleoyl-3-trimethylaminopropane chloride (DO-TAP.Cl), dilinoleylmethyl-3-dimethylaminopropionate (DLin-M-C2-DMA; also known as DLin-M-K-DMA or DLin-M-DMA), and mixtures thereof. Additional cationic lipids or salts thereof which may be included in the lipid particles of the present invention are described in U.S. Patent Publication No. 20090023673, the disclosure of which is herein incorporated by reference in its entirety for all purposes.

In another embodiment, a trialkyl cationic lipid can be used to prepare the lipid particles described herein. Such trialkyl cationic lipids typically comprise three saturated or unsaturated hydrocarbon chains having six or more carbons in each chain. Trialkyl cationic lipids that can be incorporated into the compositions described herein can be prepared as described in International Patent Application Publication Number WO 2013/126803.

For example, a trialkyl cationic lipid of the following Formula B can be used to make lipid particles of the present invention:

X-A-Y—Z; (Formula B)

or salts thereof, wherein:

X is —N(H)R or —NR$_2$;

A is absent, $C_1$ to $C_6$alkyl, $C_2$ to $C_6$alkenyl, or $C_2$ to $C_6$alkynyl, which $C_1$ to $C_6$alkyl, $C_2$ to $C_6$alkenyl, and $C_2$ to $C_6$alkynyl is optionally substituted with one or more groups independently selected from oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$, wherein n is 0, 1, or 2, and R$^x$ and R$^y$ are each independently hydrogen, alkyl, or heterocycle, wherein each alkyl and heterocycle of R$^x$ and R$^y$ may be further substituted with one or more groups independently selected from oxo, halogen, —OH, —CN, alkyl, —OR$^{x'}$, heterocycle, —NR$^{x'}$R$^{y'}$, —NR$^{x'}$C(=O)R$^{y'}$, —NR$^{x'}$SO$_2$R$^{y'}$, —C(=O)R$^{x'}$, —C(=O)OR$^{x'}$, —C(=O)NR$^{x'}$R$^{y'}$, —SO$_n$R$^{x'}$, and —SO$_n$NR$^{x'}$R$^{y'}$, wherein n' is 0, 1, or 2, and R$^{x'}$ and R$^{y'}$ are each independently hydrogen, alkyl, or heterocycle;

Y is selected from the group consisting of absent, —C(=O)—, —O—, —OC(=O)—, —C(=O)O—, —N(R$^b$)C(=O)—, —C(=O)N(R$^b$)—, —N(R$^b$)C(=O)O—, and —OC(=O)N(R$^b$)—;

Z is a hydrophobic moiety comprising three chains wherein each of the chains is independently selected from $C_8$ to $C_{11}$alkyl, $C_8$ to $C_{11}$alkenyl, and $C_8$ to $C_{11}$alkynyl, which $C_8$ to $C_{11}$alkyl, $C_8$ to $C_{11}$alkenyl, and $C_8$ to $C_{11}$alkynyl is optionally substituted with one or more groups independently selected from oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$, wherein n is 0, 1, or 2, and R$^x$ and R$^y$ are each independently hydrogen, alkyl, or heterocycle, wherein any alkyl and heterocycle of R$^x$ and R$^y$ may be further substituted with one or more groups independently selected from oxo, halogen, —OH, —CN, alkyl, —OR$^{x'}$, heterocycle, —NR$^{x'}$R$^{y'}$, —NR$^{x'}$C(=O)R$^{y'}$, —NR$^{x'}$SO$_2$R$^{y'}$, —C(=O)R$^{x'}$, —C(=O)OR$^{x'}$, —C(=O)NR$^{x'}$R$^{y'}$, —SO$_n$R$^{x'}$, and —SO$_n$NR$^{x'}$R$^{y'}$, wherein n' is 0, 1, or 2, and R$^{x'}$ and R$^{y'}$ are each independently hydrogen, alkyl, or heterocycle;

each R is independently alkyl, alkenyl, or alkynyl, that is optionally substituted with one or more groups independently selected from oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$, wherein n is 0, 1, or 2, and R$^x$ and R$^y$ are each independently hydrogen, alkyl, or heterocycle, wherein any alkyl and heterocycle of R$^x$ and R$^y$ may be further substituted with one or more groups independently selected from oxo, halogen, —OH, —CN, alkyl, —OR$^{x'}$, heterocycle, —NR$^{x'}$R$^{y'}$, —NR$^{x'}$C(=O)R$^{y'}$, —NR$^{x'}$SO$_2$R$^{y'}$, —C(=O)R$^{x'}$, —C(=O)OR$^{x'}$, —C(=O)NR$^{x'}$R$^{y'}$, —SO$_n$R$^{x'}$, and —SO$_n$NR$^{x'}$R$^{y'}$, wherein n' is 0, 1, or 2, and R$^{x'}$ and R$^{y'}$ are each independently hydrogen, alkyl, or heterocycle; and each R$^b$ is H or $C_1$ to $C_6$alkyl.

In some embodiments, Z in Formula B has the structure:

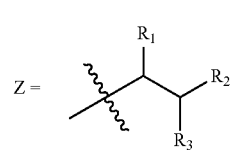

wherein, $R_1$, $R_2$, and $R_3$ are each independently $C_8$ to $C_{11}$alkyl, $C_8$ to $C_{11}$alkenyl, or $C_8$ to $C_{11}$alkynyl, which $C_8$ to $C_{11}$alkyl, $C_8$ to $C_{11}$alkenyl, and $C_8$ to $C_{11}$alkynyl is optionally substituted with one or more groups independently selected from oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$, wherein n is 0, 1, or 2, and R$^x$ and R$^y$ are each independently hydrogen, alkyl, or heterocycle, wherein any alkyl and heterocycle of R$^x$ and R$^y$ may be further substituted with one or more groups independently selected from oxo, halogen, —OH, —CN, alkyl, —OR$^{x'}$, heterocycle, —NR$^{x'}$R$^{y'}$, —NR$^{x'}$C(=O)R$^{y'}$, —NR$^{x'}$SO$_2$R$^{y'}$, —C(=O)R$^{x'}$, —C(=O)OR$^{x'}$, —C(=O)NR$^{x'}$R$^{y'}$, —SO$_n$R$^{x'}$, and —SO$_{n'}$NR$^{x'}$R$^{y'}$, wherein n' is 0, 1, or 2, and R$^{x'}$ and R$^{y'}$ are each independently hydrogen, alkyl, or heterocycle.

In another embodiment, cationic lipids of the following Formula C are used to make lipid particles of the present invention:

X-A-Y—Z$^1$;     (Formula C)

or salts thereof, wherein:

X is —N(H)R or —NR$_2$;

A is absent, C$_1$ to C$_6$alkyl, C$_2$ to C$_6$alkenyl, or C$_2$ to C$_6$alkynyl, which C$_1$ to C$_6$alkyl, C$_2$ to C$_6$alkenyl, and C$_2$ to C$_6$alkynyl is optionally substituted with one or more groups independently selected from oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$, wherein n is 0, 1, or 2, and R$^x$ and R$^y$ are each independently hydrogen, alkyl, or heterocycle, wherein each alkyl and heterocycle of R$^x$ and R$^y$ may be further substituted with one or more groups independently selected from oxo, halogen, —OH, —CN, alkyl, —OR$^{x'}$, heterocycle, —NR$^{x'}$R$^{y'}$, —NR$^{x'}$C(=O)R$^{y'}$, —NR$^{x'}$SO$_2$R$^{y'}$, —C(=O)R$^{x'}$, —C(=O)OR$^{x'}$, —C(=O)NR$^{x'}$R$^{y'}$, —SO$_n$R$^{x'}$, and —SO$_{n'}$NR$^{x'}$R$^{y'}$, wherein n' is 0, 1, or 2, and R$^{x'}$ and R$^{y'}$ are each independently hydrogen, alkyl, or heterocycle;

Y is selected from the group consisting of absent, —C(=O)—, —O—, —OC(=O)—, —C(=O)O—, —N(R$^b$)C(=O)—, —C(=O)N(R$^b$)—, —N(R$^b$)C(=O)O—, and —OC(=O)N(R$^b$)—;

Z$^1$ is a C$_1$ to C$_6$alkyl that is substituted with three or four R$^x$ groups, wherein each R$^x$ is independently selected from C$_6$ to C$_{11}$alkyl, C$_6$ to C$_{11}$alkenyl, and C$_6$ to C$_{11}$alkynyl, which C$_6$ to C$_{11}$alkyl, C$_6$ to C$_{11}$alkenyl, and C$_6$ to C$_{11}$alkynyl is optionally substituted with one or more groups independently selected from oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$, wherein n is 0, 1, or 2, and R$^x$ and R$^y$ are each independently hydrogen, alkyl, or heterocycle, wherein any alkyl and heterocycle of R$^x$ and R$^y$ may be further substituted with one or more groups independently selected from oxo, halogen, —OH, —CN, alkyl, —OR$^{x'}$, heterocycle, —NR$^{x'}$R$^{y'}$, —NR$^{x'}$C(=O)R$^{y'}$, —NR$^{x'}$SO$_2$R$^{y'}$, —C(=O)R$^{x'}$, —C(=O)OR$^{x'}$, —C(=O)NR$^{x'}$R$^{y'}$, —SO$_n$R$^{x'}$, and —SO$_{n'}$NR$^{x'}$R$^{y'}$, wherein n' is 0, 1, or 2, and R$^{x'}$ and R$^{y'}$ are each independently hydrogen, alkyl, or heterocycle;

each R is independently alkyl, alkenyl, or alkynyl, that is optionally substituted with one or more groups independently selected from oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$, wherein n is 0, 1, or 2, and R$^x$ and R$^y$ are each independently hydrogen, alkyl, or heterocycle, wherein any alkyl and heterocycle of R$^x$ and R$^y$ may be further substituted with one or more groups independently selected from oxo, halogen, —OH, —CN, alkyl, —OR$^{x'}$, heterocycle, —NR$^{x'}$R$^{y'}$, —NR$^{x'}$C(=O)R$^{y'}$, —NR$^{x'}$SO$_2$R$^{y'}$, —C(=O)R$^{x'}$, —C(=O)OR$^{x'}$, —C(=O)NR$^{x'}$R$^{y'}$, —SO$_n$R$^{x'}$, and —SO$_{n'}$NR$^{x'}$R$^{y'}$, wherein n' is 0, 1, or 2, and R$^{x'}$ and R$^{y'}$ are each independently hydrogen, alkyl, or heterocycle; and each R$^b$ is H or C$_1$ to C$_6$alkyl.

In some embodiments, Z$^1$ in Formula C has the structure:

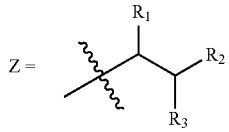

wherein, R$_1$, R$_2$, and R$_3$ are each independently C$_8$ to C$_{11}$alkyl, C$_8$ to C$_{11}$alkenyl, or C$_8$ to C$_{11}$alkynyl, which C$_8$ to C$_{11}$alkyl, C$_8$ to C$_{11}$alkenyl, and C$_8$ to C$_{11}$alkynyl is optionally substituted with one or more groups independently selected from oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$, and —SO$_n$NR$^x$R$^y$, wherein n is 0, 1, or 2, and R$^x$ and R$^y$ are each independently hydrogen, alkyl, or heterocycle, wherein any alkyl and heterocycle of R$^x$ and R$^y$ may be further substituted with one or more groups independently selected from oxo, halogen, —OH, —CN, alkyl, —OR$^{x'}$, heterocycle, —NR$^{x'}$R$^{y'}$, —NR$^{x'}$C(=O)R$^{y'}$, —NR$^{x'}$SO$_2$R$^{y'}$, —C(=O)R$^{x'}$, —C(=O)OR$^{x'}$, —C(=O)NR$^{x'}$R$^{y'}$, —SO$_n$R$^{x'}$, and —SO$_{n'}$NR$^{x'}$R$^{y'}$, wherein n' is 0, 1, or 2, and R$^{x'}$ and R$^{y'}$ are each independently hydrogen, alkyl, or heterocycle.

In some embodiments, Z$^1$ in Formula C has the structure:

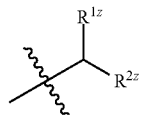

wherein one of R$^{1z}$ and R$^{2z}$ is selected from the group consisting of:

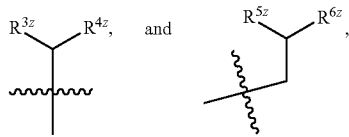

and the other of R$^{1z}$ and R$^{2z}$ is selected from the group consisting of:

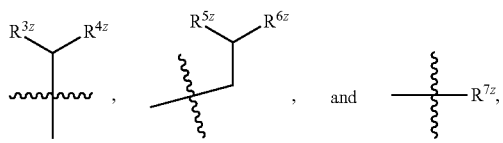

wherein each R$^{3z}$, R$^{4z}$, R$^{5z}$, R$^{6z}$, and R$^{7z}$ is independently selected from C$_6$ to C$_{11}$alkyl, C$_6$ to C$_{11}$alkenyl, and C$_6$ to C$_{11}$alkynyl, which C$_6$ to C$_{11}$alkyl, C$_6$ to C$_{11}$alkenyl, and C$_6$ to C$_{11}$alkynyl is optionally substituted with one or more groups independently selected from oxo, halogen, heterocycle, —CN, —OR$^x$, —NR$^x$R$^y$, —NR$^x$C(=O)R$^y$, —NR$^x$SO$_2$R$^y$, —C(═O)R$^x$, —C(═O)OR$^x$, —C(═O)NR$^x$R$^y$, —SO$_n$R$^x$, and —SO$_n$NR$^x$R$^y$, wherein n is 0, 1, or 2, and R$^x$ and R$^y$ are each independently hydrogen, alkyl, or heterocycle, wherein any alkyl and heterocycle of R$^x$ and R$^y$ may be further substituted with one or more groups independently selected from oxo, halogen, —OH, —CN, alkyl, —OR$^{x'}$, heterocycle, —NR$^{x'}$R$^{y'}$, —NR$^{x'}$C(═O)R$^{y'}$, —NR$^{x'}$SO$_2$R$^{y'}$, —C(═O)R$^{x'}$, —C(═O)OR$^{x'}$, —C(═O)NR$^{x'}$R$^{y'}$, —SO$_{n'}$R$^{x'}$, and —SO$_{n'}$NR$^{x'}$R$^{y'}$, wherein n' is 0, 1, or 2, and R$^{x'}$ and R$^{y'}$ are each independently hydrogen, alkyl, or heterocycle.

In some embodiments, Z$^1$ in Formula C has the structure:

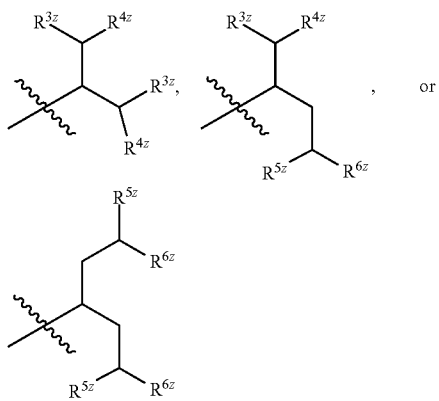

wherein each R$^{3z}$, R$^{4z}$, R$^{5z}$, and R$^{6z}$ is independently selected from C$_6$ to C$_{11}$alkyl, C$_6$ to C$_{11}$alkenyl, and C$_6$ to C$_{11}$alkynyl, which C$_6$ to C$_{11}$alkyl, C$_6$ to C$_{11}$alkenyl, and C$_6$ to C$_{11}$alkynyl is optionally substituted with one or more groups independently selected from oxo, halogen, heterocycle, —CN, —OR$^x$, —NR$^x$R$^y$, —NR$^x$C(═O)R$^y$, —NR$^x$SO$_2$R$^y$, —C(═O)R$^x$, —C(═O)OR$^x$, —C(═O)NR$^x$R$^y$, —SO$_n$R$^x$, and —SO$_n$NR$^x$R$^y$, wherein n is 0, 1, or 2, and R$^x$ and R$^y$ are each independently hydrogen, alkyl, or heterocycle, wherein any alkyl and heterocycle of R$^x$ and R$^y$ may be further substituted with one or more groups independently selected from oxo, halogen, —OH, —CN, alkyl, —OR$^{x'}$, heterocycle, —NR$^{x'}$R$^{y'}$, —NR$^{x'}$C(═O)R$^{y'}$, —NR$^{x'}$SO$_2$R$^{y'}$, —C(═O)R$^{x'}$, —C(═O)OR$^{x'}$, —C(═O)NR$^{x'}$R$^{y'}$, —SO$_{n'}$R$^{x'}$, and —SO$_{n'}$NR$^{x'}$R$^{y'}$, wherein n' is 0, 1, or 2, and R$^{x'}$ and R$^{y'}$ are each independently hydrogen, alkyl, or heterocycle.

In some embodiments the cationic lipid is selected from the group consisting of:

111

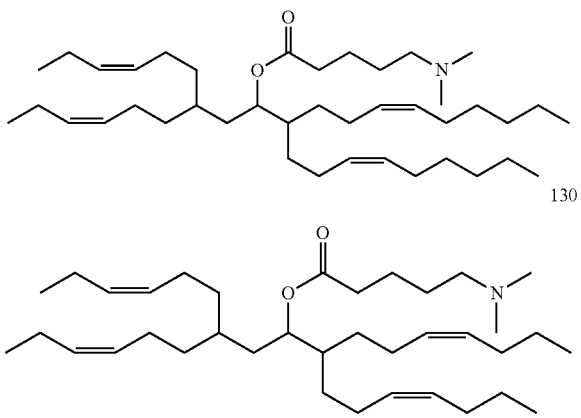

130

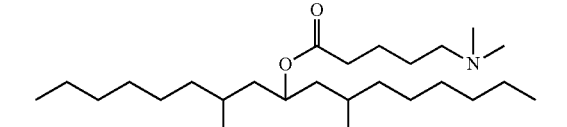

135

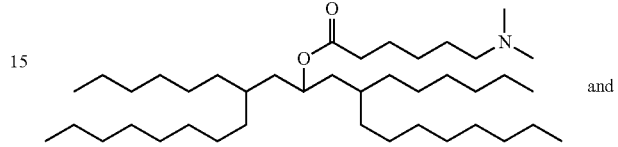

137 and

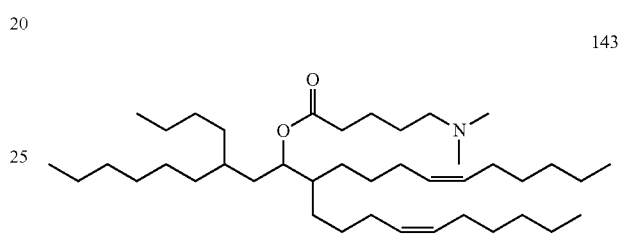

143 and salts thereof.

The synthesis of cationic lipids such as CLinDMA, as well as additional cationic lipids, is described in U.S. Patent Publication No. 20060240554, the disclosure of which is herein incorporated by reference in its entirety for all purposes. The synthesis of cationic lipids such as DLin-C-DAP, DLinDAC, DLinMA, DLinDAP, DLin-S-DMA, DLin-2-DMAP, DLinTMA.Cl, DLinTAP.Cl, DLinMPZ, DLinAP, DOAP, and DLin-EG-DMA, as well as additional cationic lipids, is described in PCT Publication No. WO 09/086558, the disclosure of which is herein incorporated by reference in its entirety for all purposes. The synthesis of cationic lipids such as DO-C-DAP, DMDAP, DOTAP.Cl, DLin-M-C2-DMA, as well as additional cationic lipids, is described in PCT Application No. PCT/US2009/060251, entitled "Improved Amino Lipids and Methods for the Delivery of Nucleic Acids," filed Oct. 9, 2009, the disclosure of which is incorporated herein by reference in its entirety for all purposes. The synthesis of a number of other cationic lipids and related analogs has been described in U.S. Pat. Nos. 5,208,036; 5,264,618; 5,279,833; 5,283,185; 5,753,613; and 5,785,992; and PCT Publication No. WO 96/10390, the disclosures of which are each herein incorporated by reference in their entirety for all purposes. Additionally, a number of commercial preparations of cationic lipids can be used, such as, e.g., LIPOFECTIN® (including DOTMA and DOPE, available from Invitrogen); LIPOFECTAMINE® (including DOSPA and DOPE, available from Invitrogen); and TRANSFECTAM® (including DOGS, available from Promega Corp.).

In some embodiments, the cationic lipid comprises from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, from about 50 mol % to about 60 mol %, from about 55 mol % to about 65 mol %, or from about 55 mol % to about 70 mol % (or any fraction thereof or range therein) of the total lipid present in the particle. In particular embodiments, the cationic lipid comprises about 50 mol %, 51 mol %, 52 mol %, 53 mol %, 54 mol %, 55 mol %, 56 mol %, 57 mol %, 58 mol %, 59 mol %, 60 mol %, 61 mol %, 62 mol %, 63 mol %, 64 mol %, or 65 mol % (or any fraction thereof) of the total lipid present in the particle.

In other embodiments, the cationic lipid comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % (or any fraction thereof or range therein) of the total lipid present in the particle.

Additional percentages and ranges of cationic lipids suitable for use in the lipid particles of the present invention are described in PCT Publication No. WO 09/127060, U.S. Published Application No. US 2011/0071208, PCT Publication No. WO2011/000106, and U.S. Published Application No. US 2011/0076335, the disclosures of which are herein incorporated by reference in their entirety for all purposes.

It should be understood that the percentage of cationic lipid present in the lipid particles of the invention is a target amount, and that the actual amount of cationic lipid present in the formulation may vary, for example, by ±5 mol %. For example, in the 1:57 lipid particle (e.g., SNALP) formulation, the target amount of cationic lipid is 57.1 mol %, but the actual amount of cationic lipid may be ±5 mol %, ±4 mol %, ±3 mol %, ±2 mol %, 1 mol %, 0.75 mol %, 0.5 mol %, ±0.25 mol %, or ±0.1 mol % of that target amount, with the balance of the formulation being made up of other lipid components (adding up to 100 mol % of total lipids present in the particle).

By way of non-limiting example, cationic lipids include the following compounds:

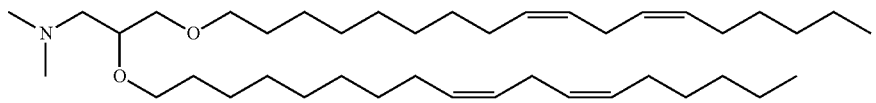 [SMILES: CCCCC/C=C\C/C=C\CCCCCCCCOCC(CN(C)C)OCCCCCCCC/C=C\C/C=C\CCCCC]

N,N-dimethyl-2,3-bis((9Z,12Z)-octadeca-9,12-dienyloxy)propan-1-amine (5)

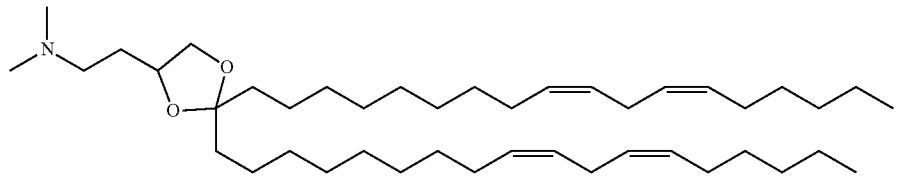

2-(2,2-di((9Z,12Z)-octadeca-9,12-dienyl)-1,3-dioxolan-4-yl)-N,N-dimethylethanamine (6)

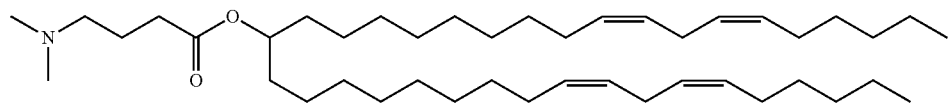 [SMILES: CCCCC/C=C\C/C=C\CCCCCCCCC(CCCCCCCC/C=C\C/C=C\CCCCC)OC(=O)CCCN(C)C]

(6Z,9Z,28Z,31Z)-heptatriaconta-6,9,28,31-tetraen-19-yl 4-(dimethylamino)butanoate (7)

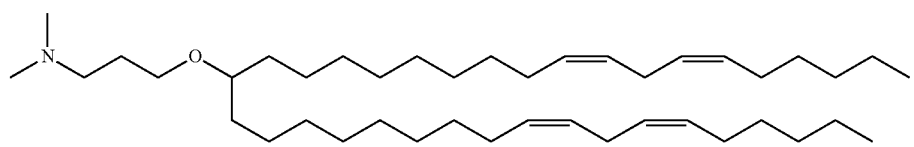 [SMILES: CCCCC/C=C\C/C=C\CCCCCCCCC(CCCCCCCC/C=C\C/C=C\CCCCC)OCCCN(C)C]

3-((6Z,9Z,28Z,31Z)-heptatriaconta-6,9,28,31-tetraen-19-yloxy)-N,N-dimethylpropan-1-amine (8)

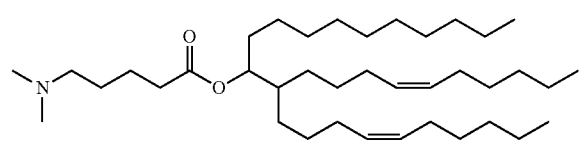 [SMILES: CCCCC/C=C\CCCC(CCC/C=C\CCCCC)C(CCCCCCCCCC)OC(=O)CCCCN(C)C]

(Z)-12-((Z)-dec-4-enyl)docos-16-en-11-yl 5-(dimethylamino)pentanoate (53)

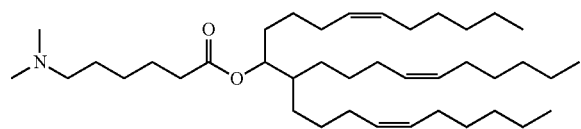 [SMILES: CCCCC/C=C\CCCC(CCC/C=C\CCCCC)C(CCC/C=C\CCCCC)OC(=O)CCCCCN(C)C]

(6Z,16Z)-12-((Z)-dec-4-enyl)docosa-6,16-dien-11-yl 6-(dimethylamino)hexanoate (11)

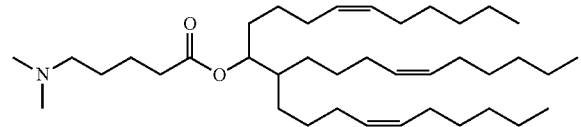 [SMILES: CCCCC/C=C\CCCC(CCC/C=C\CCCCC)C(CCC/C=C\CCCCC)OC(=O)CCCCN(C)C]

(6Z,16Z)-12-((Z)-dec-4-enyl)docosa-6,16-dien-11-yl 5-(dimethylamino)pentanoate (13)

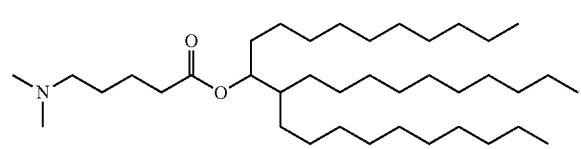 [SMILES: CCCCCCCCCCC(CCCCCCCCCC)C(CCCCCCCCCC)OC(=O)CCCCN(C)C]

12-decyldocosan-11-yl 5-(dimethylamino)pentanoate (14)

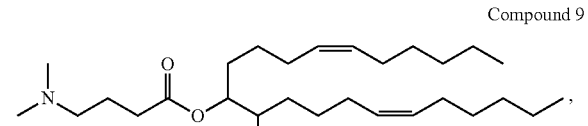

Compound 9

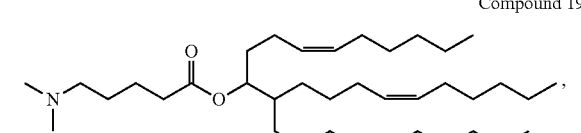

Compound 19

-continued

Compound 21

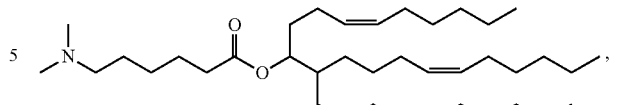

Compound 22

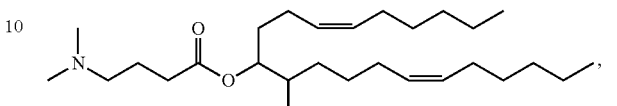

Compound 23

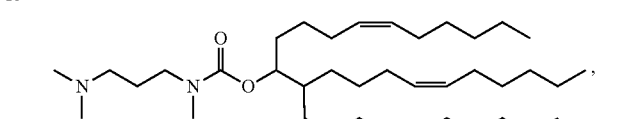

Compound 24

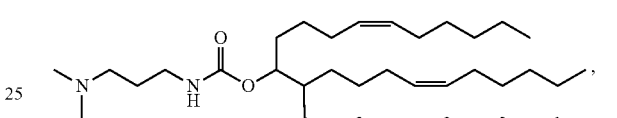

Compound 25

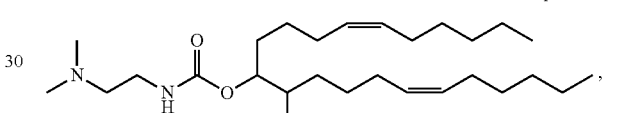

Compound 26

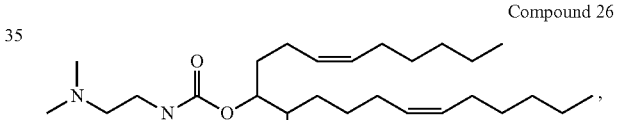

Compound 27

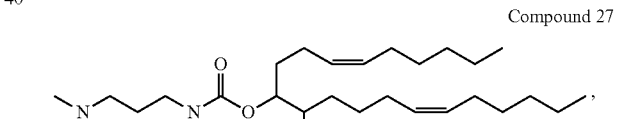

Compound 28

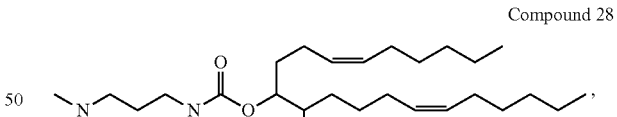

Compound 30

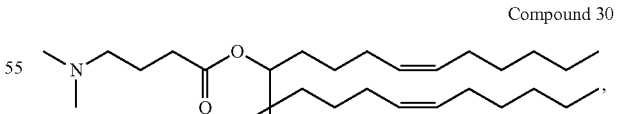

Compound 31

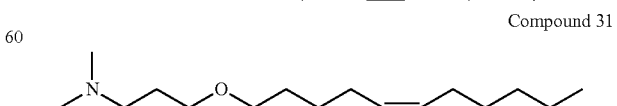

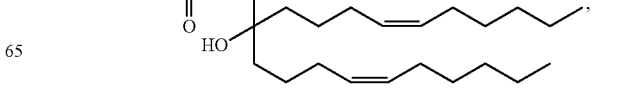

Compound 40
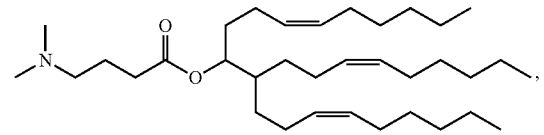

Compound 42
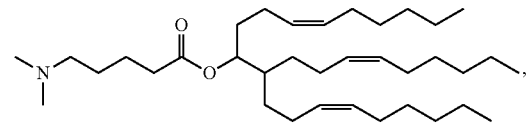

Compound 50
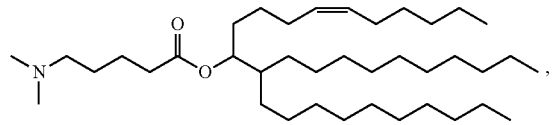

Compound 62
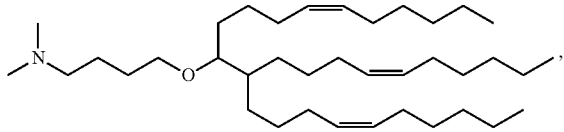

Compound 71
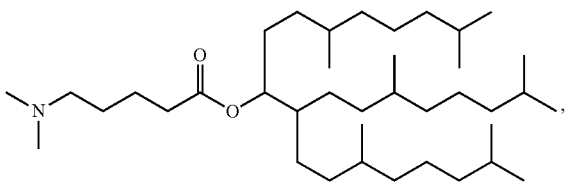

Compound 74
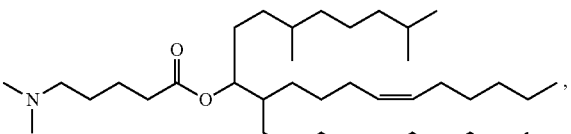

Compound 76
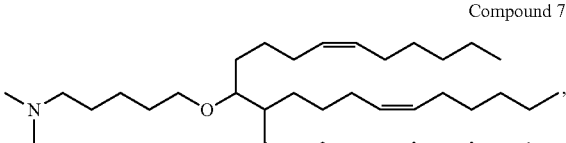

Compound 79
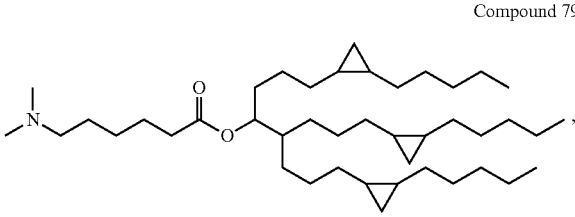

Compound 83
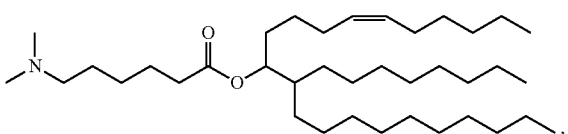

Compound 89
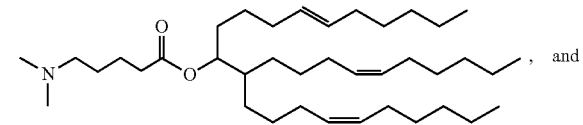
, and

Compound 90
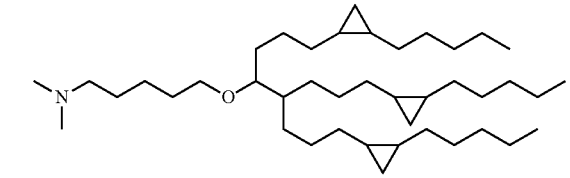

Non-Cationic Lipids

The non-cationic lipids used in the lipid particles of the invention (e.g., SNALP) can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, di stearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lyso-phosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5β-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In preferred embodiments, the cholesterol derivative is a polar analogue such as cholesteryl-(4'-hydroxy)-butyl ether. The synthesis of cholesteryl-(2'-hydroxy)-ethyl ether is described in PCT Publication No. WO 09/127060, the disclosure of which is herein incorporated by reference in its entirety for all purposes.

In some embodiments, the non-cationic lipid present in the lipid particles (e.g., SNALP) comprises or consists of a mixture of one or more phospholipids and cholesterol or a derivative thereof. In other embodiments, the non-cationic lipid present in the lipid particles (e.g., SNALP) comprises or consists of one or more phospholipids, e.g., a cholesterol-free lipid particle formulation. In yet other embodiments, the non-cationic lipid present in the lipid particles (e.g., SNALP) comprises or consists of cholesterol or a derivative thereof, e.g., a phospholipid-free lipid particle formulation.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

In some embodiments, the non-cationic lipid comprises from about 10 mol % to about 60 mol %, from about 20 mol % to about 55 mol %, from about 20 mol % to about 45 mol %, from about 20 mol % to about 40 mol %, from about 25 mol % to about 50 mol %, from about 25 mol % to about 45 mol %, from about 30 mol % to about 50 mol %, from about 30 mol % to about 45 mol %, from about 30 mol % to about 40 mol %, from about 35 mol % to about 45 mol %, from about 37 mol % to about 42 mol %, or about 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to about 40 mol %, 45 mol %, 50 mol %, 55 mol %, or 60 mol % of the total lipid present in the particle.

In some embodiments, the phospholipid component in the mixture may comprise from about 2 mol % to about 20 mol %, from about 2 mol % to about 15 mol %, from about 2 mol % to about 12 mol %, from about 4 mol % to about 15 mol %, or from about 4 mol % to about 10 mol % (or any fraction thereof or range therein) of the total lipid present in the particle. In certain preferred embodiments, the phospholipid component in the mixture comprises from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. As a non-limiting example, a 1:57 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 34 mol % (or any fraction thereof) of the total lipid present in the particle. As another non-limiting example, a 7:54 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 32 mol % (or any fraction thereof) of the total lipid present in the particle.

In other embodiments, the cholesterol component in the mixture may comprise from about 25 mol % to about 45 mol %, from about 25 mol % to about 40 mol %, from about 30 mol % to about 45 mol %, from about 30 mol % to about 40 mol %, from about 27 mol % to about 37 mol %, from about 25 mol % to about 30 mol %, or from about 35 mol % to about 40 mol % (or any fraction thereof or range therein) of the total lipid present in the particle. In certain preferred embodiments, the cholesterol component in the mixture comprises from about 25 mol % to about 35 mol %, from about 27 mol % to about 35 mol %, from about 29 mol % to about 35 mol %, from about 30 mol % to about 35 mol %, from about 30 mol % to about 34 mol %, from about 31 mol % to about 33 mol %, or about 30 mol %, 31 mol %, 32 mol %, 33 mol %, 34 mol %, or 35 mol % (or any fraction thereof or range therein) of the total lipid present in the particle. Typically, a 1:57 lipid particle formulation comprising a mixture of phospholipid and cholesterol may comprise cholesterol or a cholesterol derivative at about 34 mol % (or any fraction thereof), e.g., in a mixture with a phospholipid such as DPPC or DSPC at about 7 mol % (or any fraction thereof) of the total lipid present in the particle. Typically, a 7:54 lipid particle formulation comprising a mixture of phospholipid and cholesterol may comprise cholesterol or a cholesterol derivative at about 32 mol % (or any fraction thereof), e.g., in a mixture with a phospholipid such as DPPC or DSPC at about 7 mol % (or any fraction thereof) of the total lipid present in the particle.

In embodiments where the lipid particles are phospholipid-free, the cholesterol or derivative thereof may comprise up to about 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from about 25 mol % to about 45 mol %, from about 25 mol % to about 40 mol %, from about 30 mol % to about 45 mol %, from about 30 mol % to about 40 mol %, from about 31 mol % to about 39 mol %, from about 32 mol % to about 38 mol %, from about 33 mol % to about 37 mol %, from about 35 mol % to about 45 mol %, from about 30 mol % to about 35 mol %, from about 35 mol % to about 40 mol %, or about 30 mol %, 31 mol %, 32 mol %, 33 mol %, 34 mol %, 35 mol %, 36 mol %, 37 mol %, 38 mol %, 39 mol %, or 40 mol % (or any fraction thereof or range therein) of the total lipid present in the particle. As a non-limiting example, a 1:62 lipid particle formulation may comprise cholesterol at about 37 mol % (or any fraction thereof) of the total lipid present in the particle. As another non-limiting example, a 7:58 lipid particle formulation may comprise cholesterol at about 35 mol % (or any fraction thereof) of the total lipid present in the particle.

In other embodiments, the non-cationic lipid comprises from about 5 mol % to about 90 mol %, from about 10 mol % to about 85 mol %, from about 20 mol % to about 80 mol %, about 10 mol % (e.g., phospholipid only), or about 60 mol % (e.g., phospholipid and cholesterol or derivative thereof) (or any fraction thereof or range therein) of the total lipid present in the particle.

Additional percentages and ranges of non-cationic lipids suitable for use in the lipid particles of the present invention are described in PCT Publication No. WO 09/127060, U.S. Published Application No. US 2011/0071208, PCT Publication No. WO2011/000106, and U.S. Published Application No. US 2011/0076335, the disclosures of which are herein incorporated by reference in their entirety for all purposes.

It should be understood that the percentage of non-cationic lipid present in the lipid particles of the invention is a target amount, and that the actual amount of non-cationic lipid present in the formulation may vary, for example, by ±5 mol %. For example, in the 1:57 lipid particle (e.g., SNALP) formulation, the target amount of phospholipid is 7.1 mol % and the target amount of cholesterol is 34.3 mol %, but the actual amount of phospholipid may be ±2 mol %, ±1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle). Similarly, in the 7:54 lipid particle (e.g., SNALP) formulation, the target amount of phospholipid is 6.75 mol % and the target amount of cholesterol is 32.43 mol %, but the actual amount of phospholipid may be ±2 mol %, ±1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

Lipid Conjugates

In addition to cationic and non-cationic lipids, the lipid particles of the invention (e.g., SNALP) may further comprise a lipid conjugate. The conjugated lipid is useful in that it prevents the aggregation of particles. Suitable conjugated lipids include, but are not limited to, PEG-lipid conjugates, POZ-lipid conjugates, ATTA-lipid conjugates, cationic-polymer-lipid conjugates (CPLs), and mixtures thereof. In certain embodiments, the particles comprise either a PEG-lipid conjugate or an ATTA-lipid conjugate together with a CPL.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes. Additional PEG-lipids suitable for use in the invention include, without limitation, mPEG2000-1,2-di-O-alkyl-sn3-carbomoylglyceride (PEG-C-DOMG). The synthesis of PEG-C-DOMG is described in PCT Publication No. WO 09/086558, the disclosure of which is herein incorporated by reference in its entirety for all purposes. Yet additional suitable PEG-lipid conjugates include, without limitation, 1-[8'-(1,2-dimyristoyl-3-propanoxy)-carbox-amido-3',6'-dioxaoctanyl]carbamoyl-ω-methyl-poly(ethylene glycol) (2KPEG-DMG). The synthesis of 2KPEG-DMG is described in U.S. Pat. No. 7,404,969, the disclosure of which is herein incorporated by reference in its entirety for all purposes.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, but are not limited to, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-NH$_2$, etc.). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycol-acetic acid (MePEG-CH$_2$COOH) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skilled in the art. Phosphatidyl-ethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "ATTA" or "polyamide" includes, without limitation, compounds described in U.S. Pat. Nos. 6,320,017 and 6,586,559, the disclosures of which are herein incorporated by reference in their entirety for all purposes. These compounds include a compound having the formula:

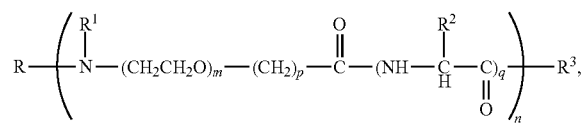
(IV)

wherein R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl), etc. Diacylglycerols have the following general formula:

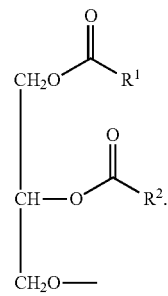
(V)

The term "dialkyloxypropyl" or "DAA" includes a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

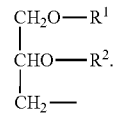
(VI)

In a preferred embodiment, the PEG-lipid is a PEG-DAA conjugate having the following formula:

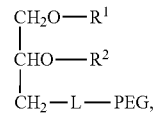
(VII)

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, decyl ($C_{10}$), lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula VII above, the PEG has an average molecular weight ranging from about 550 daltons to about 10,000 daltons. In certain instances, the PEG has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG has an average molecular weight of about 2,000 daltons or about 750 daltons. The PEG can be optionally substituted with alkyl, alkoxy, acyl, or aryl groups. In certain embodiments, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

In particular embodiments, the PEG-lipid conjugate is selected from:

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the lipid particles (e.g., SNALP) of the present invention can further comprise cationic poly(ethylene glycol) (PEG) lipids or

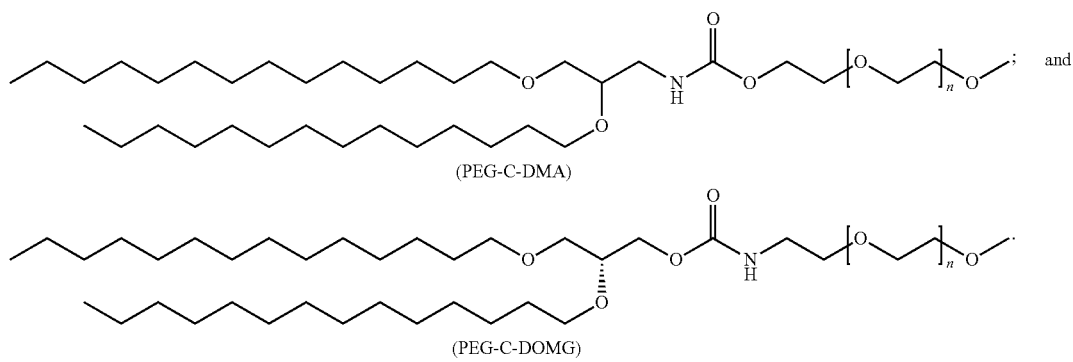

(PEG-C-DMA)

(PEG-C-DOMG)

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of about 750 or about 2,000 daltons. In one particularly preferred embodiment, the PEG-lipid conjugate comprises PEG2000-C-DMA, wherein the "2000" denotes the average molecular weight of the PEG, the "C" denotes a carbamate linker moiety, and the "DMA" denotes dimyristyloxypropyl. In another particularly preferred embodiment, the PEG-lipid conjugate comprises PEG750-C-DMA, wherein the "750" denotes the average molecular weight of the PEG, the "C" denotes a carbamate linker moiety, and the "DMA" denotes dimyristyloxypropyl. In particular embodiments, the terminal hydroxyl group of the PEG is substituted with a methyl group. Those of skill in the art will readily appreciate that other dialkyloxypropyls can be used in the PEG-DAA conjugates of the present invention.

CPLs (see, e.g., Chen et al., Bioconj. Chem., 11:433-437 (2000); U.S. Pat. No. 6,852,334; PCT Publication No. WO 00/62813, the disclosures of which are herein incorporated by reference in their entirety for all purposes).

Suitable CPLs include compounds of Formula VIII:

A-W—Y (VIII),

wherein A, W, and Y are as described below.

With reference to Formula VIII, "A" is a lipid moiety such as an amphipathic lipid, a neutral lipid, or a hydrophobic lipid that acts as a lipid anchor. Suitable lipid examples include, but are not limited to, diacylglycerolyls, dialkylglycerolyls, N—N-dialkylaminos, 1,2-diacyloxy-3-aminopropanes, and 1,2-dialkyl-3-aminopropanes.

"W" is a polymer or an oligomer such as a hydrophilic polymer or oligomer. Preferably, the hydrophilic polymer is a biocompatible polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559, the disclosures of which are herein incorporated by reference in their entirety for all purposes), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

In some embodiments, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.5 mol % (or any fraction thereof or range therein) of the total lipid present in the particle.

In other embodiments, the lipid conjugate (e.g., PEG-lipid) comprises from about 0 mol % to about 20 mol %, from about 0.5 mol % to about 20 mol %, from about 2 mol % to about 20 mol %, from about 1.5 mol % to about 18 mol %, from about 2 mol % to about 15 mol %, from about 4 mol % to about 15 mol %, from about 2 mol % to about 12 mol %, from about 5 mol % to about 12 mol %, or about 2 mol % (or any fraction thereof or range therein) of the total lipid present in the particle.

In further embodiments, the lipid conjugate (e.g., PEG-lipid) comprises from about 4 mol % to about 10 mol %, from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle.

Additional percentages and ranges of lipid conjugates suitable for use in the lipid particles of the present invention are described in PCT Publication No. WO 09/127060, U.S. Published Application No. US 2011/0071208, PCT Publication No. WO2011/000106, and U.S. Published Application No. US 2011/0076335, the disclosures of which are herein incorporated by reference in their entirety for all purposes.

It should be understood that the percentage of lipid conjugate (e.g., PEG-lipid) present in the lipid particles of the invention is a target amount, and that the actual amount of lipid conjugate present in the formulation may vary, for example, by ±2 mol %. For example, in the 1:57 lipid particle (e.g., SNALP) formulation, the target amount of lipid conjugate is 1.4 mol %, but the actual amount of lipid conjugate may be ±0.5 mol %, ±0.4 mol %, ±0.3 mol %, ±0.2 mol %, ±0.1 mol %, or ±0.05 mol % of that target amount, with the balance of the formulation being made up of other lipid components (adding up to 100 mol % of total lipids present in the particle). Similarly, in the 7:54 lipid particle (e.g., SNALP) formulation, the target amount of lipid conjugate is 6.76 mol %, but the actual amount of lipid conjugate may be ±2 mol %, ±1.5 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. For instance, when a PEG-DAA conjugate is used as the lipid conjugate, the rate at which the lipid particle becomes fusogenic can be varied, for example, by varying the concentration of the lipid conjugate, by varying the molecular weight of the PEG, or by varying the chain length and degree of saturation of the alkyl groups on the PEG-DAA conjugate. In addition, other variables including, for example, pH, temperature, ionic strength, etc. can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle (e.g., SNALP) size.

Preparation of Lipid Particles

The lipid particles of the present invention, e.g., SNALP, in which an mRNA is entrapped within the lipid portion of the particle and is protected from degradation, can be formed by any method known in the art including, but not limited to, a continuous mixing method, a direct dilution process, and an in-line dilution process.

In certain embodiments, the present invention provides nucleic acid-lipid particles (e.g., SNALP) produced via a continuous mixing method, e.g., a process that includes providing an aqueous solution comprising a nucleic acid (e.g., mRNA) in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the nucleic acid within the lipid vesicle. This process and the apparatus for carrying out this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a lipid vesicle substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The nucleic acid-lipid particles formed using the continuous mixing method typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

In another embodiment, the present invention provides nucleic acid-lipid particles (e.g., SNALP) produced via a direct dilution process that includes forming a lipid vesicle (e.g., liposome) solution and immediately and directly introducing the lipid vesicle solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of lipid vesicle solution introduced thereto. As a non-limiting example, a lipid vesicle solution in 45% ethanol when introduced into the collection vessel containing an equal volume of dilution buffer will advantageously yield smaller particles.

In yet another embodiment, the present invention provides nucleic acid-lipid particles (e.g., SNALP) produced via an in-line dilution process in which a third reservoir containing dilution buffer is fluidly coupled to a second mixing region. In this embodiment, the lipid vesicle (e.g., liposome) solution formed in a first mixing region is immediately and directly mixed with dilution buffer in the second mixing region. In preferred aspects, the second mixing region includes a T-connector arranged so that the lipid vesicle solution and the dilution buffer flows meet as opposing 180° flows; however, connectors providing shallower angles can be used, e.g., from about 27° to about 180° (e.g., about 90°). A pump mechanism delivers a controllable flow of buffer to the second mixing region. In one aspect, the flow rate of dilution buffer provided to the second mixing region is controlled to be substantially equal to the flow rate of lipid vesicle solution introduced thereto from the first mixing region. This embodiment advantageously allows for more control of the flow of dilution buffer mixing with the lipid vesicle solution in the second mixing region, and therefore also the concentration of lipid vesicle solution in buffer throughout the second mixing process. Such control of the dilution buffer flow rate advantageously allows for small particle size formation at reduced concentrations.

These processes and the apparatuses for carrying out these direct dilution and in-line dilution processes are described in detail in U.S. Patent Publication No. 20070042031, the disclosure of which is herein incorporated by reference in its entirety for all purposes.

The nucleic acid-lipid particles formed using the direct dilution and in-line dilution processes typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

If needed, the lipid particles of the invention (e.g., SNALP) can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In other embodiments, the methods may further comprise adding non-lipid polycations which are useful to effect the lipofection of cells using the present compositions. Examples of suitable non-lipid polycations include, hexadimethrine bromide (sold under the brand name POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the nucleic acid to lipid ratios (mass/mass ratios) in a formed nucleic acid-lipid particle (e.g., SNALP) will range from about 0.01 to about 0.2, from about 0.05 to about 0.2, from about 0.02 to about 0.1, from about 0.03 to about 0.1, or from about 0.01 to about 0.08. The ratio of the starting materials (input) also falls within this range. In other embodiments, the particle preparation uses about 400 µg nucleic acid per 10 mg total lipid or a nucleic acid to lipid mass ratio of about 0.01 to about 0.08 and, more preferably, about 0.04, which corresponds to 1.25 mg of total lipid per 50 µg of nucleic acid. In other preferred embodiments, the particle has a nucleic acid:lipid mass ratio of about 0.08.

In other embodiments, the lipid to nucleic acid ratios (mass/mass ratios) in a formed nucleic acid-lipid particle (e.g., SNALP) will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), or about 5 (5:1), 6 (6:1), 7 (7:1), 8 (8:1), 9 (9:1), 10 (10:1), 11 (11:1), 12 (12:1), 13 (13:1), 14 (14:1), 15 (15:1), 16 (16:1), 17 (17:1), 18 (18:1), 19 (19:1), 20 (20:1), 21 (21:1), 22 (22:1), 23 (23:1), 24 (24:1), or 25 (25:1), or any fraction thereof or range therein. The ratio of the starting materials (input) also falls within this range.

As previously discussed, the conjugated lipid may further include a CPL. A variety of general methods for making SNALP-CPLs (CPL-containing SNALP) are discussed herein. Two general techniques include the "post-insertion" technique, that is, insertion of a CPL into, for example, a pre-formed SNALP, and the "standard" technique, wherein the CPL is included in the lipid mixture during, for example, the SNALP formation steps. The post-insertion technique results in SNALP having CPLs mainly in the external face of the SNALP bilayer membrane, whereas standard techniques provide SNALP having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPLs are taught, for example, in U.S. Pat. Nos. 5,705,385; 6,586,410; 5,981,501; 6,534,484; and 6,852,334; U.S. Patent Publication No. 20020072121; and PCT Publication No. WO 00/62813, the disclosures of which are herein incorporated by reference in their entirety for all purposes.

Administration of Lipid Particles

Once formed, the lipid particles of the invention (e.g., SNALP) are particularly useful for the introduction of nucleic acids (e.g., mRNA) into cells. Accordingly, the present invention also provides methods for introducing a nucleic acid (e.g., mRNA) into a cell. In particular embodiments, the nucleic acid (e.g., mRNA) is introduced into an infected cell such as reticuloendothelial cells (e.g., macrophages, monocytes, etc.) as well as other cell types, including fibroblasts, endothelial cells (such as those lining the interior surface of blood vessels), and/or platelet cells. The methods may be carried out in vitro or in vivo by first forming the particles as described herein and then contacting the particles with the cells for a period of time sufficient for delivery of the mRNA to the cells to occur.

The lipid particles of the invention (e.g., SNALP) can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid (e.g., mRNA) portion of the particle can take place via any one of these pathways. In particular, when fusion takes place, the particle membrane is integrated into the cell membrane and the contents of the particle combine with the intracellular fluid.

The lipid particles of the invention (e.g., SNALP) can be administered either alone or in a mixture with a pharmaceutically acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically acceptable" refers to molecular entities and compositions that do not produce an allergic or similar untoward reaction when administered to a human.

The pharmaceutically acceptable carrier is generally added following lipid particle formation. Thus, after the lipid particle (e.g., SNALP) is formed, the particle can be diluted into pharmaceutically acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol, and water-soluble iron-specific chelators, such as ferrioxamine, are suitable.

In some embodiments, the lipid particles of the invention (e.g., SNALP) are particularly useful in methods for the therapeutic delivery of one or more mRNA.

In Vivo Administration

Systemic delivery for in vivo therapy, e.g., delivery of a therapeutic nucleic acid to a distal target cell via body systems such as the circulation, has been achieved using nucleic acid-lipid particles such as those described in PCT Publication Nos. WO 05/007196, WO 05/121348, WO 05/120152, and WO 04/002453, the disclosures of which are herein incorporated by reference in their entirety for all purposes. The present invention also provides fully encapsulated lipid particles that protect the nucleic acid from nuclease degradation in serum, are non-immunogenic, are small in size, and are suitable for repeat dosing.

For in vivo administration, administration can be in any manner known in the art, e.g., by injection, oral administration, inhalation (e.g., intranasal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.*, 101:512 (1983); Mannino et al., *Biotechniques*, 6:682 (1988); Nicolau et al., *Crit. Rev. Ther. Drug Carrier Syst.*, 6:239 (1989); and Behr, *Acc. Chem. Res.*, 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)). The disclosures of the above-described references are herein incorporated by reference in their entirety for all purposes.

In embodiments where the lipid particles of the present invention (e.g., SNALP) are administered intravenously, at least about 5%, 10%, 15%, 20%, or 25% of the total injected dose of the particles is present in plasma about 8, 12, 24, 36, or 48 hours after injection. In other embodiments, more than about 20%, 30%, 40% and as much as about 60%, 70% or 80% of the total injected dose of the lipid particles is present in plasma about 8, 12, 24, 36, or 48 hours after injection. In certain instances, more than about 10% of a plurality of the particles is present in the plasma of a mammal about 1 hour after administration. In certain other instances, the presence of the lipid particles is detectable at least about 1 hour after administration of the particle. In some embodiments, the presence of a therapeutic nucleic acid such as an mRNA molecule is detectable in cells at about 8, 12, 24, 36, 48, 60, 72 or 96 hours after administration. In other embodiments, expression of a polypeptide encoded by an mRNA introduced into a living body in accordance with the present invention is detectable at about 8, 12, 24, 36, 48, 60, 72 or 96 hours after administration. In further embodiments, the presence or effect of an mRNA in cells at a site proximal or distal to the site of administration is detectable at about 12, 24, 48, 72, or 96 hours, or at about 6, 8, 10, 12, 14, 16, 18, 19, 20, 22, 24, 26, or 28 days after administration. In additional embodiments, the lipid particles (e.g., SNALP) of the invention are administered parenterally or intraperitoneally.

The compositions of the present invention, either alone or in combination with other suitable components, can be made into aerosol formulations (i.e., they can be "nebulized") to be administered via inhalation (e.g., intranasally or intratracheally) (see, Brigham et al., *Am. J. Sci.*, 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also known in the pharmaceutical arts. Similarly, transmucosal drug delivery in the form of a polytetrafluoroetheylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the lipid particle formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions.

The resulting aqueous solutions may be packaged for use or filtered under aseptic conditions and lyophilized, the lyophilized preparation being combined with a sterile aqueous solution prior to administration.

In certain applications, the lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of a packaged therapeutic nucleic acid (e.g., mRNA) suspended in diluents such as water, saline, or PEG 400; (b) capsules, sachets, or tablets, each containing a predetermined amount of a therapeutic nucleic acid (e.g., mRNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a therapeutic nucleic acid (e.g., mRNA) in a flavor, e.g., sucrose, as well as pastilles comprising the therapeutic nucleic acid in an inert base, such as gelatin and glycerin or sucrose and acacia emulsions, gels, and the like containing, in addition to the therapeutic nucleic acid, carriers known in the art.

In another example of their use, lipid particles can be incorporated into a broad range of topical dosage forms. For instance, a suspension containing nucleic acid-lipid particles such as SNALP can be formulated and administered as gels, oils, emulsions, topical creams, pastes, ointments, lotions, foams, mousses, and the like.

When preparing pharmaceutical preparations of the lipid particles of the invention, it is preferable to use quantities of the particles which have been purified to reduce or eliminate empty particles or particles with therapeutic agents such as nucleic acid associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of therapeutic nucleic acid (e.g., mRNA) to lipid, the particular therapeutic nucleic acid used, the disease or disorder being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

In Vitro Administration

For in vitro applications, the delivery of therapeutic nucleic acids (e.g., mRNA) can be to any cell grown in culture, whether of plant or animal origin, vertebrate or invertebrate, and of any tissue or type. In preferred embodiments, the cells are animal cells, more preferably mammalian cells, and most preferably human cells.

Contact between the cells and the lipid particles, when carried out in vitro, takes place in a biologically compatible medium. The concentration of particles varies widely depending on the particular application, but is generally between about 1 µmol and about 10 mmol. Treatment of the cells with the lipid particles is generally carried out at physiological temperatures (about 37° C.) for periods of time of from about 1 to 48 hours, preferably of from about 2 to 4 hours.

In one group of preferred embodiments, a lipid particle suspension is added to 60-80% confluent plated cells having a cell density of from about $10^3$ to about $10^5$ cells/ml, more preferably about $2 \times 10^4$ cells/ml. The concentration of the suspension added to the cells is preferably of from about 0.01 to 0.2 µg/ml, more preferably about 0.1 µg/ml.

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

Using an Endosomal Release Parameter (ERP) assay, the delivery efficiency of the SNALP or other lipid particle of the invention can be optimized. An ERP assay is described in detail in U.S. Patent Publication No. 20030077829, the disclosure of which is herein incorporated by reference in its entirety for all purposes. More particularly, the purpose of an ERP assay is to distinguish the effect of various cationic lipids and helper lipid components of SNALP or other lipid particle based on their relative effect on binding/uptake or fusion with/destabilization of the endosomal membrane. This assay allows one to determine quantitatively how each component of the SNALP or other lipid particle affects delivery efficiency, thereby optimizing the SNALP or other lipid particle. Usually, an ERP assay measures expression of a reporter protein (e.g., luciferase, β-galactosidase, green fluorescent protein (GFP), etc.), and in some instances, a SNALP formulation optimized for an expression plasmid will also be appropriate for encapsulating an mRNA. By comparing the ERPs for each of the various SNALP or other lipid particles, one can readily determine the optimized system, e.g., the SNALP or other lipid particle that has the greatest uptake in the cell.

Cells for Delivery of Lipid Particles

The present invention can be practiced on a wide variety of cell types from any vertebrate species, including mammals, such as, e.g, canines, felines, equines, bovines, ovines, caprines, rodents (e.g., mice, rats, and guinea pigs), lagomorphs, swine, and primates (e.g. monkeys, chimpanzees, and humans).

Detection of Lipid Particles

In some embodiments, the lipid particles of the present invention (e.g., SNALP) are detectable in the subject at about 1, 2, 3, 4, 5, 6, 7, 8 or more hours. In other embodiments, the lipid particles of the present invention (e.g., SNALP) are detectable in the subject at about 8, 12, 24, 48, 60, 72, or 96 hours, or about 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, and/or detection of an mRNA sequence encapsulated within the lipid particles, and/or detection of a polypeptide expressed from an mRNA.

Detection of Particles

Lipid particles of the invention such as SNALP can be detected using any method known in the art. For example, a label can be coupled directly or indirectly to a component of the lipid particle using methods well-known in the art. A wide variety of labels can be used, with the choice of label depending on sensitivity required, ease of conjugation with the lipid particle component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3$H, $^{125}$I, $^{35}$S, $^{14}$C, $^{32}$P, $^{33}$P, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

Detection of Nucleic Acids

Nucleic acids (e.g., mRNA) are detected and quantified herein by any of a number of means well-known to those of skill in the art. The detection of nucleic acids may proceed by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through the use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification, and other RNA polymerase mediated techniques (e.g., NASBA™) are found in Sambrook et al., In *Molecular Cloning: A Laboratory Manual*, Cold Spring Harbor Laboratory Press (2000); and Ausubel et al., SHORT PROTOCOLS IN MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), *C&EN* 36; The *Journal Of NIH Research*, 3:81 (1991); Kwoh et al., *Proc. Natl. Acad. Sci. USA*, 86:1173 (1989); Guatelli et al., *Proc. Natl. Acad. Sci. USA*, 87:1874 (1990); Lomell et al., *J. Clin. Chem.*, 35:1826 (1989); Landegren et al., *Science*, 241:1077 (1988); Van Brunt, *Biotechnology*, 8:291 (1990); Wu and Wallace, *Gene*, 4:560 (1989); Barringer et al., *Gene*, 89:117 (1990); and Sooknanan and Malek, *Biotechnology*, 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation. The disclosures of the above-described references are herein incorporated by reference in their entirety for all purposes.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.*, 22:1859 1862 (1981), e.g., using an automated synthesizer, as described in Needham VanDevanter et al., *Nucleic Acids Res.*, 12:6159 (1984). Purification of polynucleotides, where necessary, is typically performed by either native acrylamide gel electrophoresis or by anion exchange HPLC as described in Pearson et al., *J. Chrom.*, 255:137 149 (1983). The sequence of the synthetic polynucleotides can be verified using the chemical degradation method of Maxam and Gilbert (1980) in Grossman and Moldave (eds.) Academic Press, New York, *Methods in Enzymology*, 65:499.

An alternative means for determining the level of transcription is in situ hybridization. In situ hybridization assays are well-known and are generally described in Angerer et al., *Methods Enzymol.*, 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. The art worker will also understand the while a "Table 1" may be included in more than one Example, references to a 'Table 1' in Example 1 refer to the Table 1 present in Example 1.

Examples 1-13

Co-Delivery of a Nucleic Acid Payload with a Steroid in Lipid Nanoparticles

Corticosteroids are a class of steroid hormones that are produced in the adrenal cortex of vertebrates, as well as the synthetic analogues of these hormones. Corticosteroids are involved in a wide range of physiological processes, including stress response, immune response, and regulation of inflammation, carbohydrate metabolism, protein catabolism, blood electrolyte levels, and behavior.

There are two classes of corticosteroids. Glucocorticoids such as cortisol control carbohydrate, fat and protein metabolism, and are anti-inflammatory by preventing phospholipid release, decreasing eosinophil action and a number of other mechanisms. Mineralocorticoids such as aldosterone control electrolyte and water levels, mainly by promoting sodium retention in the kidney.

The term "glucocorticoid" refers to any of a group of natural or synthetic steroid hormones that control carbohydrate, protein, and fat metabolism and have anti-inflammatory and/or immunosuppressive properties. Suitable glucocorticoids for use in certain embodiments of the present invention include, but are not limited to, hydrocortisone, cortisone, corticosterone, deoxycorticosterone, prednisone, prednisolone, methylprednisolone, dexamethasone, betamethasone, mometasone, triamcinolone, beclomethasone, fludrocortisone, aldosterone, fluticasone, clobetasone, clobetasol, and loteprednol, and pharmaceutically acceptable salts thereof, and mixtures thereof."

Steroids are often used in the treatment of various diseases as they can help with treatment in a number of ways. In cancer treatment, for example, steroids can reduce nausea associated with chemotherapy and radiation, decrease inflammation, reduce allergic reactions (before transfusions, for example), or simply to help improve quality of life by enabling the patient to sleep, eat, and feel better.

While the use of lipid nanoparticles is a proven delivery platform, it is necessary to further expand on the therapeutic utility and patient convenience of LNP by overcoming a number of safety and tolerability concerns. In the clinic, and the absence of premedication, most LNP treatment related adverse events are consistent with infusion-type reactions associated with increases in certain inflammatory biomarkers that may represent dose limiting toxicities. (see, e.g., Judge et al., Review: Overcoming the Innate Immune Response to Small Interfering RNA, *Human Gene Therapy*, 19, 2008)

The effects of co-formulating glucocorticoids into LNP have been investigated, to see if inflammatory response following intravenous administration could be dampened, and the therapeutic index of the platform broadened. Preclinical data generated in murine models have indicated that steroid co-formulation with LNP is a viable strategy to achieve reduced immune stimulation, while maintaining the same level of gene silencing ability. Furthermore, early preclinical data in NHP and porcine models correlated well with murine data, providing additional assurance to this novel strategy.

General Procedures

Lipid Nanoparticle Formulating

Lipid nanoparticles were made by either direct dilution or in-line dilution methods described by Jeffs et al. (see U.S. Pat. No. 9,005,654). Lipid composition typically contained the following lipids in the respective molar ratios, except where otherwise noted: PEG-lipid (PEG2000-C-DMA, 1.1 mol %); Cationic lipid (Compound 13, 54.9 mol %); cholesterol (33.0 mol %); and 1,2-distearoyl-sn-glycero-3-phosphocholine (DSPC, 11.0 mol %). Nucleic acid was solubilized in 20 mM EDTA, pH 4.5. The solutions were combined in a T-connector at a flow rate of 400 mL/min, diluting (in-line or directly into) with PBS at pH 7.4. Ethanol was then removed and carrier buffer replaced with PBS, pH 7.4 by tangential flow ultrafiltration using Midgee hoop cartridges (MW cut off of 500K, GE Healthcare). The LNP were sterile filtered (0.2 µm syringe filter) and sample concentration determined by either DENAX-HPLC or RiboGreen Assay. Particle size and polydispersity were determined using a Malvern Nano Series Zetasizer. Final lipid and steroid concentrations were determined by UPLC.

Animal Models

LPS-Primed Cytokine Mouse Model

Female ICR mice (n=5 per group, 5-6 weeks old) are pre-treated with 0.05 mg/kg of lipopolysaccharide (LPS) at time=0 to prime the immune system. At t=2 h they receive LNP at a 1 mg/kg dose by intravenous administration. Blood samples are collected into sodium EDTA microtainer tubes at 4 h post-LNP treatment (terminal bleed) and are processed to plasma by centrifugation at 16000×g for 5 min at 16° C. Plasma samples are analyzed for Interleukin-1 beta (IL-1β), Interleukin-6 (IL-6), and Monocyte Chemotactic Protein 1 (MCP-1) cytokine levels by ELISA.

Acute Cytokine Mouse Model

Female ICR mice (n=5 per group, 5-6 weeks old) are treated with 10 mg/kg of LNP by intravenous administration. At 2 h post-treatment, blood is collected into tubes containing 50 mM EDTA via tail nicks and processed to plasma by centrifugation at 16000×g for 5 min at 16° C. At 6 h post-treatment, terminal blood samples are collected into sodium EDTA microtainer tubes and are processed to plasma using the same procedure as above. Plasma samples are analyzed by ELISA for Interleukin-6 (IL-6) and Monocyte Chemotactic Protein 1 (MCP-1) cytokine levels.

Activity Mouse Model

LNP formulated with a siRNA targeting Apolipoprotein B (ApoB) were administered IV to generate dose response curve (typical doses: 0.01 mg/kg to 0.05 mg/kg total siRNA) in female Balb/C mice (n=3 per group, 5-6 weeks old). Terminal time point is at 48 hours post-intravenous administration of LNP. The left liver lobe is collected into RNAlater and assayed for ApoB levels by QuantiGene 2.0 analysis. Results are normalized to the house keeping gene GAPDH.

Example 1

LNP Containing Dexamethasone 21-Palmitate in LPS-Primed Cytokine Mouse Model

Dexamethasone 21-palmitate (Dex-P) is effectively a prodrug of dexamethasone, requiring enzymatic action to release the steroid (Dexamethasone). This is less favorable compared to the steroid in its free form (since it requires conversion to the active form in vivo); however, dexamethasone 21-palmitate has a higher log P than free dexamethasone, facilitating better incorporation into LNP.

Using the base composition described in General Procedures, a titration series of compositions was prepared with a steadily increasing Dex-P content (0.5 mol %, 2 mol %, or 5 mol % Dex-P). Dex-P was simply included as an additional lipid component in the 90% ethanol lipid stock. Particle characteristics were essentially identical to the base composition (Table 1).

TABLE 1

Formulation characteristics of Base Formulation vs Dex-P LNP

| Formulation | Z avg (nm) | PDI | % Encap |
|---|---|---|---|
| Base Formulation | 77 | 0.04 | 98 |
| Base + 5% DexP | 77 | 0.03 | 98 |
| Base + 2% DexP | 77 | 0.02 | 99 |
| Base + 0.5% DexP | 74 | 0.03 | 98 |

The above formulations were tested in the LPS-primed mouse cytokine model described in General Procedures. As an additional control, the Base Formulation was co-administered with free Dexamethasone. The free steroid was administered intravenously at a dose of 0.3 mg/kg (a clinically relevant dose).

ICR mice pre-treated with lipopolysaccharide (LPS) at 0.05 mg/kg induced cytokine response compared to animals pre-treated with PBS. Following intravenous administration of LNP, there were further increases in all 3 cytokines. Representative cytokine data (MCP-1) is shown in Table 2. The cytokine levels were highest for the group treated with the Base Formulation in the absence of steroid. Co-formulating Dex-P with the LNP reduced cytokine levels significantly. Furthermore, the cytokine levels were similar between the low (0.5 mol %) and high (5 mol %) steroid doses when co-formulated in LNP, indicating a potentially saturating effect. With 5 mol % Dex-P incorporated into the LNP, the equivalent dose of free dexamethasone administered in a single intravenous injection was 0.3 mg/kg. The cytokine levels achieved with Dex-P LNP at this dose was similar to co-administering the control LNP with 0.3 mg/kg of free dexamethasone in two separate, consecutive injections.

TABLE 2

MCP-1 ELISA Results of Base Composition vs Dex-P LNP in LPS-primed Cytokine Mouse Model

| Pre-Treatment | Treatment | Average MCP-1 (pg/mL) | Stdev (pg/mL) |
|---|---|---|---|
| PBS | PBS | 95 | 35 |
| LPS | PBS | 4170 | 2345 |
| LPS | 1.1:55 ('Base') | 39403 | 12135 |
| LPS | Base + 5% DexP | 8978 | 5817 |
| LPS | Base + 2% DexP | 13039 | 4824 |
| LPS | Base + 0.5% DexP | 12899 | 4705 |
| LPS | 1.1:55 0.3 mg/kg ('Base') Free Dex | 8801 | 4327 |

Example 2

LNP Containing Dexamethasone 21-Palmitate in Acute Cytokine Mouse Model

The concept of corticosteroid co-formulation was further supported with data from the acute cytokine model. The same formulation panel was tested (dosed at 10 mg/kg in this model) and data again indicated that co-formulated Dex-P LNP is an effective means of reducing immune-stimulation, achieving similar cytokine levels to co-administering LNP with free dexamethasone, at the same or lower doses (Table 3).

TABLE 3

MCP-1 ELISA Results of Base Composition vs Dex-P LNP in Acute Cytokine Mouse Model

| | 2 h | | 6 h | |
|---|---|---|---|---|
| Treatment | Average MCP-1 (pg/mL) | Stdev (pg/mL) | Average MCP-1 (pg/mL) | Stdev (pg/mL) |
| PBS | 88 | 14 | 104 | 18 |
| 1.1:55 ('Base') | 3804 | 1145 | 1377 | 553 |
| Base + 5% DexP | 104 | 24 | 118 | 43 |
| Base + 2% DexP | 148 | 66 | 139 | 84 |
| Base + 0.5% DexP | 193 | 62 | 203 | 61 |
| 1.1:55 ('Base') 0.3 mg/kg FreeDex | 190 | 132 | 252 | 155 |

Example 3

LNP Containing Reduced Dexamethasone 21-Palmitate in LPS Primed Model

The concentrations of Dex-P were titrated down further (to 0.5 mol %, 0.1 mol % and 0.01 mol %). Post-formulation analysis by UPLC indicated that Dex-P was readily incorporated into the particles. Particle characteristics were comparable between LNP formulations (Table 4).

TABLE 4

Formulation characteristics of Base Formulation vs Dex-P LNP

| Formulation | Z-avg (nm) | PDI | % Encap |
|---|---|---|---|
| Base Formulation | 75 | 0.10 | 99 |
| Base + 0.5% DexP | 74 | 0.03 | 99 |
| Base + 0.1% DexP | 75 | 0.07 | 98 |
| Base + 0.01% DexP | 74 | 0.01 | 98 |

Results for a representative cytokine readout (MCP-1) are shown in Table 5. A correlation between Dex-P concentration and cytokine levels was observed (more Dex-P gave a better reduction in cytokines). The 0.5% Dex-P LNP is equivalent to approximately a 0.03 mg/kg dose of free Dexamethasone. Data comparing these two groups showed that the reduction in cytokines is significantly better when the corticosteroid was incorporated in the LNP. In fact, this LNP (0.5% Dex-P) actually performed as well as a 0.3 mg/kg dose of free Dexamethasone—a 10-fold greater dose of corticosteroid. It was hypothesized that this surprising result may be due to much more effective, 'targeted delivery' of the corticosteroid. Immune cells which take up LNP, and may otherwise have triggered an immune response, are simultaneously receiving the immune suppressive corticosteroid.

TABLE 5

MCP-1 ELISA Results of Base Composition vs Dex-P LNP in LPS-primed Cytokine Mouse Model

| Pre-Treatment | Treatment | Average MCP-1 (pg/mL) | Stdev (pg/mL) |
|---|---|---|---|
| PBS | PBS | 135 | 21 |
| LPS | PBS | 3821 | 432 |
| LPS | 1.1:55 ('Base') | 28020 | 6224 |
| LPS | Base + 0.5% DexP | 12304 | 7171 |
| LPS | Base + 0.1% DexP | 24119 | 9935 |
| LPS | Base + 0.01% DexP | 29276 | 5392 |
| LPS | 1.1:55 ('Base') 0.3 mg/kg Free Dex | 13982 | 4350 |
| LPS | 1.1:55 ('Base') 0.03 mg/kg Free Dex | 27893 | 7566 |
| LPS | 1.1:55 ('Base') 0.006 mg/kg Free Dex | 23901 | 4254 |

Example 4

Activity of LNP Co-Formulated with Dex-P

To verify that incorporation of Dex-P into LNP did not impact potency, formulations were assessed in the Activity Mouse Model described in General Procedures. Samples containing various amounts of Dex-P were tested at 2 doses; 0.025 mg/kg and 0.05 mg/kg. Similar silencing activity was observed for all formulations at each dose. The Base Formulation containing 0.5% Dex-P and a non-targeting control siRNA (siLuc-2) was included as a negative control. No silencing is expected or observed with this payload. Results are shown in Table 6.

TABLE 6

ApoB Silencing Activity of 1.1:55 Base vs LNP co-formulated with Dex-P in Mouse Model

| Treatment | Dose (mg/kg) | % PBS | % Error |
|---|---|---|---|
| PBS | n/a[1] | 100 | 21 |
| 1.1:55 ('Base') | 0.025 | 55 | 6 |
| | 0.05 | 47 | 7 |
| Base + 5% Dex-P | 0.025 | 81 | 12 |
| | 0.05 | 46 | 5 |
| Base + 2.5% Dex-P | 0.025 | 57 | 19 |
| | 0.05 | 34 | 6 |
| Base + 0.5% Dex-P | 0.025 | 54 | 8 |
| | 0.05 | 35 | 10 |
| Base + 0.1% Dex-P | 0.025 | 67 | 8 |
| | 0.05 | 36 | 14 |
| Base + Free Dex | 0.025 | 64 | 15 |
| | 0.05 | 29 | 6 |
| Base + 0.5% Dex-P (siLuc-2) | 0.025 | 86 | 8 |
| | 0.05 | 92 | 20 |

[1] PBS administered intravenously at 10 mL/kg.

Example 5

LNP Containing Clobetasol in LPS Primed Mouse Model

It was then attempted to co-formulate the corticosteroid clobetasol-17-propionate (clobetasol) into LNP, again to study its ability to suppress inflammatory responses to the particle. A 40 mM acetate, pH 4.5 buffer was used to solubilize the nucleic acid. Final lipid composition is shown in Table 7. Clobetasol, having a lower log P (~3.5), didn't incorporate as readily into the LNP as Dex-P (log P~9). Therefore an 8-fold greater concentration of clobetasol than was actually desired in the end product was input into the process. Analysis by UPLC confirmed incorporation of clobetasol.

TABLE 7

Lipid composition of 1.1:55 Base vs LNP containing Clobetasol

| | Lipid Composition (mol %) | | | | |
|---|---|---|---|---|---|
| | PEG2000-C-DMA | Compound 13 | Cholesterol | Phospholipid [1] | Clobetasol |
| 1.1:55 ('Base') | 1.1 | 55 | 33 | 11 | — |
| Base + 1% Clobetasol | 1.1 | 55 | 33 | 11 | 1 |

[1] 1,2-di-O-octadecyl-sn-glycero-3-phosphocholine used instead of DSPC in LNP containing Clobetasol As outlined in Table 8, formulation characteristics were comparable between the two compositions. Particle size, polydispersity and payload encapsulation indicated uniform particle populations.

TABLE 8

Characterization of 1.1:55 Base vs LNP containing Clobetasol

| Formulation | Z avg (nm) | PDI | % Encap |
|---|---|---|---|
| Base Formulation | 79 | 0.04 | 96 |
| Base + 1% clobetasol | 65 | 0.04 | 98 |

The two compositions were assessed in the LPS-primed mouse model. A representative cytokine readout (MCP-1) is shown in Table 9. The inflammatory response to the LNP is significantly reduced with the clobetasol LNP. The MCP-1 levels are similar to LNP containing Dex-P; however, clobetasol is not a pro-drug, and does not rely on enzymatic action for activation. This is a significant advantage over Dex-P as this corticosteroid would work spontaneously upon delivery of the LNP to its targeted site of action.

TABLE 9

MCP-1 ELISA Results of Base Composition vs LNP containing Clobetasol in LPS-primed Cytokine Mouse Model

| Pre-Treatment | Treatment | Average MCP-1 (pg/mL) | Stdev (pg/mL) |
|---|---|---|---|
| PBS | PBS | 201 | 13 |
| LPS | PBS | 3877 | 2138 |
| LPS | 1.1:55 ('Base') | 49069 | 9784 |
| LPS | Base + 1% Clobetasol | 11550 | 7598 |

Example 6

LNP Containing Clobetasol in Acute Cytokine Mouse Model

The same LNP compositions (Base and Base+Clobetasol) were tested in the acute cytokine model. MCP-1 and IL-6 cytokine levels were measured at both 2 h and 6 h time points. Both cytokines reported significantly lower levels for the co-formulated clobetasol LNP. The latter formulation reported only baseline levels of IL-6 at both time points (Table 10).

TABLE 10

IL-6 ELISA Results of Base Composition vs LNP containing Clobetasol in Acute Cytokine Mouse Model

|  | 2 h | | 6 h | |
|---|---|---|---|---|
| Treatment | Average IL-6 (pg/mL) | Stdev (pg/mL) | Average IL-6 (pg/mL) | Stdev (pg/mL) |
| PBS | 17 | 4 | 10 | 7 |
| 1.1:55 ('Base') | 2232 | 493 | 152 | 137 |
| Base + 1% Clobetasol | 27 | 13 | 5 | 2 |

An expanded acute cytokine study was performed with more time points, to ensure that the peak cytokine response had not simply shifted to an earlier or later time point with the clobetasol LNP. Peak cytokine response is usually observed at 2 h post-LNP treatment in this model. Results confirmed that this steroid was effective at suppressing the immune response throughout the time course of the study (Table 11).

TABLE 11

MCP-1 ELISA Results of Base Composition vs LNP containing Clobetasol in an Expanded Time Course Study, Acute Cytokine Mouse Model

|  | PBS | | 1.1:55 ('Base') | | Base + 1% Clobetasol | |
|---|---|---|---|---|---|---|
| Time Point (h) | Avg MCP-1 (pg/mL) | Stdev (pg/mL) | Avg MCP-1 (pg/mL) | Stdev (pg/mL) | Avg MCP-1 (pg/mL) | Stdev (pg/mL) |
| 0.25 | 74 | 10 | 83 | 13 | 68 | 5 |
| 0.5 | 150 | 52 | 314 | 196 | 75 | 9 |
| 1 | 91 | 7 | 356 | 202 | 99 | 7 |
| 2 | 100 | 12 | 1447 | 602 | 248 | 198 |
| 3 | 98 | 21 | 946 | 815 | 186 | 156 |
| 4 | 113 | 22 | 646 | 411 | 191 | 99 |
| 6 | 84 | 16 | 735 | 561 | 106 | 24 |

Example 7

Activity of LNP Containing Clobetasol in a Mouse Dose Response Study

To verify that incorporation of clobetasol into LNP and the slight modifications to the process did not impact potency, formulations were assessed in the Activity Model described in General Procedures. Similar silencing activity was observed for both formulations at each dose (Table 12). This highlights that the clobetasol LNP have a dramatically improved Therapeutic Index; they have equal potency, but far superior tolerability.

TABLE 12

ApoB Silencing Activity of 1.1:55 Base Composition vs LNP containing Clobetasol

| Treatment | Dose (mg/kg) | % PBS | % Error |
|---|---|---|---|
| PBS | n/a[1] | 100 | 20 |
| 1.1:55 (‘Base’) | 0.01 | 45 | 7 |
| | 0.025 | 21 | 1 |
| | 0.05 | 12 | 1 |
| Base + 1% Clobetasol | 0.01 | 44 | 11 |
| | 0.025 | 18 | 5 |
| | 0.05 | 9 | 1 |

[1]PBS administered intravenously at 10 mL/kg.

Example 8

Immune Suppression with LNP Containing Ciclesonide

Next the corticosteroid Ciclesonide was tested. Final lipid composition is shown in Table 13. Analysis by UPLC confirmed incorporation of Ciclesonide. Ciclesonide has a log P of ~5.3 and incorporated readily into the particle.

TABLE 13

Lipid composition of 1.1:55 Base vs LNP containing Clobetasol

| | Lipid Composition (mol %) | | | | |
|---|---|---|---|---|---|
| | PEG2000-C-DMA | Compound 13 | Choles-terol | DSPC | Icleso-nide |
| Base Formulation | 1.1 | 55 | 33 | 11 | — |
| Base + 2% Ciclesonide | 1.1 | 55 | 33 | 11 | 2 |

As outlined in Table 14, formulation characteristics were comparable between the two compositions. Particle size, polydispersity and payload encapsulation indicated uniform particle populations.

TABLE 14

Characterization of 1.1:55 Base vs LNP containing Clobetasol

| Formulation | Z-avg (nm) | PDI | % Encap |
|---|---|---|---|
| Base Formulation | 78 | 0.06 | 96 |
| Base + 2% Ciclesonide | 77 | 0.04 | 97 |

The Ciclesonide LNP were tested in the LPS-primed mouse model, and compared to the Base formulation as well as Dex-P LNP. The Ciclesonide LNP also exhibited a significantly reduced inflammatory cytokine response, compared to the Base formulation. Data for a representative cytokine (MCP-1) is shown in Table 15.

TABLE 15

MCP-1 ELISA Results of Base Composition vs LNP containing Steroid in LPS-primed Cytokine Mouse Model

| Pre-Treatment | Treatment | Average MCP-1 (pg/mL) | Stdev (pg/mL) |
|---|---|---|---|
| PBS | PBS | 170 | 9 |
| LPS | PBS | 6012 | 2774 |
| LPS | 1.1:55 (‘Base’) | 54909 | 18542 |
| LPS | Base + 2% Dex-P | 26468 | 4561 |
| LPS | Base + 2% Ciclesonide | 17913 | 4352 |

Example 9

Activity of LNP Containing Ciclesonide

Ciclesonide LNP were also assessed in the Activity Model described in General Procedures. Like Dex-P LNP, the Ciclesonide LNP exhibited similar potency to the Base Formulation (Table 16).

TABLE 16

ApoB Silencing Activity of 1.1:55 Base Composition
vs LNP containing Ciclesonide and Dex-P

| Treatment | Dose (mg/kg) | % PBS | % Error |
|---|---|---|---|
| PBS | n/a[1] | 100 | 17 |
| 1.1:55 ('Base') | 0.01 | 31 | 3 |
|  | 0.025 | 16 | 2 |
|  | 0.05 | 12 | 2 |
| Base + 2% Dex-P | 0.01 | 43 | 11 |
|  | 0.025 | 17 | 9 |
|  | 0.05 | 17 | 3 |
| Base + 2% Ciclesonide | 0.01 | 48 | 16 |
|  | 0.025 | 27 | 2 |
|  | 0.05 | 13 | 4 |

[1]PBS administered intravenously at 10 mL/kg.

Example 10

LNP Containing Clobetasol Reduced
Immune-Stimulation in Non-Human Primates

An intravenous pharmacology study was conducted in cynomolgus monkeys to evaluate a clobetasol LNP formulation, and compared to a control formulation (the 'Base Formulation' used previously). Similar to Example 5, an 8-fold greater concentration of clobetasol was input into the process to get the desired 1 mol % in the final composition (Table 17). A 40 mM acetate, pH 4.5 buffer was used to solubilize the nucleic acid.

TABLE 17

Lipid composition of 1.1:55 Base vs LNP containing Clobetasol

| | Lipid Composition (mol %) | | | |
|---|---|---|---|---|
| | PEG-2000-C-DMA | Compound 13 | Cholesterol | DSPC | Clobetasol |
| 1.1:55 ('Base') | 1.1 | 55 | 33 | 11 | — |
| Base + 1% Clobetasol | 1.0 | 61 | 18.5 | 18.5 | 1 |

LNP formulation was administered to a group of four cynomolgus monkeys (Cambodian origin; 2 males, 2 females, 2-5 years of age) via a 60 minute intravenous infusion at a dose of 2.0 mg/kg total siRNA. Blood draws at pre-dose and 2, 6, and 24 h post-infusion were tested for a panel of inflammatory markers. The clobetasol LNP demonstrated a significant reduction in a number of inflammatory markers, further confirming the effectiveness of this strategy. Table 18 compares MCP-1, IL-6, and IL-1ra (Interleukin-1 receptor antagonist) levels between the two compositions at 6 hours post-infusion.

TABLE 18

Comparison of Inflammatory Response (at 6 hours post-infusion)
to Base Composition vs LNP containing Clobetasol in
Cynomolgus Monkeys

| Treatment | Avg MCP-1 (pg/mL) | Stdev (pg/mL) | Avg IL-6 (pg/mL) | Stdev (pg/mL) | Avg IL-1ra (pg/mL) | Stdev (pg/mL) |
|---|---|---|---|---|---|---|
| Saline | 660 | 334 | 26 | 31 | 420 | 344 |
| 1.1:55 ('Base') | 5548 | 7280 | 703 | 1164 | 2571 | 3114 |
| Base + 1% Clobetasol | 214 | 28 | 7 | 3 | 204 | 160 |

Example 11

An Examination of the Cardiovascular Effects of a
Single Infusion of LNP Formulations in
Anesthetized Female Gottingen Mini-Pigs Test article-related effects of a single 1-hour infusion of LNP formulations on hemodynamic parameters and inflammatory biomarkers were evaluated in anesthetized female Gottingen mini-pigs. LNP were formulated with the compositions in Table 19. Similar to Example 5, an 8-fold greater concentration of clobetasol was input into the process to get the desired 1 mol % in the final composition. A 40 mM acetate, pH 4.5 buffer was used to solubilize the nucleic acid.

TABLE 19

Lipid composition of 1.1:55 Base vs LNP containing Clobetasol

| | Lipid Composition (mol %) | | | | |
|---|---|---|---|---|---|
| | PEG-2000-C-DMA | Compound 13 | Cholesterol | DSPC | Clobetasol |
| 1.1:55 ('Base') | 1.1 | 55 | 33 | 11 | — |
| Base + 1% Clobetasol | 1.0 | 61 | 18.5 | 18.5 | 1 |

Three (3) naïve mini-pigs were surgically instrumented and baseline data was collected prior to a single administration of vehicle (saline), base LNP, or clobetasol LNP via a 60 minute intravenous infusion. LNP formulations were administered at a dose of 0.3 mg/kg total nucleic acid. Just prior to the first infusion, and at approximately 5, 60, 90, 120, 180, and 240 minutes after the start of infusion, a blood sample was taken, processed to plasma and serum, and analyzed for cytokines and thromboxane (11-dehydrothromboxane B2). Hemodynamic data was collected continuously throughout the experiment, for a total time period of 4 hours. At 4 hours post-infusion, pigs were euthanized under anesthesia via barbiturate overdose.

Treatment with the Base Formulation resulted in considerable, measureable increases in thromboxane (Table 20) and cytokines (Table 21) with the Base Formulation. Furthermore, hemodynamic changes such as increases in pulmonary artery pressure were observed (Table 22). These parameters are all indicative of an inflammatory response to the Base LNP that is suppressed by incorporation of clobetasol into the LNP formulation. This is likely a glucocorticoid-mediated inhibition of phospholipase A2 and transrepression of inflammatory cytokine transcription when the animals are treated with co-formulated steroid LNP.

TABLE 20

Comparison of Thromboxane Levels between 1.1:55 Base and LNP containing Clobetasol in Anesthetized Mini-Pigs
TXB2 Change from Baseline (pg/mL)

| | | Time Relative to Start of Infusion (minutes) | | | | | | |
|---|---|---|---|---|---|---|---|---|
| | | −15 | 5 | 60 | 90 | 120 | 180 | 240 |
| Saline | Mean | 0.0 | −9.2 | 1.5 | −13.0 | −13.0 | −7.0 | −9.0 |
| | sem | 0.0 | 3.5 | 3.6 | 2.3 | 2.3 | 1.5 | 2.2 |
| 1.1:55 ('Base') | Mean | 0.0 | 4.8 | 21.5 | 24.4 | 19.4 | 14.0 | 4.8 |
| | sem | 0.0 | 2.0 | 1.4 | 8.1 | 7.2 | 6.6 | 2.7 |
| Base + 1% | Mean | 0.0 | −7.3 | 9.9 | −0.9 | −0.1 | −7.3 | −7.3 |
| Clobetasol | sem | 0.0 | 7.3 | 8.5 | 0.9 | 7.3 | 7.3 | 7.3 |

TABLE 21

Comparison of IL-6 Cytokine Levels between 1.1:55 Base and LNP containing Clobetasol in Anesthetized Mini-Pigs
Fold Change in IL-6 from Baseline

| | | Time Relative to Start of Infusion (minutes) | | | | | | |
|---|---|---|---|---|---|---|---|---|
| | | −15 | 5 | 60 | 90 | 120 | 180 | 240 |
| Saline | Mean | 1.0 | 0.9 | 3.3 | 5.4 | 8.0 | 16.6 | 40.3 |
| | sem | 0.0 | 0.1 | 1.5 | 2.3 | 1.6 | 1.4 | 20.0 |
| 1.1:55 ('Base') | Mean | 1.0 | 1.0 | 4.2 | 9.0 | 21.4 | 76.5 | 210.5 |
| | sem | 0.0 | 0.0 | 3.2 | 8.0 | 15.9 | 39.9 | 58.9 |
| Base + 1% | Mean | 1.0 | 0.9 | 3.9 | 10.0 | 15.8 | 1.0 | 0.4 |
| Clobetasol | sem | 0.0 | 0.5 | 2.9 | 9.0 | 14.7 | 0.6 | 0.3 |

TABLE 22

Comparison of Mean Pulmonary Artery Pressure (PAP) between 1.1:55 Base and LNP containing Clobetasol in Anesthetized Mini-Pigs
Mean PAP - Change from Baseline (mmHg)

| | | Time Relative to Start of Infusion (minutes) | | | | | | | | |
|---|---|---|---|---|---|---|---|---|---|---|
| | | −15 | 0 | 15 | 30 | 60 | 90 | 120 | 150 | 180 | 240 |
| Saline | Mean | 0 | 0 | 0 | 0 | 0 | 0 | 0 | 0 | 0 | 0 |
| | sem | 0 | 0 | 0 | 1 | 1 | 1 | 1 | 1 | 1 | 1 |
| 1.1:55 ('Base') | Mean | 0 | 0 | 4 | 1 | 4 | 6 | 4 | 3 | 2 | 1 |
| | sem | 0 | 0 | 2 | 0 | 2 | 3 | 2 | 2 | 1 | 1 |
| Base + 1% | Mean | 0 | 0 | 4 | 1 | 1 | 1 | 1 | 1 | 0 | 1 |
| Clobetasol | sem | 0 | 0 | 0 | 0 | 1 | 1 | 1 | 0 | 0 | 1 |

Example 12

Co-Formulated Clobetasol is Effective at Reducing Immune Response to LNP Bearing mRNA Payloads The concept of steroid co-formulation with LNP was further tested bearing an mRNA payload. This example demonstrates how a reduction in mRNA-LNP immune stimulation can be achieved by incorporation of the corticosteroid clobetasol.

LNP (PL-containing & PL-free) were prepared by the direct dilution method described by Jeffs et al. In brief, lipid stocks were prepared in 100% ethanol at a total lipid concentration of 6-7 mg/mL. An mRNA transcript encoding Luciferase (TriLink BioTechnologies), a reporter gene, was solubilized in 40 mM EDTA, pH 4.5 at 0.366 mg/mL. Equal volumes of these solutions were combined in a T-connector at a flow rate of 250 mL/min, immediately diluting into PBS (4× volume of lipid stock) at pH 7.4. Ethanol was then removed and carrier buffer was replaced with PBS by dialysis (Slide-A-Lyzer unit, MWCO 10 k), dialyzing overnight against 100 volumes of PBS. Following dialysis the formulations were concentrated to ~0.3 mg/mL using VivaSpin concentrator units (MWCO 100,000). As with siRNA formulations, the low log P of clobetasol necessitated it being input at ~8× the amount desired in the final composition, as only ~15% incorporates in the LNP particles. The remainder is lost during dialysis. The LNP samples were sterile filtered (0.2 µm syringe filter) and sample concentration determined by RiboGreen Assay. Particle size and polydispersity were determined using a Malvern Nano Series Zetasizer. The amount of clobetasol and other lipids in the final composition was determined by UPLC and is displayed in Table 23.

TABLE 23

Formulation characteristics of Base Formulation vs LNP containing Clobetasol

| | Lipid Composition (mol %) | | | | | Characterization | | |
|---|---|---|---|---|---|---|---|---|
| | PEG2000-C-DMA | Cmpd 13 | Cholesterol | Phospholipid[1] | Clobetasol | Size (nm) | PDI | % Encap |
| 1.6:55 Base | 1.6 | 55 | 33 | 11 | 0 | 73 | 0.07 | 97 |
| Base + 1.0% Clobetasol | 1.6 | 55 | 33 | 11 | 1 | 67 | 0.04 | 96 |

[1]1,2-di-O-octadecyl-sn-glycero-3-phosphocholine

Prior to injection formulations were diluted to 0.05 mg/mL. Balb/c mice (n=5) were injected at 0.5 mg/kg (mRNA) via the intravenous route through the lateral tail. Four hours following injection the animals were euthanized with a lethal dose of ketamine/xylazine. A small amount (20 µL) of the terminal blood was collected into a tube containing 5 µL of 50 mg/L heparin, while the rest of the blood was collected into sodium EDTA microtainer tubes. All of these tubes were centrifuged for 5 min at 16000×g & 16° C. to isolate plasma. A small portion (~200 mg) of the left lateral lobe of the liver was collected and stored overnight in RNALater @4° C.

The heparin plasma (diluted 1:4000 with ELISA Diluent) was used in a standard Murine EPO ELISA analysis (kit from R&D Systems). As shown in Table 24, the incorporation of clobetasol within the mRNA-LNP possibly resulted in a slight reduction in potency, though likely within the boundary of experimental variability. The regular level of EPO seen within the plasma of these mice is 0.1-0.2 ng/mL. Therefore, the incorporation of clobetasol within the mRNA-LNP does not really affect the efficacy of the formulation.

TABLE 24

Efficacy of Murine mEPO-LNP in Liver 4 h Post-IV Administration of Base Composition vs LNP containing Clobetasol

| Treatment | mEPO (ng/mL) | Stdev (ng/mL) |
|---|---|---|
| 1.6:55 ('Base') | 6041 | 1305 |
| Base + Clobetasol | 4438 | 781 |

To assess the effect on immune stimulation, EDTA plasma samples were diluted (1:8) and analyzed for cytokines (MCP-1 and IL-6) by ELISA (ELISA assays and capture & detection antibodies from BD Biosciences). Table 25 demonstrates that cytokine production is significantly reduced when clobetasol is incorporated in the formulation.

TABLE 25

MCP-1 and IL-6 ELISA Results of Base Compositions vs LNP containing Clobetasol

| | MCP-1 | | IL-6 | |
|---|---|---|---|---|
| Treatment | Average (pg/mL) | Stdev (pg/mL) | Average (pg/mL) | Stdev (pg/mL) |
| PBS | 57 | 4 | 15 | 3 |
| 1.6:55 ('Base') | 5911 | 3592 | 353 | 194 |
| Base + Clobetasol | 479 | 146 | 78 | 24 |

The liver IFIT (Interferon Induced proteins with Tetratricopeptide repeats) response to the two formulations was also measured. The IFIT biomarker indicates a type I interferon response to the payload. Liver samples (20-25 mg) were homogenized and the QuantiGene 2.0 assay (Affymetrix) used to assess IFIT levels in the liver (normalized to the housekeeping gene GAPDH). Results are plotted as a fold increase over the PBS control group, and demonstrate that clobetasol co-formulation is also effective in suppressing the IFIT response to the mRNA payload (Table 26).

TABLE 26

Hepatic IFIT Induction of Base Composition vs LNP containing Clobetasol

| Treatment | Fold Increase Over PBS | Stdev |
|---|---|---|
| 1.6:55 ('Base') | 591 | 116 |
| Base + Clobetasol | 334 | 31 |

Taken together these results demonstrate that the incorporation of clobetasol into the LNP particle significantly abrogates the immune stimulation to mRNA-LNP, and an increase in the Therapeutic Index is observed.

Example 13

Co-Formulated Dexamethasone Palmitate is Effective at Reducing Immune Response to LNP Bearing mRNA Payloads This example demonstrates how a steroid pro-drug, dexamethasone 21-palmitate (Dex-P), can also be used to reduce inflammatory responses to LNP bearing and mRNA payload. An mRNA-LNP containing Dex-P was formulated as described in Example 12, with the compositions described in Table 27. A murine EPO mRNA transcript (TriLink BioTechnologies) was used for the payload.

TABLE 27

Formulation characteristics of Base Formulation vs LNP containing Dex-P

| | Lipid Composition (mol %) | | | | | Characterization | | |
|---|---|---|---|---|---|---|---|---|
| | PEG2000-C-DMA | Cmpd 13 | Cholesterol | DSPC | Dex-P | Size (nm) | PDI | % Encap |
| 1.1:55 Base | 1.1 | 55 | 33 | 11 | 0 | 85 | 0.06 | 97 |
| Base + 2% Dex-P | 1.1 | 55 | 33 | 11 | 2 | 81 | 0.05 | 97 |

The formulations were injected intravenously at a dose of 0.5 mg/kg (total mRNA) into Balb/C mice (n=5). Six hours following injection, the animals were euthanized with a lethal dose of ketamine/xylazine. A small amount (75 µL) of the terminal blood was collected into a tube containing 5 µL of 50 mg/L heparin, while the rest of the blood was collected into sodium EDTA microtainer tubes. Blood samples were centrifuged for 5 min at 16000×g & 16° C. to isolate plasma.

The heparin plasma (diluted 1:4000 with ELISA Diluent) was analyzed by ELISA for EPO levels (kit from R&D Systems). As shown in Table 28, the incorporation of Dex-P within the mRNA-LNP possibly resulted in an increase in potency, though possibly within experimental variability.

TABLE 28

Efficacy of Murine mEPO-LNP in Liver 4 h Post-IV Administration of Base Composition vs LNP containing Dex-P

| Treatment | mEPO (ng/mL) | Stdev (ng/mL) |
|---|---|---|
| 1.1:55 ('Base') | 2009 | 1179 |
| Base + 2% Dex-P | 3659 | 1313 |

EDTA plasma was analyzed by ELISA (BD Biosciences) for cytokine levels (MCP-1 & IL-6). Table 29 demonstrates that incorporation of Dex-P into the mRNA-LNP yields a marked reduction in cytokine levels.

TABLE 29

MCP-1 and IL-6 ELISA Results of Base Composition vs LNP containing Dex-P

| | MCP-1 | | IL-6 | |
|---|---|---|---|---|
| Treatment | Average (pg/mL) | Stdev (pg/mL) | Average (pg/mL) | Stdev (pg/mL) |
| PBS | 36 | 15 | 27 | 13 |
| 1.1:55 ('Base') | 4471 | 1279 | 515 | 194 |
| Base + 2% Dex-P | 1281 | 737 | 83 | 16 |

This data demonstrates that incorporation of dexamethasone-palmitate reduced the inflammatory response to mRNA-LNP, and results significantly improved therapeutic index for mRNA-LNP.

Examples 14-20

Reduced or Absent Phospholipid and High PEG in LNP

The presence of phospholipid can reduce the shelf-life of lipid nanoparticles (LNPs) because the phosphate ester bond is thought to be quite labile. Most or all the phospholipid was removed from LNPs to test the effect on shelf-life of LNP comprising mRNA. During these experiments, it was discovered that the immunogenicity of the formulations was greatly reduced without affecting potency. As described herein, certain embodiments of the present invention are directed to LNPs possessing the combination of low or absent phospholipid and higher than usual PEG. Interestingly, the combination of low phospholipid and high mol percent PEG reduces immunostimulation for mRNA more effectively than for siRNA.

In certain embodiments, the amount of PEG is at least 3 mole percent (e.g., at least 3.1 mole percent, at least 3.2 mole percent, at least 3.3 mole percent, at least 3.4 mole percent, at least 3.5 mole percent, at least 3.6 mole percent, at least 3.7 mole percent, at least 3.8 mole percent, at least 3.9 mole percent, at least 4 mole percent). With respect to phospholipid, in certain embodiments, no phospholipid is used in the practice of the invention. In certain embodiments, the lipid particle comprises less than 2 mole percent phospholipid, e.g., 1.9 mol % phospholipid, 1.8 mol % phospholipid, 1.7 mol % phospholipid, 1.6 mol % phospholipid, 1.5 mol % phospholipid, 1.4 mol % phospholipid, 1.3 mol % phospholipid, 1.2 mol % phospholipid, 1.1 mol % phospholipid, 1.0 mol % phospholipid, 0.9 mol % phospholipid, 0.8 mol % phospholipid, 0.7 mol % phospholipid, 0.6 mol % phospholipid, 0.5 mol % phospholipid, 0.4 mol % phospholipid, 0.3 mol % phospholipid, 0.2 mol % phospholipid, 0.1 mol % phospholipid, or 0.0% phospholipid, e.g., less than 1.9 mol % phospholipid, less than 1.8 mol % phospholipid, less than 1.7 mol % phospholipid, less than 1.6 mol % phospholipid, less than 1.5 mol % phospholipid, less than 1.4 mol % phospholipid, less than 1.3 mol % phospholipid, less than 1.2 mol % phospholipid, less than 1.1 mol % phospholipid, less than 1.0 mol % phospholipid, less than 0.9 mol % phospholipid, less than 0.8 mol % phospholipid, less than 0.7 mol % phospholipid, less than 0.6 mol % phospholipid, less than 0.5 mol % phospholipid, less than 0.4 mol % phospholipid, less than 0.3 mol % phospholipid, less than 0.2 mol % phospholipid, less than 0.1 mol % phospholipid.

General Procedures

Lipid Nanoparticle Formulating

LNP formulations were prepared by the LipoMixer method described by Jeffs et al, using either direct dilution or in-line dilution. Lipid compositions were as described, typically comprising 3 or 4 lipids in the molar ratios described. Lipids were solubilized in 100% ethanol at a total lipid concentration of approx. 12 mg/mL. Nucleic acid was solubilized in 20 mM EDTA, pH 4.5 when phospholipid is present in the LNP and in 40 mM EDTA, pH 4.5 in the absence of phospholipid. Equal volumes of these solutions were combined in a T-connector at a flow rate of 400 mL/min, immediately diluting (in-line or directly into) with PBS (4× volume of lipid stock) at pH 7.4. Ethanol was then removed and carrier buffer was replaced with PBS by either dialysis (Slide-A-Lyzer unit, MWCO 10 k) or tangential flow ultrafiltration using Midgee hoop cartridges (MWCO 500 k, GE Healthcare). The LNP samples were sterile filtered (0.2 µm syringe filter) and sample concentration determined by either DENAX-HPLC or RiboGreen Assay.

Particle size and polydispersity were determined using a Malvern Nano Series Zetasizer. Final lipid were determined by UPLC.

Animal Models 3 animal models were used to assess formulations; two models of immune stimulation, and one of potency. Descriptions as follows:

LPS-Primed Cytokine Mouse Model

Female ICR mice (n=5, 5-6 weeks old) are pre-treated with 0.05 mg/kg of lipopolysaccharide (LPS) at time=0 to prime the immune system. At t=2 h they receive LNP at a 1 mg/kg dose by intravenous administration. Blood samples are collected into sodium EDTA microtainer tubes at 4 h post-LNP treatment (terminal bleed) and are processed to plasma by centrifugation at 16000×g for 5 min at 16° C. Plasma samples are analyzed for IL-10, IL-6, and MCP-1 cytokine levels by ELISA.

Acute Cytokine Mouse Model

Female ICR mice (n=5, 5-6 weeks old) are treated with 10 mg/kg of LNP by intravenous administration. At 2 h post-treatment, blood is collected into tubes containing 50 mM EDTA via tail nicks and processed to plasma by centrifugation at 16000×g for 5 min at 16° C. At 6 h post-treatment, terminal blood samples are collected into sodium EDTA microtainer tubes and are processed to plasma using the same procedure as above. Plasma samples are analyzed by ELISA for IL-6 and MCP-1 cytokine levels.

Activity Mouse Model

LNP formulated with a siRNA targeting Apolipoprotein B. Administered IV to generate dose response curve (typical doses: 0.01 mg/kg to 0.05 mg/kg total siRNA encapsulated in LNP) in female Balb/C mice (n=3, 5-6 weeks old). Terminal time point is at 48 hours post-intravenous administration of LNP. The left liver lobe is collected into RNAlater and assayed for ApoB levels by QuantiGene 2.0 analysis. Results are normalized to the house keeping gene GAPDH, and expressed as a % of the PBS control. A group with an ApoB readout that is '20% of PBS' has experienced more profound gene silencing activity than one with '80% of PBS'.

Example 14

Removing Phospholipid from LNP Formulation Reduces Immune Stimulation without Impairing Potency Two LNP formulations were made with an oligonucleotide siRNA payload targeting Apolipoprotein B (ApoB). A 'base' composition, and another with the phospholipid omitted ('phospholipid free', or 'PL-free'). Composition details are outlined in Table 30.

TABLE 30

Lipid composition of a 1.6:55 ('Base') and 1.8:61 ('PL-free') Formulation

| | Lipid Composition (mol %) | | | |
|---|---|---|---|---|
| | PEG-2000-C-DMA | Cationic Compound 13 | Cholesterol | DSPC |
| 1.6:55 ('Base') | 1.6 | 55 | 33 | 11 |
| 1.8:61 ('PL-free') | 1.8 | 61 | 37 | 0 |

In the LPS-primed mouse cytokine model, results clearly indicate that the PL-free LNP is less stimulatory than its parent composition that contains phospholipid (Table 31).

TABLE 31

MCP-1 ELISA Results of Base Composition vs PL-free Composition in LPS-Primed Cytokine Mouse Model

| Pre-Treatment | Treatment | Average MCP-1 (pg/mL) | Stdev (pg/mL) |
|---|---|---|---|
| PBS | PBS | 160 | 11 |
| LPS | PBS | 3237 | 782 |
| LPS | 1.6:55 ('Base') | 35691 | 17620 |
| LPS | 1.8:61 ('PL-free') | 10485 | 3545 |

While reducing inflammatory responses is an important objective, it is also important that potency is not simultaneously impaired. The same panel of LNP were therefore assessed in the ApoB Silencing Activity Model (described under General Procedures). Gene silencing data (Table 32) reveals that removing the phospholipid does not impair potency.

TABLE 32

ApoB Silencing Activity of Base Composition vs PL-free Composition in Activity Mouse Model

| Treatment | Dose (mg/kg) | % PBS | % Error |
|---|---|---|---|
| PBS | n/a[1] | 100 | 9.2 |
| 1.6:55 ('Base') | 0.01 | 45 | 8.6 |
| | 0.025 | 17 | 2.1 |
| | 0.05 | 11 | 1.3 |
| 1.8:61 ('PL-free') | 0.01 | 43 | 8.6 |
| | 0.025 | 29 | 1.5 |
| | 0.05 | 20 | 5.2 |

[1]PBS administered intravenously at 10 mL/kg.

Example 15

Increasing PEG Lipid Content in Phospholipid-Free LNP Resulted in Further Reductions in Cytokine Levels, without Significantly Impacting Potency The following LNP were formulated using an ApoB siRNA payload. Starting from a 'base' composition, the phospholipid was first removed, and then PEG content either doubled or tripled (Table 33):

TABLE 33

Lipid composition of a 1.1:55 Base and PL-free Formulations with Increasing PEG Content

| | Lipid Composition (mol %) | | | |
|---|---|---|---|---|
| | PEG-2000-C-DMA | Cationic Compound 13 | Cholesterol | DSPC |
| 1.1:55 ("Base") | 1.1 | 55 | 33 | 11 |
| 1.1:57 (PL-free) | 1.1 | 57 | 42 | 0 |
| 2.2:56 (PL-free) | 2.2 | 56 | 42 | 0 |
| 3.3:55 (PL-free) | 3.3 | 55 | 41 | 0 |

This panel of LNP was evaluated in the acute mouse cytokine model, with time points at 2 h and 6 h. Again a reduction in cytokines was observed when phospholipid was removed from the composition. Representative cytokine data (MCP-1) is displayed in Table 34. Subsequently, as the PEG content was increased, an even more pronounced reduction in cytokines was observed.

TABLE 34

MCP-1 ELISA Results of 1.1:55 Base Composition vs PL-free Compositions with Increasing PEG Lipid Content in Acute Cytokine Mouse Model

| | 2 h | | 6 h | |
|---|---|---|---|---|
| Treatment | Average MCP-1 (pg/mL) | Stdev (pg/mL) | Average MCP-1 (pg/mL) | Stdev (pg/mL) |
| PBS | 29 | 4 | 36 | 6 |
| 1.1:55 ("Base") | 1967 | 916 | 973 | 801 |
| 1.1:57 (PL-free) | 1072 | 317 | 745 | 342 |
| 2.2:56 (PL-free) | 704 | 147 | 183 | 73 |
| 3.3:55 (PL-free) | 157 | 72 | 45 | 7 |

Interestingly, the potency of these high PEG, PL-free compositions was not significantly impacted (Table 35). In previous experience, formulations with higher PEG content were often found to have compromised activity. For example three (3) related LNP in a similar PEG titration series (Table 36), but with a standard phospholipid content, were evaluated and representative activity data is shown in Table 37. A significant attenuation of activity if observed as PEG content increases. It is therefore surprising to see the significant reduction in cytokines without a more profound, commensurate loss of potency with the high PEG, PL-free systems above.

TABLE 35

ApoB Silencing Activity of 1.1:55 Base Composition vs PL-free Compositions with Increasing PEG Lipid Content in Activity Mouse Model

| Treatment | Dose (mg/kg) | % PBS | % Error |
|---|---|---|---|
| PBS | n/a[1] | 100 | 13 |
| 1.1:55 ('Base') | 0.01 | 37 | 2 |
| | 0.025 | 15 | 2 |
| | 0.05 | 9 | 3 |
| 1.1:57 ('PL-free') | 0.01 | 37 | 7 |
| | 0.025 | 21 | 5 |
| | 0.05 | 12 | 2 |
| 2.2:56 ('PL-free') | 0.01 | 45 | 7 |
| | 0.025 | 20 | 5 |
| | 0.05 | 11 | 2 |
| 3.3:55 ('PL-free') | 0.01 | 48 | 7 |
| | 0.025 | 31 | 8 |
| | 0.05 | 22 | 6 |

[1] PBS administered intravenously at 10 mL/kg.

TABLE 36

Lipid composition of a 1.1:55 Base and PL-containing LNP with Increasing PEG Content

| | Lipid Composition (mol %) | | | |
|---|---|---|---|---|
| | PEG-2000-C-DMA | Cationic Compound 13 | Cholesterol | DSPC |
| 1.1:55 ("Base") | 1.1 | 55 | 33 | 11 |
| 2.2:54 | 2.2 | 54 | 33 | 11 |
| 4.3:53 | 4.3 | 53 | 32 | 11 |

TABLE 37

ApoB Silencing Activity of 1.1:55 Base and PL-containing LNP with Increasing PEG content in Activity Mouse Model

| Treatment | Dose (mg/kg) | % PBS | % Error |
|---|---|---|---|
| PBS | n/a[1] | 100 | 30 |
| 1.1:55 ('Base') | 0.05 | 16 | 5 |
| 2.2:55 | 0.05 | 33 | 3 |
| 4.4:55 | 0.05 | 100 | 38 |

Example 16

Reduction in Phospholipid Content Also Effective at Reducing Inflammatory Response It was hypothesized that it may not be necessary to completely remove phospholipid from the LNP formulation to abrogate immune stimulation, and that this effect can be achieved by simply reducing the PL content. A panel of compositions was prepared (Table 38), using reduced PL content (3 mol % or 8 mol %) vs the parent composition (11 mol %):

TABLE 38

Lipid composition of a 1.1:55 Base and PL-containing LNP with Reduced PL Content

| | Lipid Composition (mol %) | | | |
|---|---|---|---|---|
| | PEG-2000-C-DMA | Cationic Compound 13 | Cholesterol | DSPC |
| 1.1:55 ("Base") | 1.1 | 55 | 33 | 11 |
| 1.1:57 | 1.1 | 57 | 34 | 8 |
| 1.1:55 | 1.1 | 55 | 41 | 3 |
| 1.6:52 | 1.6 | 52 | 39 | 8 |
| 1.6:55 | 1.6 | 55 | 41 | 3 |

These compositions were assessed for immune stimulation in the acute cytokine model. As seen in Table 39, the compositions with reduced phospholipid had a reduced tendency to stimulate the production of cytokines. Further, reduction of phospholipid content had no significant impact on potency (Table 40).

TABLE 39

MCP-1 ELISA Results of 1.1:55 Base vs PL-containing LNP with Reduced PL Content in Acute Cytokine Mouse Model

| | 2 h | | 6 h | |
|---|---|---|---|---|
| Treatment | Average MCP-1 (pg/mL) | Stdev (pg/mL) | Average MCP-1 (pg/mL) | Stdev (pg/mL) |
| PBS | 721 | 487 | 85 | 23 |
| 1.1:55 ("Base") | 3644 | 3250 | 894 | 759 |
| 1.1:57 | 831 | 786 | 388 | 295 |
| 1.1:55 | 335 | 213 | 117 | 39 |
| 1.6:52 | 447 | 174 | 76 | 14 |
| 1.6:55 | 221 | 159 | 91 | 35 |

TABLE 40

ApoB Silencing Activity of 1.1:55 Base Composition vs PL-containing LNP with Reduced PL Content in Mouse Model

| Treatment | Dose (mg/kg) | % PBS | % Error |
|---|---|---|---|
| PBS | n/a[1] | 100 | 6 |
| 1.1:55 ('Base') | 0.01 | 47 | 4 |
| | 0.025 | 18 | 2 |
| 1.1:57 | 0.01 | 37 | 4 |
| | 0.025 | 15 | 2 |
| 1.1:55 | 0.01 | 60 | 13 |
| | 0.025 | 20 | 5 |
| 1.6:52 | 0.01 | 66 | 14 |
| | 0.025 | 27 | 3 |
| 1.6:55 | 0.01 | 46 | 10 |
| | 0.025 | 28 | 2 |

[1] PBS administered intravenously at 10 mL/kg.

Example 17

Removing Phospholipid Reduces Immune Stimulation of LNP Containing mRNA without Impairing Potency This example demonstrates how a reduction in mRNA-LNP immune stimulation can be achieved by removing the phospholipid from the LNP composition (i.e. production of a PL-free mRNA-LNP). The mRNA-LNP formulations were made with the lipid compositions shown in Table 41. Two different base formulations (1.1:55 and 1.6:55) had their phospholipid content removed ('PL-free' compositions), whilst either maintaining or slightly increasing the cholesterol content.

TABLE 41

Formulation characteristics of Base Formulations vs PL-free mLuc-LNP

| | Lipid Composition (mol %) | | | | Characterization | | |
|---|---|---|---|---|---|---|---|
| | PEG-2000-C-DMA | Cmpd 13 | Cholesterol | DSPC | Size (nm) | PDI | % Encap |
| 1.1:55 ('Base') | 1.1 | 55 | 33 | 11 | 104 | 0.01 | 96 |
| 1.6:55 ('Base') | 1.6 | 55 | 33 | 11 | 80 | 0.11 | 99 |
| 1.1:57 ('PL-free') | 1.1 | 57 | 42 | 0 | 106 | 0.08 | 96 |
| 1.7:57 ('PL-free') | 1.7 | 57 | 42 | 0 | 94 | 0.08 | 98 |
| 1.8:61 ('PL-free') | 1.8 | 61 | 37 | 0 | 99 | 0.09 | 95 |

LNP (PL-containing & PL-free) were prepared by the direct dilution method described by Jeffs et al. In brief, lipid stocks were prepared in 100% ethanol at a total lipid concentration of 6-7 mg/mL. An mRNA transcript encoding Luciferase, a reporter gene, was solubilized in 40 mM EDTA, pH 4.5 at 0.366 mg/mL. Equal volumes of these solutions were combined in a T-connector at a flow rate of 250 mL/min, immediately diluting into PBS (4× volume of lipid stock) at pH 7.4. Ethanol was then removed and carrier buffer was replaced with PBS by dialysis (Slide-A-Lyzer unit, MWCO 10 k), dialyzing overnight against 100 volumes of PBS. Following dialysis the formulations were concentrated to ~0.6 mg/mL using VivaSpin concentrator units (MWCO 100,000). The LNP samples were sterile filtered (0.2 μm syringe filter) and sample concentration determined by RiboGreen Assay. Particle size and polydispersity were determined using a Malvern Nano Series Zetasizer.

Prior to injection, LNP were diluted to 0.05 mg/mL. Balb/c mice (n=4) were administered doses (using a volume dose of 10 mL/kg) of 0.5 mg/kg (total mRNA) via lateral tail vein. Animals were euthanized at 4 h post-treatment with ketamine/xylazine. Terminal blood was collected into sodium EDTA microtainer tubes and centrifuged for 5 min at 16000×g & 16° C. to isolate plasma. Liver sections were collected into FastPrep tubes and stored at −80° C. until analysis.

To assess potency, livers were homogenized in 1× Cell Culture Lysis Reagent (CCLR) buffer, then analyzed for luciferase activity using the Luciferase Assay (Promega). As seen in Table 42, there is no detrimental effect on potency when phospholipid was removed from the compositions.

TABLE 42

Luciferase Gene Expression in Liver 6 h Post-IV Administration of Base Compositions vs PL-free mLuc-LNP

| Treatment | Luciferase Activity (ng/g liver) | Stdev (ng/g) |
|---|---|---|
| 1.1:55 ('Base') | 849 | 33 |
| 1.6:55 ('Base') | 1092 | 42 |
| 1.1:57 ('PL-free') | 991 | 27 |
| 1.7:57 ('PL-free') | 846 | 22 |
| 1.8:61 ('PL-free') | 1156 | 65 |

To assess the effect on immune stimulation, plasma samples were diluted (1:8) and analyzed for cytokines (MCP-1 and IL-6) by ELISA (ELISA assays and capture & detection antibodies from BD Biosciences). Table 43 demonstrates that cytokine production is significantly reduced for both of the 'Base' formulations when the phospholipid is removed. The effect on the 1.1:55 Base is particularly profound.

TABLE 43

MCP-1 and IL-6 ELISA Results of Base Compositions vs PL-free mLuc-LNP

| | MCP-1 | | IL-6 | |
|---|---|---|---|---|
| Treatment | Average (pg/mL) | Stdev (pg/mL) | Average (pg/mL) | Stdev (pg/mL) |
| PBS | 28 | 7 | 14 | 5 |
| 1.1:55 ('Base') | 8022 | 3166 | 566 | 177 |
| 1.6:55 ('Base') | 2293 | 293 | 136 | 23 |
| 1.1:57 ('PL-free') | 1434 | 657 | 41 | 29 |
| 1.7:57 ('PL-free') | 705 | 144 | 28 | 6 |
| 1.8:61 ('PL-free') | 540 | 82 | 23 | 6 |

Taken together these results demonstrate that the use of PL-free formulations results in a reduction in the immune stimulation of the formulation compared to PL-containing formulations. Given that the efficacy does not seem to be affected this should result in an increase in the therapeutic index of the mRNA-LNP.

Example 18

Removing Phospholipid Reduces Immune Stimulation of LNP Containing mRNA without Impairing Potency The result in Example 17 was further corroborated with a subset of the compositions formulated with two different mRNA transcripts, mLuc (Table 44a) & mEPO (Table 44b). Transcripts used encoded either luciferase (reporter gene) or erythropoietin (a hormone that controls erythropoiesis, or red blood cell production).

TABLE 44a

Formulation characteristics of 1.6:55 Base Formulation vs PL-free mLuc-LNP

| | Lipid Composition (mol %) | | | | Characterization | | |
|---|---|---|---|---|---|---|---|
| | PEG-2000-C-DMA | Compound 13 | Cholesterol | DSPC | Size (nm) | PDI | % Encap |
| 1.6:55 ('Base') | 1.6 | 55 | 33 | 11 | 77 | 0.10 | 95 |
| 1.7:57 ('PL-free') | 1.7 | 57 | 42 | 0 | 80 | 0.06 | 93 |
| 1.8:61 ('PL-free') | 1.8 | 61 | 37 | 0 | 90 | 0.06 | 91 |

TABLE 44b

Formulation characteristics of 1.6:55 Base Formulation vs PL-free mEPO-LNP

| | Lipid Composition (mol %) | | | | Characterization | | |
|---|---|---|---|---|---|---|---|
| | PEG-2000-C-DMA | Compound 13 | Cholesterol | DSPC | Size (nm) | PDI | % Encap |
| 1.6:55 ('Base') | 1.6 | 55 | 33 | 11 | 76 | 0.10 | 95 |
| 1.7:57 ('PL-free') | 1.7 | 57 | 42 | 0 | 78 | 0.09 | 95 |
| 1.8:61 ('PL-free') | 1.8 | 61 | 37 | 0 | 82 | 0.02 | 93 |

The mRNA-LNP were prepared as described in Example 17. Female Balb/C (n=4) received a 0.5 mg/kg (mRNA) intravenous dose of LNP. Six hours later, animals were euthanized with ketamine/xylazine. A small amount (75 µL) of the terminal blood was collected into a tube containing 18.8 µL of 50 mg/L heparin, while the rest of the blood was collected into sodium EDTA microtainer tubes. All of these tubes were centrifuged for 5 min at 16000×g & 16° C. and plasma was isolated. Also, part of the liver was collected into FastPrep tubes which were placed at −80° C. until analysis.

The livers were homogenized in 1×CCLR buffer and were analyzed for luciferase activity using the Luciferase Assay (Promega). As can be seen in Table 45 the efficacy of the PL-free mRNA-LNP formulations are similar to those of the Base (PL-containing) formulation.

TABLE 45

Luciferase Gene Expression in Liver 6 h Post-IV Administration of Base Compositions vs PL-free mLuc-LNP

| Treatment | Luciferase Activity (ng/g liver) | Stdev (ng/g liver) |
|---|---|---|
| 1.6:55 ('Base') | 1708 | 73 |
| 1.7:57 ('PL-free') | 1651 | 70 |
| 1.8:61 ('PL-free') | 1867 | 62 |

The heparin plasma (diluted 1:4000 with ELISA Diluent) was used in a standard Murine EPO ELISA analysis (R&D Systems). As seen in Table 46, the efficacy trend for the mEPO-LNP was similar to that seen with the mLuc-LNP where the efficacies of the PL-free Luc mRNA-LNP are similar to those of the Base (PL-containing) formulation.

TABLE 46

Efficacy of Murine mEPO-LNP in Liver 6 h Post-IV Administration of Base Compositions vs PL-free mEPO-LNP

| Treatment | mEPO (ng/mL) | Stdev (ng/mL) |
|---|---|---|
| PBS | 0.124 | 0.009 |
| 1.6:55 ('Base') | 2839 | 313 |
| 1.7:57 ('PL-free') | 2460 | 611 |
| 1.8:61 ('PL-free') | 3986 | 426 |

To assess immune stimulation, plasma samples were analyzed by ELISA for cytokines MCP-1 and IL-6 (ELISA assays and capture/detection antibodies from BD Biosciences). Results in Table 47a (mEPO) and Table 47b (mLuc) show again how the inflammatory response to the PL-free LNP compositions markedly reduced compared to the Base composition. This is true for both sets of LNP (luciferase and EPO). Given that the efficacy of these PL-free compositions has not been impaired, their reduced cytokine induction furnishes a significantly improved therapeutic index.

TABLE 47a

MCP-1 and IL-6 ELISA Results of Base Compositions vs PL-free mEPO-LNP

| Treatment | MCP-1 Average (pg/mL) | MCP-1 Stdev (pg/mL) | IL-6 Average (pg/mL) | IL-6 Stdev (pg/mL) |
|---|---|---|---|---|
| PBS | 47 | 3 | 15 | 3 |
| 1.6:55 ('Base') | 3947 | 440 | 236 | 29 |
| 1.7:57 ('PL-free') | 873 | 431 | 39 | 14 |
| 1.8:61 ('PL-free') | 851 | 110 | 43 | 17 |

TABLE 47b

MCP-1 and IL-6 ELISA Results of Base Compositions vs PL-free mLuc-LNP

| Treatment | MCP-1 Average (pg/mL) | MCP-1 Stdev (pg/mL) | IL-6 Average (pg/mL) | IL-6 Stdev (pg/mL) |
|---|---|---|---|---|
| PBS | 47 | 5 | 14 | 3 |
| 1.6:55 ('Base') | 2474 | 446 | 208 | 31 |
| 1.7:57 ('PL-free') | 1231 | 687 | 27 | 6 |
| 1.8:61 ('PL-free') | 856 | 745 | 30 | 8 |

Example 19

PL-Free LNP with Increased PEG Content are Less Stimulatory

This example demonstrates how a further reduction in mRNA-LNP immune stimulation can be achieved by increasing the PEG component of the PL-free mRNA-LNP, again without impairing activity. The following mRNA-LNP compositions (Table 48) were prepared as described in Example 17, with an EPO mRNA payload:

Female Balb/C (n=4) then received a 0.5 mg/kg (mRNA) intravenous administration of LNP. Six hours later, animals were euthanized with ketamine/xylazine. Blood was collected into sodium EDTA microtainer tubes. All of these tubes were centrifuged for 5 min at 16000×g & 16° C. and plasma was isolated. Plasma samples were analyzed by ELISA for cytokines MCP-1 and IL-6 (ELISA assays and capture/detection antibodies from BD Biosciences). Results in Table 49 shows again how inflammatory response to the PL-free LNP compositions markedly reduced compared to the Base composition. Given that the efficacy of these PL-free compositions has not been impaired, their reduced cytokine induction furnishes a significantly improved therapeutic index.

TABLE 49

MCP-1 and IL-6 ELISA Results of Base Compositions vs High PEG, PL-free mEPO-LNP

| Treatment | MCP-1 Average (pg/mL) | MCP-1 Stdev (pg/mL) | IL-6 Average (pg/mL) | IL-6 Stdev (pg/mL) |
|---|---|---|---|---|
| PBS | 57 | 4 | 15 | 3 |
| 1.6:55 ('Base') | 2875 | 2317 | 244 | 112 |
| 1.8:61 ('PL-free') | 1204 | 460 | 77 | 22 |
| 3.3:55 ('PL-free') | 712 | 186 | 37 | 11 |

These results demonstrate that by increasing the amount of PEG lipid to 3.3 mol % within the PL-free formulation (3.3:55 Compound 13 PL-free mRNA-LNP), a further reduction in the immune stimulation of the mRNA-LNP can be achieved. The potency of the 3.3:55 composition was next examined.

Example 20

High PEG, PL-Free mRNA-LNP Remain Surprisingly Potent, and Exhibit a Larger Therapeutic Index This example demonstrates that the high PEG, PL-free 3.3:55 mRNA-LNP composition is just as efficacious as the Base, PL-containing composition. It again shows the reduced immune stimulation of the 3.3:55 composition and therefore the improved Therapeutic Index. The following LNP were prepared using the process described in Example 17 (Table 50), with an EPO payload:

TABLE 48

Formulation characteristics of 1.6:55 Base Formulation vs PL-free mRNA-LNP

| | Lipid Composition (mol %) | | | | Characterization | | |
|---|---|---|---|---|---|---|---|
| | PEG-2000-C-DMA | Compound 13 | Cholesterol | DSPC | Size (nm) | PDI | % Encap |
| 1.6:55 ('Base') | 1.6 | 55 | 33 | 11 | 73 | 0.07 | 97 |
| 1.8:61 ('PL-free') | 1.8 | 61 | 37 | 0 | 86 | 0.06 | 96 |
| 3.3:55 ('PL-free') | 3.3 | 55 | 41 | 0 | 59 | 0.06 | 96 |

TABLE 50

Formulation characteristics of 1.6:55 Base Formulation vs High PEG, PL-free mEPO-LNP

| | Lipid Composition (mol %) | | | | Characterization | | |
|---|---|---|---|---|---|---|---|
| | PEG-2000-C-DMA | Compound 13 | Cholesterol | DSPC | Size (nm) | PDI | % Encap |
| 1.6:55 ('Base') | 1.6 | 55 | 33 | 11 | 74 | 0.07 | 97 |
| 3.3:55 ('PL-free') | 3.3 | 55 | 41 | 0 | 63 | 0.06 | 96 |

Female Balb/C (n=4) then received a 0.5 mg/kg (mRNA) intravenous administration of LNP. Six hours later, animals were euthanized with ketamine/xylazine. At time points of 2 h, 3 h, 4 h & 5 h blood draws were performed and 20 μL of the blood was collected into a tube containing 5 μL of 50 mg/L heparin. Then at 6 hour time point, the animals were euthanized with a lethal dose of ketamine/xylazine. A small amount (20 μL) of the terminal blood was collected into a tube containing 5 μL of 50 mg/L heparin, while the rest of the blood was collected into sodium EDTA microtainer tubes. Tubes were centrifuged for 5 min at 16000×g & 16° C. and to isolate plasma.

Heparin plasma analyzed by ELISA (kit from R&D Systems) for EPO concentrations. As seen in Table 51, at all the time points the efficacy of the PL-containing mRNA-LNP and the 3.3:55 PL-free formulation are equivalent.

TABLE 51

Efficacy of Murine mEPO-LNP in Liver 6 h Post-IV Administration of Base Compositions vs High PEG, PL-free mEPO-LNP

| | 1.6:55 ('Base') | | 3.3:55 ('PL-free') | |
|---|---|---|---|---|
| Time Point (h) | EPO (ng/mL) | Stdev (ng/mL) | EPO (ng/mL) | Stdev (ng/mL) |
| 2 | 5065 | 773 | 4832 | 843 |
| 3 | 6174 | 514 | 6412 | 1188 |
| 4 | 5194 | 485 | 5902 | 1093 |
| 5 | 3961 | 643 | 4313 | 768 |
| 6 | 2936 | 528 | 3055 | 521 |

Plasma samples were analyzed by ELISA for cytokines MCP-1 and IL-6 (ELISA assays and capture/detection antibodies from BD Biosciences). Results in Table 52 corroborate the data in Example 19, and show again how the inflammatory response to the high PEG, PL-free LNP compositions is markedly reduced compared to the Base composition.

TABLE 52

MCP-1 and IL-6 ELISA Results of Base Compositions vs High PEG, PL-free mEPO-LNP

| | MCP-1 | | IL-6 | |
|---|---|---|---|---|
| Treatment | Average (pg/mL) | Stdev (pg/mL) | Average (pg/mL) | Stdev (pg/mL) |
| PBS | 67 | 3 | 22 | 4 |
| 1.6:55 ('Base') | 2402 | 1317 | 163 | 74 |
| 3.3:55 ('PL-free') | 485 | 210 | 36 | 12 |

Taken together these results demonstrate that by using a PL-free formulation the therapeutic index of an mRNA-LNP formulation can be increased and further by changing the formulation to include higher amounts of PEG (e.g., 3.3 mol %) the therapeutic index can be further advanced.

Example 21

Use of HPLC Purified mRNA for Immune Stimulation Abrogation of mRNA-LNP

This example demonstrates how a reduction in mRNA-LNP immune stimulation can be achieved by replacing regular silica membrane purified mRNA with Reverse Phase (RP) HPLC-purified mRNA in LNP. Murine erythropoietin (EPO) mRNA purified by either method was formulated in LNP and injected via the iv route into Balb/C mice. Four hours following injection the animals were sacrificed and plasma & liver tissue were analyzed for efficacy and immune stimulation.

LNP were prepared by the regular LipoMixer technology. In brief, a 7.36 mg/mL lipid solution in 100% ethanol was prepared containing the lipids DSPC:Chol:PEG$_{2000}$-C-DMA:Compound 13 in the following molar ratios: 10.9:32.8:1.64:54.6, mol %. The mRNA payload was solubilized in 40 mM EDTA (pH 4.5) at a concentration of 0.366 mg/mL. Equal volumes of each solution (1.6 mL) were blended at 250 mL/min through a T-connector using the Direct Dilution method described by Jeffs et al. The resulting mixture was subsequently collected directly into a tube containing ~4 volumes (5.9 mL) of PBS, pH 7.4. These formulations were placed in Slide-A-Lyzer dialysis units (MWCO 10,000) and were dialyzed overnight against 100 volumes of PBS, pH 7.4. Following dialysis the formulations were concentrated to ~0.6 mg/mL using VivaSpin concentrator units (MWCO 100,000).

Female Balb/C mice (n=5) received an intravenous (tail vein) administration of either PBS, or LNP bearing either a regularly purified (silica membrane) or HPLC-purified mRNA payload. The mRNA transcript encoded mouse erythropoietin (EPO). Each animal received a dose corresponding to 0.5 mg/kg mRNA. Four hours following injection the animals were euthanized with a lethal dose of ketamine/xylazine. A small amount (20 μL) of the terminal blood was collected into a tube containing 5 μL of 50 mg/L heparin, while the rest of the blood was collected into Na EDTA microtainer tubes. All tubes were centrifuged for 5 min at 16000×g & 16° C. to isolate plasma. Half of the left lateral lobe was collected into 1.5 mL of RNALater and stored at 4° C. for at least 16 h.

The heparin plasma (diluted 1:4000 with ELISA Diluent) was used in a standard Murine EPO ELISA analysis (kit from R&D Systems). As can be seen in Table 53 the efficacy of the LNP containing the highly (HPLC) purified EPO mRNA is very similar to that of the regular (Silica Membrane) purified EPO mRNA. The regular level of EPO seen within the plasma of mice treated with PBS is 100-200 pg/mL. Therefore, regardless of the purity of the EPO mRNA incorporated the level of liver gene expression of EPO from the encapsulated mEPO is extremely high.

To determine the level of immune stimulation caused by mRNA-LNP, the fold increase of IFIT mRNA within the livers for the LNP treated animals (over the PBS treated animals) was determined. This is one example of an assay the art worker can use to assess the level of immune stimulation caused by mRNA-LNP. In certain embodiments, the HPLC-purified mRNA-LNP induces significantly less immune stimulation than a control, which in certain embodiments is characterized by the IFIT response. The IFN-inducible IFIT1 mRNA, the most strongly induced mRNA in response to type I IFN, was used as a more sensitive measure of immune stimulation. Strong IFIT1 mRNA induction in both liver and spleen can be observed in mice treated with LNP bearing nucleic acids, even in the absence of detectable plasma IFN protein. This likely reflects local IFN induction that does not manifest as a systemic cytokine response. In the IFIT1 assay, the amount of IFIT1 mRNA in hepatocytes was quantified and normalized to mRNA levels of a housekeeping gene (usually GAPD), which typically remains constant. A QuantiGene 2.0 kit (a branched DNA based assay) from Affymetrix was used to determine mRNA levels of both genes.

Approximately 20-25 mg of the left lateral lobe of the livers (stored in RNALater) were homogenized. Relative mRNA levels of both IFIT & and the house keeping gene GAPD were determined using the QuantiGene 2.0 Assay. IFIT readouts were normalized to GAPD for each group of animals, and expressed as a fold increase over the PBS control group. The results in Table 54 demonstrate that LNP bearing an mRNA payload purified by silica membrane yielded a 627-fold increase in IFIT, vs the PBS group. Mice treated with LNP bearing an HPLC-purified payload exhibited only a 21-fold increase vs PBS. Thus they are approx. 30-fold less stimulatory than particles bearing silica-membrane purified mRNA. In certain embodiments, the lipid nanoparticle formulation having HPLC-purified mRNA has an IFIT response that is no more than 30 fold greater than a reference IFIT response of phosphate buffered saline. In certain embodiments, the lipid nanoparticle formulation having HPLC-purified mRNA has an IFIT response that is no more than 10 or 20 or 30 or 40 or 50 or 60 or 70 or 80 or 90 or 100 fold greater than a reference IFIT response of phosphate buffered saline.

Further comparison of immune stimulatory capacity was afforded by analysis of the EDTA plasma in cytokine (MCP-1 and IL-6) ELISA assays. Plasma was diluted (1:8 or 1:80) in ELISA diluent and was analyzed for levels of MCP-1 & IL-6 presence using ELISA assays with capture & detection antibodies from BD Biosciences. The level of MCP-1 is dramatically reduced (37106 pg/mL down to 105 pg/mL) with the incorporation of the HPLC purified mRNA. Similarly, another cytokine (IL-6) is also dramatically reduced (4805 pg/mL reduced to 22 pg/mL) when using the HPLC purified mRNA. Results are shown in Table 55.

Taken together these results demonstrate that LNP particles bearing an HPLC-purified mRNA payload are significantly less stimulatory than those with a less refined (e.g. regular silica membrane purified) mRNA payload. Given that the efficacy is not adversely affected, this represents a dramatic increase in the therapeutic index of the mRNA-LNP.

TABLE 53

EPO Efficacy of 0.5 mg/kg 1.6:55 Compound 13 Containing Regular Silica Membrane Purified or HPLC Purified Murine mEPO 4 h Following IV Dosing in Balb/C Mice (n = 5)

| Treatment | EPO (ng/mL) | Stdev (ng/mL) |
|---|---|---|
| 1.6:55 ('Base') with Regular Purified Murine mEPO | 4050 | 450 |
| 1.6:55 ('Base') with HPLC Purified Murine mEPO | 4525 | 385 |

TABLE 54

IFIT Induction of 0.5 mg/kg 1.6:55 Compound 13 Containing Regular Silica Membrane Purified or HPLC Purified Murine mEPO 4 h Following IV Dosing in Balb/C Mice (n = 5)

| | IFIT (Fold Increase Over PBS) | |
|---|---|---|
| Treatment | Average | Stdev |
| PBS | 1.0 | 0.3 |
| 1.6:55 ('Base') with Regular Purified Murine mEPO | 627 | 52 |
| 1.6:55 ('Base') with HPLC Purified Murine mEPO | 21 | 12 |

TABLE 55

MCP-1 and IL-6 ELISA Results in Balb/C Mice 4 h Following IV Dosing of 0.5 mg/kg of 1.6:55 Compound 13 Containing Regular Silica Membrane Purified or HPLC Purified Murine mEPO (n = 5)

| | MCP-1 | | IL-6 | |
|---|---|---|---|---|
| Treatment | Average (pg/mL) | Stdev (pg/mL) | Average (pg/mL) | Stdev (pg/mL) |
| PBS | 56 | 3 | 17 | 2 |
| 1.6:55 ('Base') with Regular Purified Murine mEPO | 37106 | 12621 | 4805 | 1075 |
| 1.6:55 ('Base') with HPLC Purified Murine mEPO | 105 | 18 | 22 | 6 |

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A lipid nanoparticle comprising:
   (a) a cationic lipid;
   (b) a PEG-lipid conjugate present in an amount of at least 3 mole percent; and
   (c) mRNA encapsulated within the lipid nanoparticle;
   provided that the lipid nanoparticle comprises less than 0.5 mole percent phospholipid.

2. The lipid nanoparticle of claim 1, wherein the PEG-lipid conjugate is selected from the group consisting of a PEG-diacylglycerol (PEG-DAG) conjugate, a PEG-dialkyloxypropyl (PEG-DAA) conjugate, a PEG-ceramide (PEG-Cer) conjugate, and a mixture thereof.

3. The lipid nanoparticle of claim 1, wherein the PEG-lipid conjugate is a PEG-2000-C-DMA conjugate.

4. The lipid nanoparticle of claim 2, wherein the PEG-DAA conjugate is selected from the group consisting of a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, and a mixture thereof.

5. The lipid nanoparticle of claim 1, wherein the lipid nanoparticle has a lipid:nucleic mass ratio of from about 9:1 to about 20:1.

6. The lipid nanoparticle of claim 1, wherein the mRNA is chemically modified.

7. The lipid nanoparticle of claim 1, wherein the lipid nanoparticle comprises an electron dense core.

8. The lipid nanoparticle of claim 1, wherein the lipid nanoparticle comprises an electron dense core and wherein the mRNA is located within the electron dense core.

9. A population of lipid nanoparticles comprising a multiplicity of lipid nanoparticles of claim 1.

10. A pharmaceutical composition comprising the lipid nanoparticle of claim 1, and a pharmaceutically acceptable carrier.

* * * * *